(12) United States Patent
Pereira et al.

(10) Patent No.: US 7,611,725 B2
(45) Date of Patent: Nov. 3, 2009

(54) ADDITIVES AND PRODUCTS INCLUDING OLIGOESTERS

(75) Inventors: Abel G. Pereira, Belleville, NJ (US); Helena S. Barinova, Iselin, NJ (US); Christopher Westergom, Hillsborough, NJ (US)

(73) Assignee: Croda, Inc., Edison, NJ (US)

( * ) Notice: Subject to any disclaimer, the term of this patent is extended or adjusted under 35 U.S.C. 154(b) by 389 days.

(21) Appl. No.: 10/356,208

(22) Filed: Jan. 31, 2003

(65) Prior Publication Data

US 2003/0199593 A1    Oct. 23, 2003

Related U.S. Application Data

(60) Provisional application No. 60/353,669, filed on Jan. 31, 2002, provisional application No. 60/353,477, filed on Jan. 31, 2002, provisional application No. 60/353,540, filed on Feb. 1, 2002.

(51) Int. Cl.
| | |
|---|---|
| A61K 8/02 | (2006.01) |
| A61K 47/00 | (2006.01) |
| A61K 47/30 | (2006.01) |
| C11D 1/62 | (2006.01) |
| C07C 69/34 | (2006.01) |
| C08G 63/02 | (2006.01) |
| C08G 63/00 | (2006.01) |
| A61Q 5/12 | (2006.01) |

(52) U.S. Cl. ............... 424/401; 424/70.27; 424/70.28; 514/785; 514/788.1; 560/190; 560/196; 528/272; 528/301; 528/302; 528/308

(58) Field of Classification Search .............. 424/401, 424/70.28, 70.27, 70.26; 554/110; 528/272, 528/301, 302, 308; 560/190, 196; 514/110, 514/785, 788.1
See application file for complete search history.

(56) References Cited

U.S. PATENT DOCUMENTS

| | | | |
|---|---|---|---|
| 1,985,424 | A | 12/1934 | Piggott |
| 2,438,091 | A | 3/1948 | Lynch |
| 2,528,378 | A | 10/1950 | Mannheimer |
| 2,658,072 | A | 11/1953 | Kosmin |
| 2,703,798 | A | 3/1955 | Schwartz |
| 2,965,576 | A | 12/1960 | Wilson |
| 3,155,591 | A | 11/1964 | Hilfer |

(Continued)

FOREIGN PATENT DOCUMENTS

EP        095238 A2    11/1983

(Continued)

OTHER PUBLICATIONS

Supplementary European Search Report, EP 03 70 8916, Jul. 29, 2008.

*Primary Examiner*—Shengjun Wang
(74) *Attorney, Agent, or Firm*—Lerner, David, Littenberg, Krumholz & Mentlik, LLP

(57) ABSTRACT

The present invention relates to oligoesters and their use or the creation of additives. Oligoester containing additives and/or oligoesters themselves may be used for formulating pharmaceutical preparations, cosmetics or personal care products such as shampoos and conditioners. These oligoesters are particularly useful for the creation of multi-purpose additives that can impart conditioning, long substantivity and/or UV protection. Individual oligoesters and oligoester mixtures are described.

35 Claims, 1 Drawing Sheet

Polyester MDPA Intermediate Lot P-2737

| Retention Time | Mn | Mw | Mp |
|---|---|---|---|
| 14.43 | 1537 | 2703 | 2845 |

U.S. PATENT DOCUMENTS

| | | |
|---|---|---|
| 3,755,560 A | 8/1973 | Dickert |
| 3,778,287 A | 12/1973 | Stansfield et al. |
| 3,929,678 A | 12/1975 | Laughlin et al. |
| 3,959,461 A | 5/1976 | Bailey et al. |
| 4,185,017 A | 1/1980 | Piesch et al. |
| 4,275,055 A | 6/1981 | Nachtigal et al. |
| 4,387,090 A | 6/1983 | Bolich, Jr. |
| 4,421,769 A | 12/1983 | Dixon et al. |
| 4,557,853 A | 12/1985 | Collins |
| 4,704,272 A | 11/1987 | Oh et al. |
| 4,741,855 A | 5/1988 | Grote et al. |
| 4,788,006 A | 11/1988 | Bolich, Jr. et al. |
| 4,902,499 A | 2/1990 | Bolish, Jr. et al. |
| 4,919,934 A | 4/1990 | Deckner et al. |
| 4,976,953 A | 12/1990 | Orr et al. |
| 5,011,681 A | 4/1991 | Ciotti et al. |
| 5,120,532 A | 6/1992 | Wells et al. |
| 5,151,209 A | 9/1992 | McCall et al. |
| 5,151,210 A | 9/1992 | Steuri et al. |
| 5,382,377 A | 1/1995 | Raehse et al. |
| 5,455,025 A | 10/1995 | Pereira et al. |
| 5,597,555 A | 1/1997 | Pereira et al. |
| 5,633,403 A | 5/1997 | Gallagher et al. |
| 5,674,832 A | 10/1997 | Keys |
| 5,880,299 A | 3/1999 | Ponsati Obiols et al. |
| 5,961,966 A | 10/1999 | Abend et al. |
| 6,045,779 A * | 4/2000 | Mueller et al. ............... 424/47 |
| 6,190,645 B1 | 2/2001 | SaNogueira et al. |
| 6,207,778 B1 | 3/2001 | Jachowicz et al. |
| 6,211,139 B1 | 4/2001 | Keys et al. |
| 6,641,803 B1 * | 11/2003 | Kahre et al. ............... 424/70.1 |
| 2002/0002297 A1 | 1/2002 | Keys |

FOREIGN PATENT DOCUMENTS

| | | |
|---|---|---|
| EP | 0937452 A2 | 8/1999 |
| EP | 1160238 A2 | 12/2001 |
| WO | WO 99/18178 | 4/1999 |

* cited by examiner

ADDITIVES AND PRODUCTS INCLUDING OLIGOESTERS

CROSS-REFERENCE TO RELATED APPLICATIONS

This application claims the benefit of U.S. Provisional Application No. 60/353,477, filed Jan. 31, 2002, U.S. Provisional Application No. 60/353,669, filed Jan. 31, 2002, and U.S. Provisional Application No. 60/353,540, filed Feb. 1, 2002, the disclosures of which are all incorporated by reference.

BACKGROUND OF THE INVENTION

There are many known types of quaternary compounds or "quats" and they have been used in many fields. Quats can be tremendously useful compounds. Certain quats, however, are not particularly environmentally friendly. These quats break down very slowly and could constitute an environmental pollution. Because they have reactive nitrogen species, they can have previously unrecognized activity.

Other quats, such as ester quats which contain ester linkages, are far more environmentally friendly in as much as they degrade much more readily. However, ester quats are often stable only in a relatively narrow and generally acidic range of pH. In addition, ester quats can have a relatively lower substantivity, i.e., they can be easily stripped from hair or skin during washing, bathing or during such activities as swimming. Certainly, compounds with improved environmental properties, improved substantivity and generally higher levels of quaternary activity or quaternary groups per molecule would therefore be highly desirable.

SUMMARY OF THE INVENTION

The present invention relates to a number of compositions of matter also referred to herein as compounds or molecules, as well as mixtures of such compounds. All are oligoesters and share a single common feature namely an oligoester backbone. An oligoester backbone in accordance with the present invention is made up of diol fragments, preferably containing a nitrogen that can be protonated and/or quaternized and diacid fragments. Diacid fragments may also include a nitrogen that can be protonated and/or quaternized. Preferably, the diacid and diol fragments are alternating with each other in the oligoester backbone. Because the diacid fragments are bound to the diol fragments via ester groups or ester linkages, the compounds of the present invention can be thought of as polyesters or oligoesters. Indeed, the oligoesters of the present invention have a backbone that includes at least two, preferably at least three, more preferably at least four such ester groups or linkages within and along the backbone. In addition, the oligoester backbones of the present invention preferably include within their structure at least two nitrogen atoms that can be protonated or quaternized. These are preferably tertiary nitrogens; nitrogens having at least three bonds to something other than hydrogen, and most preferably to nitrogen, oxygen, carbon or sulfur.

The oligoester backbone may include fragments derived from more than one diol and/or diacid. More preferably, however, the oligoester backbone includes one type of the diol-derived fragment and one type of the diacid-derived fragment arranged in a repeating fashion. One diol-derived fragment and one diacid-derived fragment bound by an ester linkage form a "structural unit" and the oligoesters of the present invention preferably include a backbone made from at least two distinct structural units, whether or not the diols and diacids within the individual structural units are the same or different from one another. Oligoesters in accordance with the present invention may also include an additional diol or diacid fragment (essentially half of a structural unit) such that they terminate at each end, with the same group, e.g., both carboxy groups or both hydroxy groups. More preferably, oligoesters of the present invention include at least three structural units and even more preferably between about three and about 100 structural units. Even more preferably, the oligoesters of the invention have between 3 and about 50 subunits and even more preferably between 3 and 25 subunits. They may also have an additional diacid or diol fragment as described above. Stated another way, the oligoesters of the present invention have at least two structural units and a molecular weight of about 100,000 or less, more preferably 50,000 or less and most preferably 25,000 or less.

The oligoester backbone may be created via a reaction between individual diacids and diols, groups of each, and even smaller oligoesters. The oligoesters may be then derivatized to produce various derivatized oligoesters such as by protonating the nitrogen groups, adding groups to nitrogens in the backbone to form tertiary or quaternary nitrogens.

It should be understood that some or all of the diol and/or diacid fragments might be in fact derived from previously derivatized, substituted or esterified diacids and/or diols prior to constructing structural units or backbones, e.g., diacid-derived fragments may be derived from a diacid, a diester, a diacid di-halide, an anhydride and so on; and the diol-derived fragments may be derived from esterified or quaternized diols and the like. Examples of the reactions include reactions between a diacid and a diol, a diester and a diol, a diacid halide and a diol, and an anhydride and a diol, and the like.

In accordance with a preferred aspect of the present invention, the oligoesters include one or more nitrogen atoms. Preferably, the nitrogen atom(s) is one part of an amine group. The amine group may be primary, secondary, tertiary or quaternary. Preferably, the amine group is tertiary or quaternary; most preferably, the oligoester includes quaternary amine groups. In a particularly preferred embodiment, the amines in the oligoester backbone are functionalized to form quats. The amine group may be part of the some or all of the diol fragments, some or all of the diacid fragments or both. Preferably, the amine group is part of the diol fragments. More preferably, the amine group is part of every structural unit. However, it is also contemplated that the amine group may be part of only some of the structural units. Thus, two diols in two structural units of an oligoester having fine structural units could contain nitrogen atoms that, when derivatized, become quaternary groups or "quats" while the other three diols have nothing but alkyl groups between the two alcohol functional groups of the diols. Obviously, the order of the amine diols can be random or they can be placed where desired within the string of structural units making up the oligoester's backbone.

The oligoesters in accordance with the present invention are useful as additives in pharmaceuticals, personal care products and cosmetics. The oligoesters of the invention, particularly those made up of non-derivatized backbones, can be used as thickeners, emulsifying agents, bulking agents and the like. Non-derivatized oligoester backbones containing diol fragments and diacid fragments can be used as intermediates for the creation of a number of very useful molecules which are themselves useful in personal care products, cosmetics and pharmaceuticals. Depending upon the structure of the backbone and how it is derivatized, the properties of this important class of compounds can be adjusted and tailored.

The nitrogen atoms in the backbone of the oligoesters can be derivatized with any group that can conventionally be added to a secondary or tertiary amine or nitrogen. These include, without limitations, lactones, expoxys, compounds with halogen leaving groups such as chloroacetic acid, peroxide (to make amine oxides), siloxanes, etc.). One of the preferred derivatized oligoesters in accordance with one aspect of the invention provides UV-protecting oligoesters that contain the oligoester backbone and a UV-protecting molecular system, group, moiety or the like attached to the nitrogen atoms of the backbone. In the more preferred embodiment, the invention provides UV-protecting oligoester quats that further include a quaternized nitrogen atom(s), preferably within the oligoester backbone. The UV-protecting group is, in a preferred embodiment, the derivatizing group used to create quats from nitrogen molecules in the backbone. Alternatively, the UV-protecting group may be attached to the backbone as an end cap through an ester or ether linkage, or may be attached to a nitrogen in the backbone through a bridging molecule.

The oligoesters described herein may be modified by the inclusion of alkoxy groups (or alkoxylated) within the oligoester backbone. Stated another way, the diol fragments of the backbone may include one or more alkoxy groups. Such alkoxylated diol fragments may be introduced in the backbone via alkoxylation of non-alkoxy-containing diols, which then may be used to produce backbones, or they might be produced by any other conventional means. The alkoxylated oligoesters may then be derivatized if desired.

The inventors have discovered that oligoesters having alkoxylated backbone can be formulated and maintained at a generally neutral pH, as well as at a mildly basic and mildly acidic pHs. Such oligoesters may be formulated and maintained at pHs greater than 4 and less than 9. Prior art ester compositions and particularly esterquats are generally unstable at a pH above four and this dramatically inhibits the ability to use such products, particularly in shampoos and cosmetics. Oligoesters with alkoxy groups in their backbone can be used in place of conventional ester quats in formulations at neutral pH, mildly acidic pH, or mildly basic pH, for example at pHs from 4 to 9.

Preferably, the backbones of oligoesters in accordance with the present invention terminate in a hydroxy group (—OH) or similar functionality, a carboxy-containing group, such as (—C(O)OH), ester group —C(O)OR, an ether group and the like. Whether the backbone is hydroxy-terminated, carboxy-terminated or both, the terminal functional group(s) may also be derivatized. Thus, the terminal hydroxy group(s), carboxy group(s), or both may be "end-capped." For example, oligoesters having a terminal hydroxy group may be end-capped via esterification with a desired compound(s) bearing carboxy-containing reactive group, such as the carboxylic group —C(O)OH, ester group —C(O)OR, or any other suitable group. Likewise, the carboxy-terminated oligoesters may be end-capped via esterification with a desired compound(s) bearing a hydroxy group or other suitable reactive functionality. Ether groups may also be formed. End caps can be simple such as hydrogen or methyl group or they can be large and complex such as a group derived from polyricinoleate. The latter (and other similar compounds having high hydrophobic content) can contribute to the overall properties of the oligoester, improving, for example, conditioning of hair and/or skin. Therefore, the compounds of this aspect of the invention can be used to make oligoesters which are particularly useful as hair and skin conditioners. Because of their high hydrophobicity (believed to be related to the size of their alkyl chains), such compounds will often remain on the hair or skin without washing off for longer periods of time.

These advantageous features can also be readily combined, providing an end-capped oligoester comprised of repeating units containing diol fragments, diacid fragments, and alkoxy groups, for example, providing an end-capped oligoester, which is both stable at generally neutral, mild basic and mild acidic pH, and able to provide effective conditioning. This would allow the creation of conditioners which can be used in conjunction with shampoos, products which can generally not be formulated at the more acid pHs necessary to maintain the stability of esterquats.

A particularly preferred aspect of the present invention is oligoester quats. The quaternary groups of oligoesters of the present invention can be constructed from backbones that include amine nitrogen(s) that are reacted with a fourth group so as to form a positively charged quaternary nitrogen or "quat." The quaternizing groups that can be used in accordance with the present invention to produce oligoester quats can include those conventionally used in the formation of quats for pharmaceuticals, personal care products and cosmetics. However, they may also include, for example, groups which can act as UV radiation absorbers or UV-protecting group. Again, these features can be combined in the single molecule. So, for example, an oligoester quat end-capped with groups which provide effective conditioning, quaternized with groups providing UV absorption characteristics and alkoxylated within the oligoester backbone to impart neutral pH stability is contemplated. The oligoesters of the present invention can be used as a part of the formulation of pharmaceutical products, personal care products and cosmetics by being mixed, blended, or reacted, in a convention manner, with traditional ingredients for such products. In a preferred aspect, the invention is directed to such products including, in particular, shampoos, conditioners, soaps, sunscreens, and combinations of these, applied to the skin and/or hair.

The present invention also relates to methods of treating patients including mammals and in particular, humans, by applying, topically, various pharmaceutical, cosmetic or personal care products produced in accordance with the present invention containing the oligoesters of the present invention. These would be applied in the conventional manner with regard to pharmaceutical products, topical application includes not only transdermal patches, creams, gels and other traditional topical applications, but also application to the nasal and sinus cavities, the windpipe and esophagus, and even the lungs as well as other mucosal membranes including those found in the mouth, rectum or vagina using suppositories, nasal sprays, inhalers, enemas and the like.

DETAILED DESCRIPTION

Figure 1:
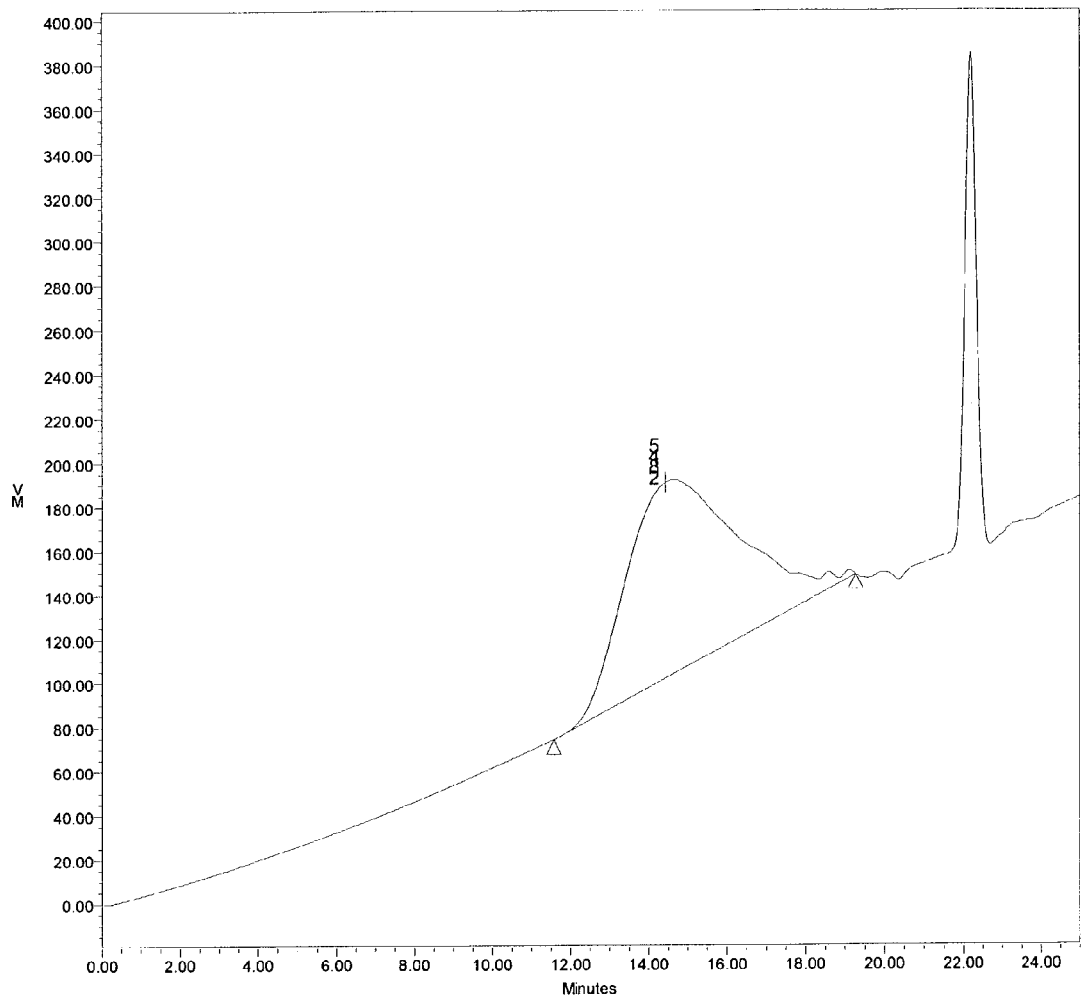
FIG. 1 is a chromatogram of the oligoesters produced in accordance with Example 2 using gel permeation chromatography ("GPC").

It should be understood that when a range is described, every data point within the range, as well as the upper and lower points, are also described.

For the purposes of the present invention, various terms used herein are defined as follows.

A "compound" is a distinct substance, e.g. molecules of the same chemical structure. A "compound" is not a mixture of molecules having different chemical structures. A mixture of oligoesters is a mixture of two or more different oligoester molecules. The mixture is generally identified by the oligoester that exists in the mixture in the highest proportion relative to any other single oligoester in that mixture.

The substitution patterns described as $C_x$-$C_y$ define substituents having carbon chains that may range from x carbon atoms to y carbon atoms, and are referred to as $C_x$-$C_y$ groups. In this regard, a description of the range encompasses carbon chains of every length inside the described range, as well as the upper and lower ends of the range. For example, the substitution pattern described as "$C_1$-$C_8$" encompasses all carbon chains having from 1 to 8 carbon atoms, inclusive.

The oligoesters in accordance with the present invention preferably have structural units that have the structural formulas I and II.

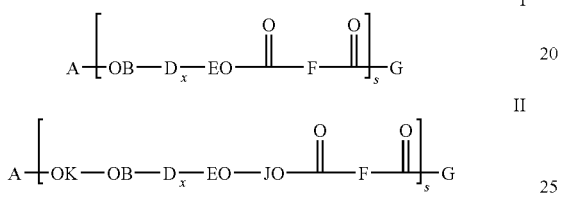

S is a whole number of 2 or greater, more preferably between 2 and 100, even more preferably between 3 and 50, and most preferably between 3 and 25, and is the number of structural units in the oligoester backbone. This number does not include an additional diol or diacid fragment that may be used so that each end of the oligoester terminates in the same type of fragment. X is 0 or 1.

OB-D-EO is a diol fragment. OB and EO may have the formula —$CH_2$—O, although OB and EO could also be substituted as well to provide, merely for example, —CHCl—O— or —CHCH$_3$—O—.

D may be an alkyl group or radical or an alkylene group, saturated or unsaturated, straight chain or branched, substituted or unsubstituted, having 1 to 50 carbon atoms, preferably, 1 to 40 carbon atoms and even more preferably 1 to 18 carbon atoms. Thus, D may be an aliphatic group, saturated or unsaturated, straight chain or branched, substituted or unsubstituted, having 1 to 50 carbon atoms, preferably, 1 to 40 carbon atoms and even more preferably 1 to 18 carbon atoms. D may also be an aromatic group such as aryl-, phenylaryl-, alkylaryl-, or naphthalene group, having 6 to 40 carbon atoms, preferably, 6 to 35 carbon atoms. If D is an aromatic group, D may include an aromatic nucleus, preferably having 6 to 18 carbon atoms, more preferably 6, 10 or 14 carbon atoms. D may also be a cyclic alkane such as cyclohexane having 4 to 35 carbons. D may also be $SiR_1R_2$, a siloxane or a polysiloxane.

Preferably, D may be, or may include, one or more heteroatoms, such as nitrogen, sulfur, or silicon, more preferably, nitrogen —$NR_3$—, $NR_{10}$—, —$N^+R_3R_{10}$—. D may have one or more internal substitution, such as —$(CR_1R_2)_p$—$NR_3$—$(CR_4R_5)_r$— and $(CR_1R_2)_p$—S—$(CR_4R_5)_r$— and —$(CR_1R_2)_p$—NH—$(CR_4R_5)_r$.

Internal substitutions are within the backbone, external area pendant substitutions. Internal substitutions with S, SO, $SiR_1R_2$, siloxane or polysiloxane are also preferred. D may, instead of or in addition to internal substitutions, have one or more external substitutions wherein one or more of the atoms in the backbone are substituted with one or more halogen, carbon, oxygen, nitrogen, sulfur or Si containing groups.

These include —OH, $OR_{11}$, —$NH_2$, —$NHR_{11}$, $NR_{11}R_{12}$, SO, $SO_2$. Non-limiting examples of an internal substitution are —$(CH_2)_3$—NH—$(CH_2)_2$— and —$(CH_2)_3$—S—$(CH_2)_2$— and non-limiting examples of internal and/or external substitutions include —$(CH_2)_3$—$N^+CH_3(CH_2)_{21}CH_3$—$(CH_2)_2$—, —$(CH_2)_3$—$NCH_3$—$(CH_2)_2$— and $CH_2N^+C_2H_4OH(CH_3)$—$CH_2$—$CH(CH_3)$—.

Non-limiting examples of the diol fragments —OB-D-EO— include:

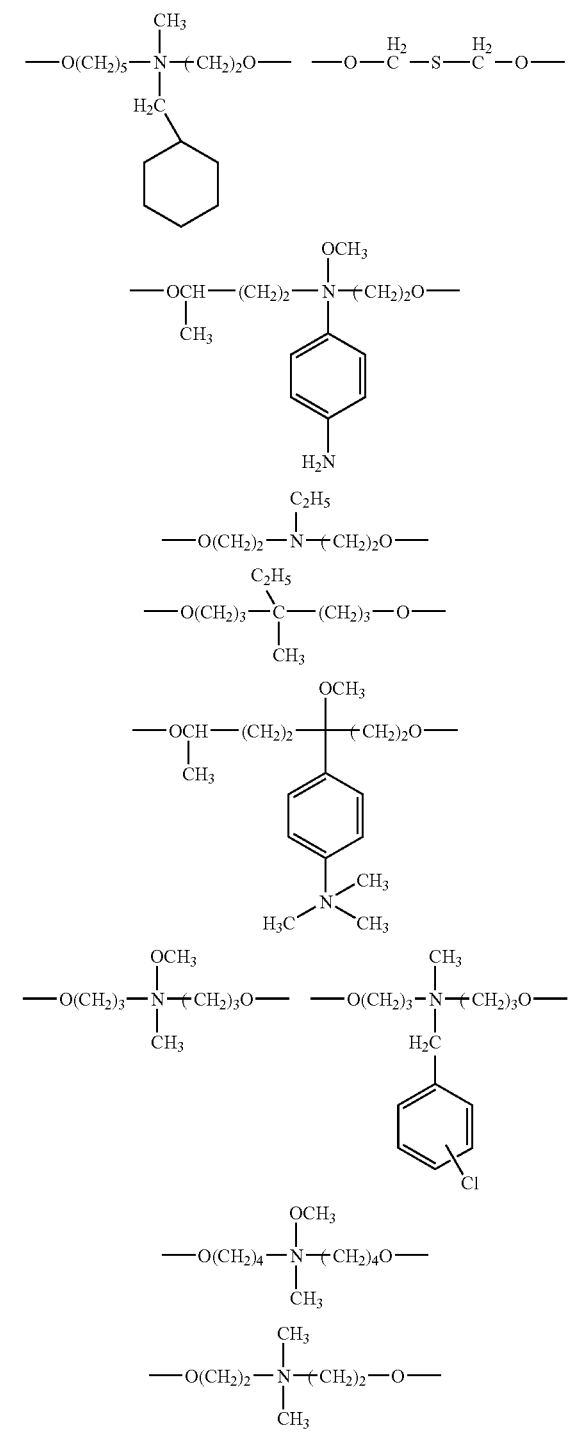

-continued

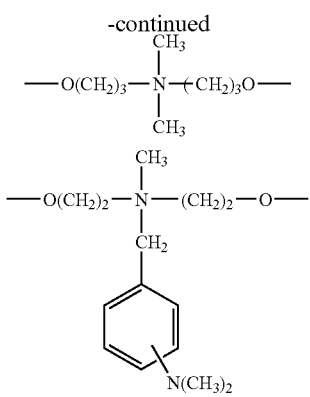

It is preferred that the diol fragment —OB-D-EO— is, or is derived from, a symmetrical amine-diol. Particularly preferred diols useful in accordance with the present invention include Neopentyl Glycol; Bisphenols; Resorcinol; Methyl Diethanolamine; Benzyl Diethanolamine; Lauryl Diethanolamine; Cetyl Diethanolamine; Stearyl Diethanolamine; Erucyl Diethanolamine; and Behenyl Diethanolamine.

F is part of the diacid fragment, and is at least one atom, preferably an alkyl or radical or alkylene group, saturated or unsaturated, straight chain or branched, substituted or unsubstituted, having 1 to 60 carbon atoms, preferably, 1 to 40 carbon atoms most preferably 2-18 carbon atoms. Thus, F may be an aliphatic group, saturated or unsaturated, straight chain or branched, substituted or unsubstituted, having 1 to 60 carbon atoms, preferably, 1 to 40 carbon atoms and even more preferably 2 to 18 carbon atoms. F may also be an aromatic group such as aryl-, phenylaryl-, alkylaryl-, or naphthalene group, having 6 to 60 carbon atoms, preferably, 6 to 35 carbon atoms. If F is an aromatic group, F may include an aromatic nucleus, preferably having 6 to 18 carbon atoms, more preferably 6, 10 or 14 carbon atoms. F may also be a cyclic alkane such as cyclohexane or derivative thereof having 4 to 35 carbons. F may have internal and/or external substitutions as discussed for D. The diacid may also be, or may be derived from, for example, an anhydride. Particularly preferred diacids in accordance with the present invention include Azeliec acid; Malonic acid; Pimelic acid; Sebacic acid; Suberic acid; Succinic acid; Phthalic acid; and C36 dimer acid (cas # 61788-89-4).

Most preferably, at least one of D or F in at least one of a diol fragment(s) and diacid fragment(s) of the oligoesters of formulas I and II include an amine group within their backbone. Preferably at least 10% of the D's and/or F's in the backbone include an amine nitrogen, more preferably at least about 30%, most preferably at least about 50%. Most preferably, at least one of the D's and F's in each structural unit of diol and diacid of Formulae I and II includes and amine nitrogen.

D and/or F could also have the structure of

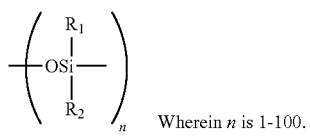 Wherein $n$ is 1-100.

$R_1$, $R_2$, $R_3$, $R_4$, $R_5$, $R_{11}$ and $R_{12}$ may be independently hydrogen an alkyl or alkylene group, or an alkoxy group and may be saturated or unsaturated, straight chain or branched, substituted or unsubstituted, having 1 to 60 carbon atoms, preferably, 1 to 24 carbon atoms, an aromatic group such as aryl-, phenylaryl-, alkylaryl-, or naphthalene group, having 6 to 40 carbon atoms, preferably, 8 to 35 carbon atoms, a cyclic alkane such as cyclohexane having 4 to 35 carbon atoms. Internal and/or external substitutions as described for D and F are also possible.

p and r are independently 0 to 50, more preferably, 2 to 20.

OJ and OK of formula II are alkoxy groups having the formula III,

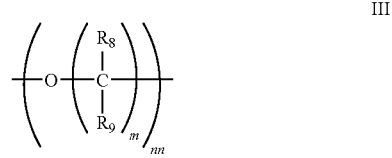

where m and nn are whole numbers, $R_8$ and $R_9$ may be the same or different and may be hydrogen, lower alkyl groups having 1 to 6 carbon atoms, straight chain or branched, saturated or unsaturated, substituted or unsubstituted. Preferably m is 2 and preferably one of $R_8$ or $R_9$ is —$CH_3$, the remaining $R_8$ and $R_9$ groups are H. Therefore, a preferred alkoxy group has the structure of formula III is —OCH(CH$_3$)CH$_2$— or —CH(CH$_3$)CH$_2$O—. In this example, m, which is more preferably 1-6, is 2. When more than one alkoxy group is present in a chain, any structural order may be used. Thus, they may be randomly ordered, ordered in blocks, or ordered in alternating patterns with each other. More preferably, the alkoxy groups of formula III have the structure [O(CH$_2$)$_2$—]$_{nn}$—[OCH(CH$_3$)CH$_2$—]$_{nn}$, where [O(CH$_2$)$_2$—] is an ethoxy group and [OCH(CH$_3$)CH$_2$—] is a propoxy group. Preferably m is 1 to 6 and more preferably 2 to 3 and nn is 0 to 100 and more preferably 1 to 40 and most preferably 1 to 20. In the prior example, m was 2 and nn was also 2.

The following formulae (A) and (B) relate to a particularly preferred group of the oligoesters of the present invention. Note that the various groups are denoted by superscripted numbers as well as the letters p, v, f, and g and not subscripted numbers as used above and elsewhere in this document in connection with formulas I and II. The oligoesters of formulae (A) and (B) are to be considered preferred embodiments of the oligoesters identified previously with regard to formulas I and II. To the extent that any group or substituent is identified in connection with formulas (A) and (B), which falls outside the scope of the corresponding group noted above using subscripted radicals and the accompanying letters in Formula I and II, such groups are to be considered supplementary. A preferred formula similar to that of formula I is formula (A)

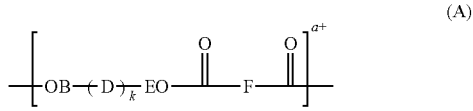

In a preferred embodiment, D has the structure:

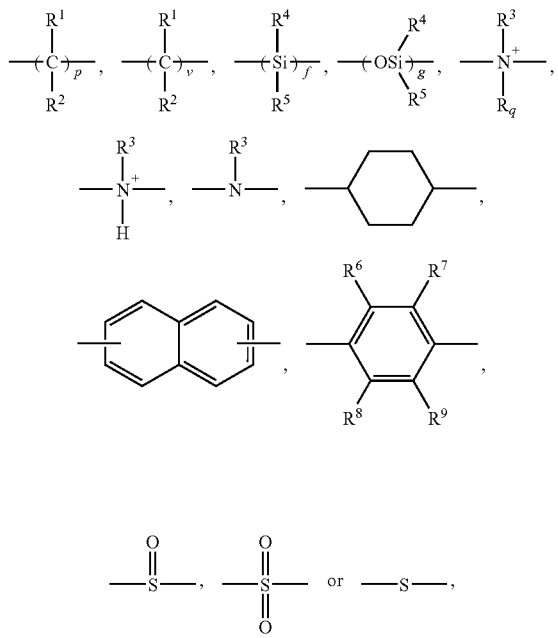

or a combination thereof;

B and E, which may be the same or different, independently have the structure

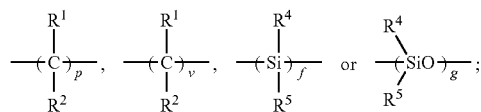

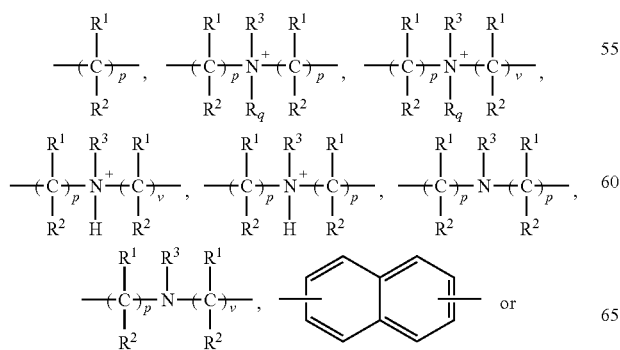

is the diacid fragment, which may be same or different for each diacid fragment of said oligoester, in which F has the structure

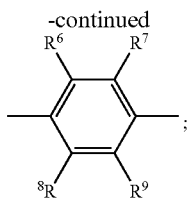

$R^1$ and $R^2$, which may be same or different, are independently hydrogen, $C_1$-$C_{24}$ alkyl, $C_1$-$C_{24}$ alkylhydroxy, halogenated $C_1$-$C_{24}$ alkyl, aryl, $C_1$-$C_{24}$ arylalkyl, $C_1$-$C_{24}$ alkylaryl, $C_1$-$C_8$ alkoxy, bromo, chloro, fluoro, iodo, $C_1$-$C_{24}$ alkylcarboxy or hydroxy;

$R^3$ is independently $C_1$-$C_{30}$ alkyl, $C_1$-$C_{30}$ alkylhydroxy, aryl, $C_1$-$C_{30}$ alkylaryl or $C_1$-$C_6$ alkoxy;

$R^4$ and $R^5$ are independently hydrogen, $C_1$-$C_6$ alkyl or $C_1$-$C_6$ alkylhydroxy;

$R^6$, $R^7$, $R^8$ and $R^9$ are independently hydrogen, $C_1$-$C_3$ alkyl, $C_1$-$C_3$ halogenated alkyl, fluoro, chloro, bromo and iodo;

$R_q$ is a quaternizing substituent selected from the group consisting of alkyl, alkoxy, arylalkyl, alkylaryl, fluoro, bromo, chloro, acetoxy, alkylacetoxy, arylacetoxy, carboxy, alkylcarboxy, hydroxy, and alkoxyhydroxy. For these preferred embodiments, a, denotes the positive charge of the structural unit (A), ranges from 0 to 10;

p, may be same or different for D, E, B, and F, independently ranges from 1 to 40;

v, may be same or different for E, B, and F, independently ranges from 1 to 40;

f, may be same or different for E, B, and D, independently ranges from 1 to 10;

g, may be same or different for E, B, and D, independently ranges from 1 to 10; and k is 0 or 1.

Similarly, the formula (B) shows alkoxylated oligoesters which are preferred embodiments of those in formula II

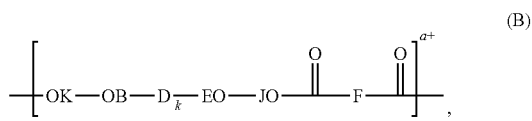

where all of the groups are as defined in connection with formula (A) except that —OK and JO—, which may be same or different, are alkoxy spacers having m units of the structure

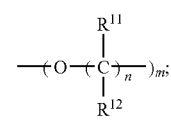

n is ranging from 1 to 6;

m is ranging from 1 to 300.

Both of these may be quaternized and associated with an appropriate number of counter ions.

In one preferred embodiment, the invention provides products of a reaction between a diol or a protected diol

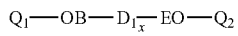

and a diacid or a protected diacid

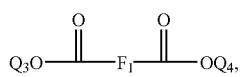

or a reactive carboxy compound

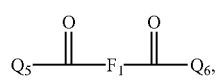

where $Q_1$ and $Q_2$, which may be same or different, are preferably hydrogen or a reactive hydroxy-protecting group, $Q_5$ and $Q_6$, which may be same or different are preferably hydrogen, an alkyl group or a reactive carboxy-protecting group, $Q_3$ and $Q_4$ are preferably halide, including chloride and bromide B, E, O and X are defined above with reference to formulae (I) and (II). $D_1$ may be same as D as defined above, or different so that $D_1$ may be converted to D via derivatization of the reaction products above. $F_1$ may be same as F that is defined above, or different so that $F_1$ may be converted to F via derivatization of the reaction products.

The examples of the reaction(s) products include oligoesters such as

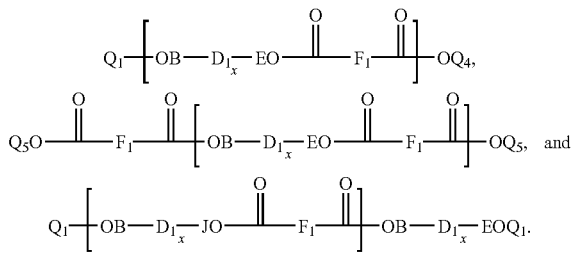

In another preferred embodiment, the invention provides products of a reaction between an alkoxylated diol or a protected alkoxylated diol

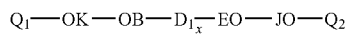

and a diacid or protected diacid

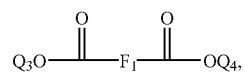

or a reactive carboxy compound

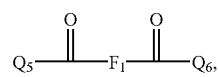

where $Q_1$, $Q_2$, $Q_3$, $Q_4$, $Q_5$, $Q_6$, B, E, K, J, O, $D_1$, $F_1$, and X are defined above The examples of the reaction(s) products include alkoxylated oligoesters such as:

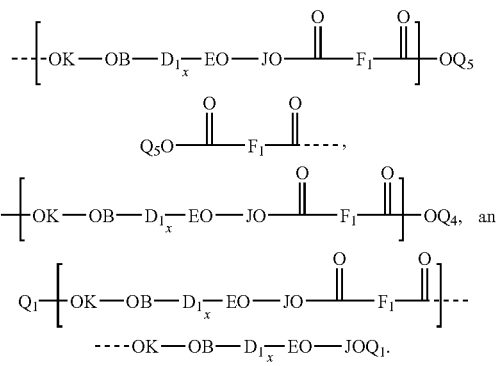

Note that it may be desirable to have oligoesters that terminate only in diol fragments, both diol fragments and diacid fragments or only diacid fragments. The resulting oligoesters may be then derivatized and/or deprotected as previously discussed.

These protecting groups can also be groups that prevent further chain propagation such as end caps. Assuming for illustration, that an oligoester was composed of diacid fragments and diol (or alkoxylated diol) fragments, and referring to formulae (I) and (II), if the oligoester terminates in two diacid fragments, the end caps used could both be G and if both were alcohols, the end caps could both be A. End cap G is H, OH, $R_6$ or $OR_6$ and end cap A is H, or $R_7$. Thus, when A and/or G are not hydrogen or alkyl, then A is a carboxyl terminating group and G terminates in an alcohol. $R_6$ and $R_7$ are independently a capping or end cap group that are preferably hydrophobic in nature including substituted or unsubstituted fatty alcohols and fatty acids having between 4 and 36 carbons including, for example, behenic, erucic, capric, oleic, linoleic, isostearic, ricinoleic and derivatives thereof such as 12-hydroxystearates and polyricinoleates including those having the structures:

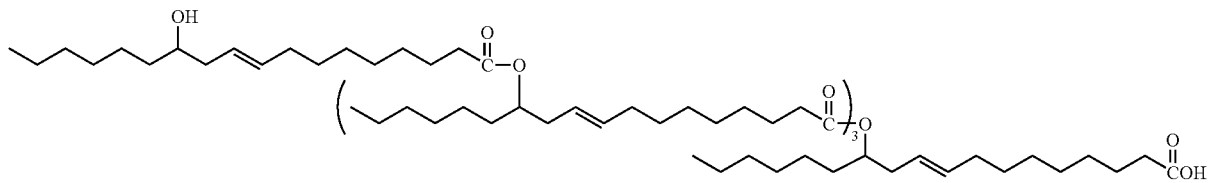

and:

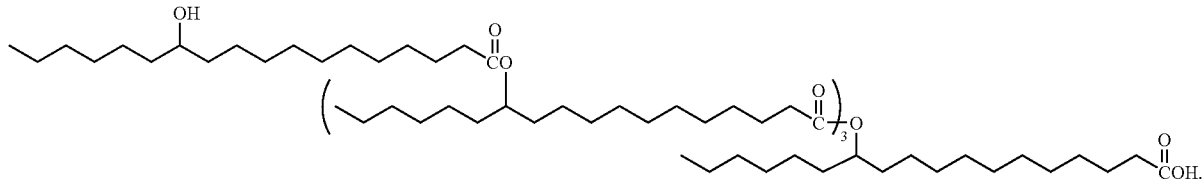

$R_6$ and $R_7$ may also be $R_1$, a diglyceride having fatty acid groups of an many as 36 carbons as exemplified above and may be, fatty acid or alcohol derivatives of pentaerythritol and the like. A and G may also have the structure:

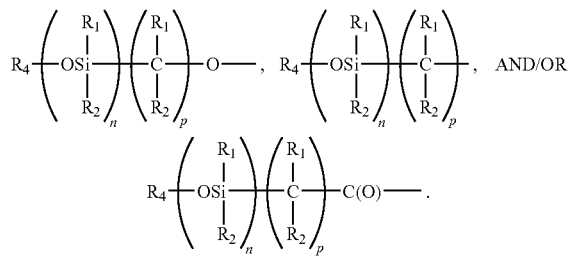

The number of diol fragments and diacid fragments in the backbone of each oligoester in accordance with the present invention is variable and depends on a number of factors. Amongst these factors are the desired properties of the finished composition of matter, such as polarity, viscosity and the like, the degree and type of substitution(s), the type of end caps used, whether the composition will include quat groups and how may quat groups are desired, the end use (will the backbone be used in a conditioner), etc. In general, however, there will be at least two diol fragments and two diacid fragments, although there could be as many as 50 of one and 51 of the other. Each fragment may be the same or different.

It is possible to alkoxylate some but not all of the diols used in the backbone. For example, some structural units of Formula I could be reacted with some structural units of Formula II. Indeed, they could be reacted in blocks or alternating patterns. Similarly, when making a backbone in accordance with the present invention, a co-condensation reaction between, for example, a diol and an alkoxylated diol with a diacid (e.g., the co-condensation may involve one mole of the diol, one mole of the alkoxylated diol and two moles of the diacid) to yield a mixture of oligoesters with the backbones that include fragments —OB-$D_X$-EO—, OK—OB-$D_X$-EO—, —OB-$D_X$-EO-JO, and OK—OB-$D_X$-EO-JO. These fragments could be distributed in the backbone randomly, in blocks or in other manner. It is also possible to alkoxylate only one, but not both, OH groups of the diol and use same in the oligoesters of the invention. Also, transesterification reactions between different oligoesters are possible.

In addition, more than one type of alkoxy group, and more than one of the same group may be placed between successive ester carboxylic group and an oxygen attached to the groups E and/or B in the backbone. For example, a portion of the backbone of an oligoester of the present invention between the oxygen attached to the groups E and B and the adjacent carboxyl group of the ester could have the structure of: —$CH_2$O—[alkoxy A]$_5$-[alkoxy B]-[alkoxy C]-[alkoxy B]$_3$O—CO—. In this example, for each diol (except if the backbone terminates at a diol fragment) ten units of alkoxy A, eight units of alkoxy B and two units of alkoxy C will be present.

$R_{10}$ is a group conventionally used to form quaternary amines or "Quats." Quaternizing groups, include, but are not limited to alkyl, alkoxy, arylalkyl, alkylaryl, halogen, including bromo and chloro, acetoxy, alkylacetoxy, arylacetoxy, carboxy, alkylcarboxy, hydroxy, and alkoxyhydroxy. These groups can include benzyl-, delta-gluconolactone derivates (useful moisturizers) or antioxidant-derived substituents. Indeed, $R_{10}$ can be any group useful for addition to, in particular, secondary and more preferably tertiary nitrogen or to another heteroatom. These can include the use of peroxide to produce amine oxides, acetic acid chloride, the reaction product of epichlorohydrine and a bisulfite, a siloxane, which includes an epoxy group and the like. Indeed, $R_{10}$ may be a bridging molecule or spacer that can be attached to a nitrogen and which contains or is susceptible to the action of a second compound including a group such as an epoxy or halogen such that the bridge can join the now quaternary nitrogen to an extended group. This process is illustrated by the production of polyquaternium 59 in Example 3. The epichlorohydrine forms a bridge between the oligoester backbone and cinnamidopropyl dimethylamine.

$R_{10}$ may include groups designated as $R_{UV}$ which is a UV-active moiety or UV-protecting group. A group of atoms or a portion of a molecule qualifies as a UV-active moiety if such group of atoms or portion of a molecule is capable of absorbing or blocking electromagnetic waves in ultraviolet region of electromagnetic spectra. For example, $R_{UV}$ may be any organic moiety that possesses quantized levels of molecular energy suitable for excitation in the UV spectral region. Also, chemical compounds that contain such organic moieties, for example, may be observed in the dark upon irradiation of such compounds by UV radiation. Especially useful moieties absorb electromagnetic radiation in UVA and/or UVB spectral regions.

Oligoester quats of the present invention are useful in cosmetics and personal care products, especially in hair care and sun protection products. The use of UV-active $R_{UV}$ in the ester-containing oligoesters of the invention may improve sun protection performance of these compounds in various cosmetic and personal care products. These compounds combine traditional hair conditioning properties of quaternary compounds, such as combing and softness improvements, with UV-absorbing and/or blocking properties useful in protecting hair and skin from sun damage, good hair and skin adhesion, and hair styling benefits. While the invention is not bound by any specific theory, it is thought that conditioning and adhesion performance of this quats is related to the presence of positively charged nitrogen atom, the sun-protection performance results from the presence of the $R_{UV}$ groups, and hair styling benefits are obtained because of the polymeric character of this compounds. For these reasons, oligoester quats of the invention of the invention are especially useful in hair conditioners and conditioning shampoos that include sun protection ingredients. In such products, these compounds may be used as the only sun protection component. Likewise, any of the compounds of the invention may be used in combination with one or more additional sunscreen agents, ingredients, or components, both conventional and otherwise.

In contrast to many known sunscreen agents, the oligoester quats of the invention as well as many of the other oligoesters of the invention, have good adhesion to hair, and thus remain on the hair to performing its sunscreen function. At the same time, these compounds may still be used as active hair conditioning ingredients in products and formulations that are not intended for sun protection purposes.

Preferably, the UV-active moiety $R_{UV}$ and $R_{10}$ include groups of atoms or portion(s) of a molecule that has/have multiple bonds (e.g., double and/or triple bonds) and/or aromatic systems, both conjugated and non-conjugated in various combinations. Preferred examples include aminobenzoate system

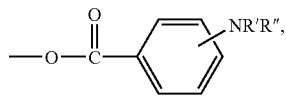

where examples of R' and R'' include hydrogen, methyl, methoxy, ethyl, and other groups known to as part of the aminobenzoate system in conventional UV-absorbing compounds, and —NR'R' is preferably in para position, and cinnamate system

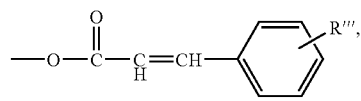

where examples of R''' include hydrogen, methyl, methoxy, and other groups known to as part of the cinnamate system in conventional UV-absorbing compounds. Particularly preferred examples include para-aminobenzoate system

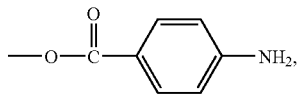

and cinnamate system

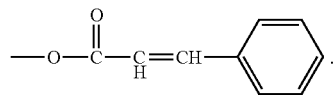

These groups of atoms are arranged in a manner that provides conjugated multiple bonds and aromatic ring. While the invention is not limited to any particular theory, it is believed that such conjugation may contribute UV absorption/blocking ability.

Preferably, the UV-active moiety $R_{UV}$ includes a group or groups derived from compounds suitable for use as sun protection ingredients in cosmetic and/or personal care products.

Non-limiting examples of such compounds include para-aminobenzoic acid (PABA), dimethyl PABA, benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid.

Note that formulations in accordance with the present invention may include an oligoester quat wherein $R_{10}$ is derived from a UV-active compound as defined herein mixed with: other oligoester quats of the present invention; other oligoester quat wherein $R_{10}$ is derived from a UV-active compound as defined herein; and/or UV-active compounds as identified herein. $R_{10}$ may be different for different quats of a mixture or may differ from one structural unit to the next, allowing for tailoring of UV-protecting properties. These UV-active compounds include, without limitation, the compounds mentioned above as well as the sunscreen agents and the cinnamido alkyl amino quaternary components of the sunscreen compositions described in U.S. Pat. No. 6,190,645, the text of which is hereby incorporated by reference. Thus a sunscreen product in accordance with the present invention could be produced from, for example, an oligoester quat made using a cinnamido alkyl amino quaternary group in producing the quat portion and the identical cinnamido alkyl amino quaternary compound which is not reacted to the oligoester backbone, as well as other UV-active compounds.

When the oligoesters in accordance with the present invention are quats or other charged species (such as protonated nitrogen groups), there is generally a counter ion associated with each ionic species. In terms of quats, the counter ion will be a anions. Anionic counter ions, include but are not limited to chloride, bromide, iodide, fluoride, sulfate, methyl sulfate, methanebenzylsulfonate, phosphate, nitrite, nitrate, carboxylate, or a mixture thereof. Fatty acids may also be used as counter ions. Chloride, methyl sulfate or mixtures of chloride and methyl sulfate are preferred.

For illustrative purposes only, consider the following additional figures. Formula IV illustrates generic formula which further illustrates in the relationship between groups OB, D, EO, the diacid group including group F, end caps A and G and alkoxy groups OK and JO. Formula V shows the same compound with specific substitutions for each such group.

For illustrative purposes, consider the following structures each of which share a common oligoester backbone in accordance with Formulas I or II:

IV

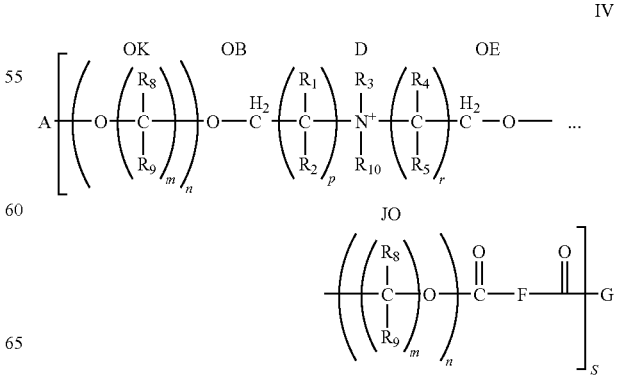

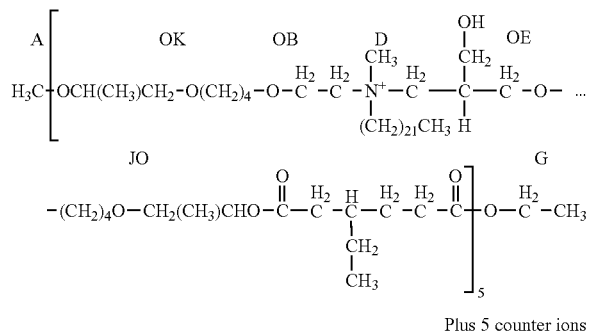

Plus 5 counter ions

Formulas IV and V have a backbone with the structure of Formula II. In Formula V, A is $CH_3$, the alkoxy groups OK and JO are each —$OCH(CH_3)CH_2$—$O(CH_2)_4$—. In this formula, n, analogous to nn defined previously, is 2, m is 2 for the first alkoxy group and 4 for the second alkoxy group. $R_8$ and $R_9$ are each H except that one $R_8$ in the first alkoxy unit is —$CH_3$. OB and OE are each —$OCH_2$—, D is $CH_2N^+CH_3((CH_2)_{21}CH_3)$—$CH_2CHCH_2OH$—. X is 1, p is 1 and both $R_1$ and $R_2$ are H. $R_3$ is —$CH_3$, $R_{10}$ is —$(CH_2)_{21}$—$CH_3$. r is 2 and in the first instance, $R_4$ and $R_5$ are all H. In the second instance, $R_4$ is H and $R_5$ is —$CH_2OH$. F is —$CH_2CH(C_2H_5)$—$C_2H_4$—. G is —$OCH_2CH_3$.

As described above, the oligoesters of the invention and in particular, the backbones, are preferably produced by a reaction between a diol and a diacid, diester, anhydride or diacid halide. It should be understood that specific oligoester compounds produced by such reactions are within the scope of the invention, whether such compounds are in fact produced via such reactions or in any other ways. However, such condensation reactions may produce oligomeric mixtures of oligoesters having a given average molecular weight and molecular weight distribution (Mw/Mn). Both narrow and wide molecular weight distribution could be produced. It should be understood that the properties of the oligoesters in accordance with the present invention can depend on the nature of the mixture, if any. It will be understood that the properties of such mixtures and the pharmaceutical, personal care and cosmetic products made using same can be modified not only by the selection of a specific oligoester, but also by the selection of certain mixtures of oligoesters or modification of the amount of selected oligoesters in a mixture. When used herein, a reference to a particular oligoester contemplates not only that compound, but also mixtures, including those having a desired molecular weight and/or molecular weight distribution. Various fraction of the oligoester may be separated and/or purified if desired and used separately. Any separation/purification methodology may be used.

Control over the average molecular weight and the molecular weight distribution may be exercised by any methods known in the art of polymerization, including methods described in various articles, patents and other publication materials enclosed as part of this application and incorporated by reference herein. Thus, after the initial condensation reaction, the reaction mixture may be re-heated and/or heated under vacuum to provide oligoesters of higher molecular weight. Also, successive addition of carboxy- and hydroxy-terminated compounds may extend the length of the chain. Also, the backbones of may be combined after they are prepared in a successive condensation reaction. Backbones having same of different repeating units may be used and connected in this way.

Returning to the issue of mixtures, it will be appreciated that it may be possible to produce relatively pure oligoesters or oligoesters with relatively few oligoester contaminants by various known techniques. For example, presume that one is interested in producing an oligoester of the structure [DA]-[DA]-[DA]-[DA]-D where D" refers to a diol and "A" refers to a diacid. This particular oligoester would include four structural units, each indicated by the square brackets and an additional diol such that the oligoester ends in hydroxy groups or hydroxy functionality. This oligoester could be produced by reacting two moles of a diacid with one mole of a diol to produce a molecule having a structure ADA. In essence, since this molecule ends in acid functional groups on both ends, one mole of this material could be reacted with two additional moles of diol to produce the molecule DADAD. The stoiciometric excess of D added, and the absence of other likely reaction sites suggests a relatively higher proportion of the desired product would be produced. This molecule is essentially a diol. One mole of this diol could then be reacted with two moles of diacid, producing the structure ADADADA. One mole of this diacid could then be reacted with two moles of diol to produce the final desired structure. The predominant oligoester, e.g. the oligoester which, of all of the oligoesters produced in the mixture, is present in the highest proportion, should be that which has the desired number of structural units (4 in this example).

For relatively shorter molecules, or molecules that require generally higher levels of homogeneity or purity, such procedures may be useful and desirable. However, they may be impractical for large scale commercial applications and, in particular, for the production of much larger oligoesters. In general, to produce the above oligoester, since five diol fragments are desired and four acid fragments are desired, one would divide five by four and determine that 1.25 moles of diol is necessary for each mole of diacid used. These would all be supplied to a common reactor and the reaction would go largely to a predictable endpoint. The result would be a mixture of oligoesters of varying size. The chain length desired, in this case, four structural units and an additional diol fragment, will determine the molar ratio of materials to be utilized and that in turn will translate into determining the size of the finished oligoester. There are many other methods known which can be employed to produce oligoesters that rely on this concept. In addition, by adjusting the solvents, temperatures, the use of catalysts and other known devices, the efficiency of conversion can be improved. This would reduce the number of oligoesters in the mixture or increase the proportion of the oligoester of desired length and structure.

It may also be possible to create oligoesters by producing smaller subunits such as the one described above and then by selectively protecting these oligoesters, they can be coupled to other oligoesters, of the same or different structure, size and composition, to produce more extended chains. It may also be possible to produce hydroxy terminated oligoesters and then further react them with a dicarboxylic acid under the conditions described above. The reverse is also possible where a carboxy terminated oligoester is further reacted with a diol.

For purposes of the present invention, it will be appreciated that when one refers to a particular oligoester having a particular backbone structure, for example, they are referring to that specific structure, whether it is pure or as part of a mixture. It will be understood, however, that in most instances, the production of an oligoester in accordance with the present invention will produce a mixture, unless the results are purified. In such mixtures, the structure of the predominant fraction will generally control its naming. FIG. 1 is a chromatogram from a gel permeation separation of a mixture produced in accordance with Example 2. 500 and 1,000 angstroms pore size styrene-divinylbenzene GPC columns (300×7.8 mm, 5 µM) were used with tetrahydrofuran (THF) as the mobile phase run at 1 mL per minute. Detection was by refractive index and calibration was conducted first by polyethylene oxide standards. The chromatogram shows a maximum indicated as 2,845. This number, along with the weight average molecular weight, ($M_w$=2703) agreed well with the determination by wet analysis as exemplified by the hydroxyl value of 41. These numbers all suggested a structure where the predominant fraction, and therefore the single most abundant oligoester, was the compound titled in Example 2, namely, PPG-4-N-methyl-N, N-diethanolamine adipate oligomer, consisting of four structural units and an additional oxylated diol.

This was the compound that was desired and the proportions of the starting materials used were predicated on the hope of producing the titled compound. Thus, one can, using routine techniques such as calculation of the hydroxyl value based on the standard USP method and the use of gel permeation chromatography, confirm that the desired number of structural units, chain length, molecular weight, etc. has been achieved by the predominant oligoester in the mixture.

Moreover, as a practical matter, especially where the oligoesters contain repeating structural units of the same basic structure, the properties of the predominant fraction may be very similar to those of oligoesters having one or two more, or one or two less, structural units. Certainly, when produced in accordance with the present invention, mixtures will contain not only a predominant fraction of a particular oligoester, but at least about 25%, preferably at least about 50% of all the oligoester species contained in the mixture will fall within plus or minus two structural units of the desired oligoester. For convenience, however, when a particular oligoester is used to identify a particular mixture, it is contemplated that it would be the predominant fraction, e.g. of all the oligoesters in the mixture, it would be present in the greatest amount.

Generally speaking, if an excess of the diol is used, the resulting backbone will be hydroxy-terminated. Likewise, the backbone will be carboxy-terminated if an excess of a diacid is used. It is believed that about 10-20 mole % excess of the desired diacid or diol is sufficient to consistently influence this outcome. If longer and/or higher molecular weight oligoesters are desired, equimolar amounts of the diacid and the diol is used, and the equimolar ratio is maintained in the course of the polymerization. Also, if shorter and/or lower molecular weight oligoesters are desired, the reaction may be quenched with an appropriate quenching agent before the condensation is complete. The suitable quenching agents include, but are not limited to, end-capping compounds.

Non-limiting examples of oligoesters include the following, referred to as "Backbone Oligoesters" to denote the fact that they are not derivatized:

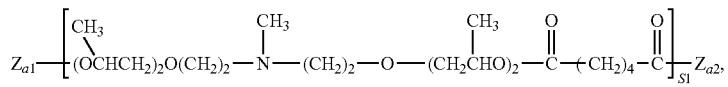

Backbone oligoester 1 which may be produced, for example, by condensation of alkoxylated diethanol methylamine with adipic acid or dimethyl adipate, where $Z_{a1}$ is hydrogen or

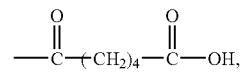

hydrogen, hydroxy or

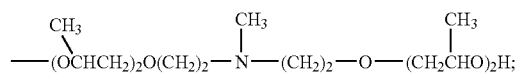

and S1 preferably varies from 2 to 20, more preferably, from 3 to 8. It is believed that under the reaction conditions described herein, the di-hydroxy-terminated oligoester 1 has an average S1 of 5.

Another non-limiting example of an oligoester is oligoester (2):

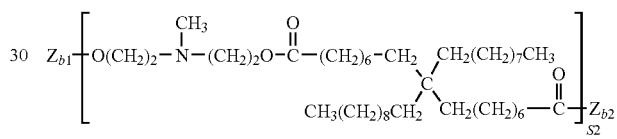

Backbone oligoester 2 which may be produced, for example, by condensation of diethanol methyl amine with a branched diacid of the formula

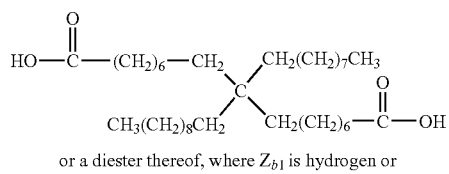

or a diester thereof, where $Z_{b1}$ is hydrogen or

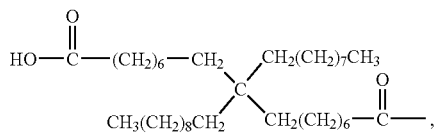

$Z_{b2}$ is hydrogen, hydroxy or

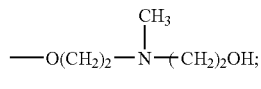

and S2 preferably varies from 2 to 20, more preferably, from 3 to 8. It is believed that under the reaction conditions described herein, the di-hydroxy-terminated oligoester 2 has an average S2 of 5.

Another non-limiting example of an oligoester is oligoester (3):

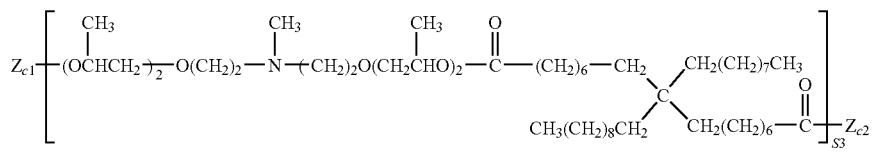

Backbone oligoester 3 which may be produced, for example, by condensation of alkoxylated diethanol methyl amine with the branched diacid or diester shown in reference to Backbone oligoester (2), where $z_{c1}$ is hydrogen or

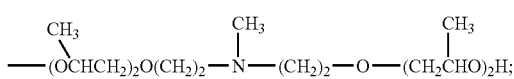

$Z_{c2}$ is hydrogen, hydroxy or

—(OCHCH$_2$)$_2$O(CH$_2$)$_2$—N(CH$_3$)—(CH$_2$)$_2$—O—(CH$_2$CHO(CH$_3$))$_2$H;

where S3 preferably varies from 2 to 20, more preferably, from 3 to 8. It is believed that under the reaction conditions

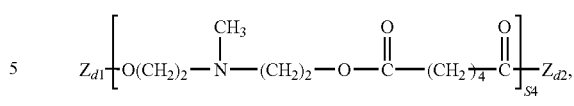

Backbone oligoester 4 which may be produced, for example, by condensation of diethanol methylamine with adipic acid or diester of the adipic acid, where $Z_{d1}$ is hydrogen or

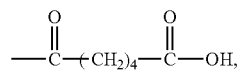

$Z_{d2}$ is hydrogen, hydroxy or

—O(CH$_2$)$_2$—N(CH$_3$)—(CH$_2$)$_2$OH;

and S4 preferably varies from 2 to 20, more preferably, from 3 to 8. It is believed that under the reaction conditions described herein, the di-hydroxy-terminated Backbone oligoester 4 has an average S4 of 5.

Other non-limiting examples of backbone oligoesters include

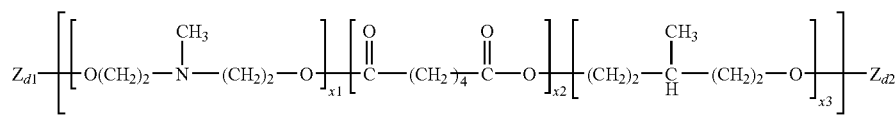

Backbone oligoester 5 described herein, the di-hydroxy-terminated Backbone oligoester 3 has an average S3 of 5.

Another non-limiting example of oligoesters is oligoester (4):

which may be produced, for example, by co-condensation of diethanol methyl amine and 3-methyl-pentane diol with adipic acid, where X1 may be from 1 to 10, x2 may be from 1 to 10, and x3 may be from 0 to 9;

Oligoester (6):

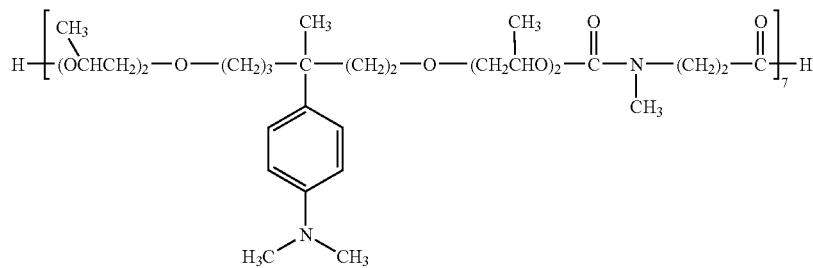

Backbone oligoester 6 which may be produced, for example, by equimolar condensation of a malonic acid methyl amine with 3-methyl-3-(p-dimethylaminobenzyl)-pentane diol;

Oligoester (7):

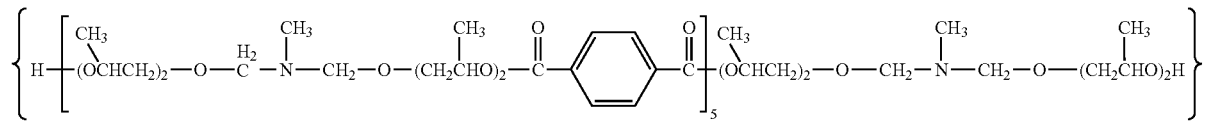

Backbone oligoester 7 which may be produced, for example, by a condensation of phtalic acid with an excess of alkoxylated dimethanol amine; and Oligoester (8):

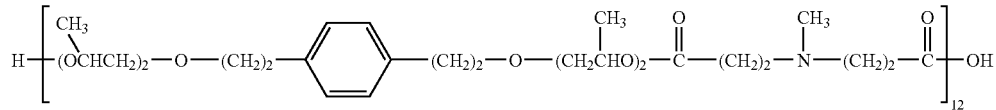

Backbone oligoester 8 which may be produced, for example, by equimolar condensation of propoxylated 1,6-diethyl benzyl diol with N-methyl-N',N''-bis-α-carboxyethyl amine.

The oligoesters may be derivatized, including a preferred quaternization, to provide derivatized oligoesters, including oligoesters quats. Non-limiting examples of the derivatized oligoesters of the formula I or II include the oligoester quats (1)-(6) illustrated below.

(1)

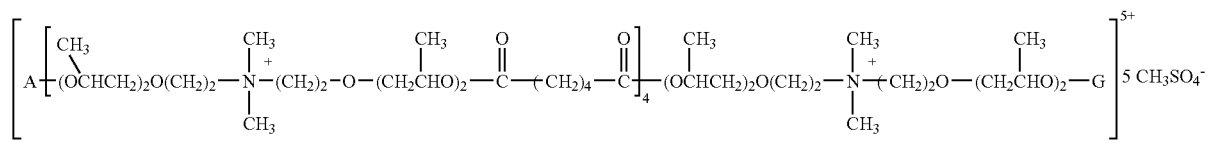

where A and G are groups derived from polyricinoleate and have the structure:

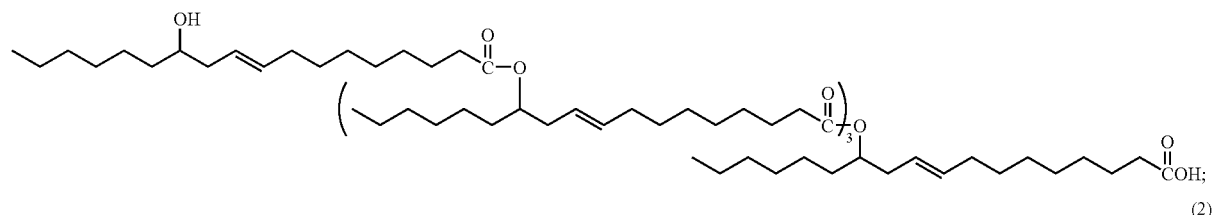
(2)
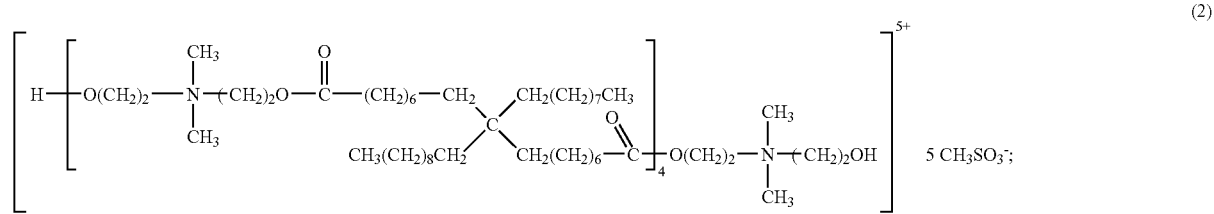
(3)
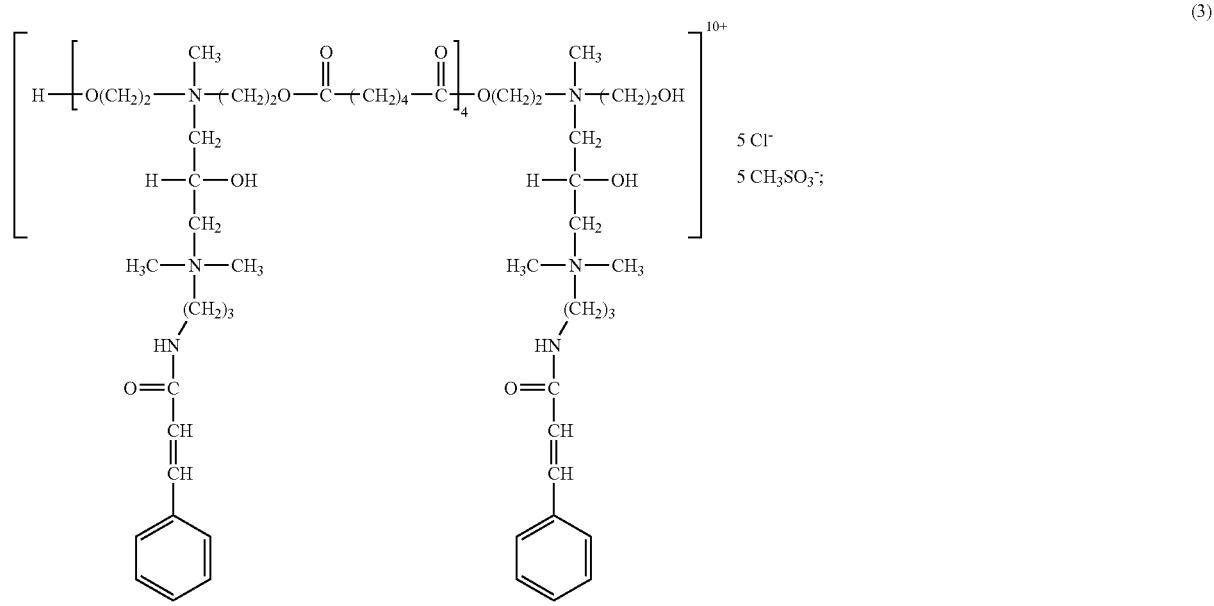
(4)
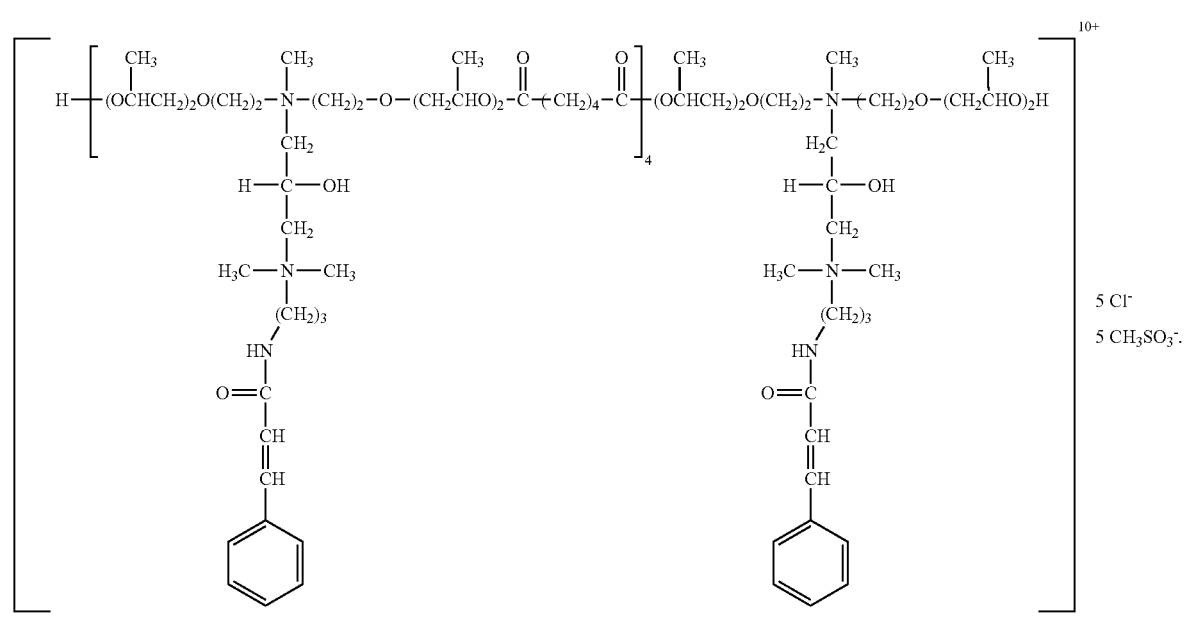

-continued
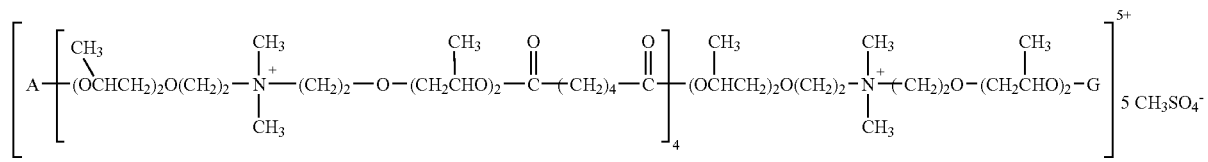
(5)
where A and G are groups derived from Poly 12-hydroxystearate having the structure:
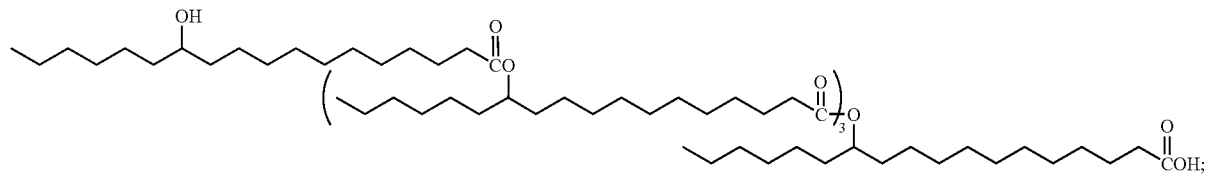
and
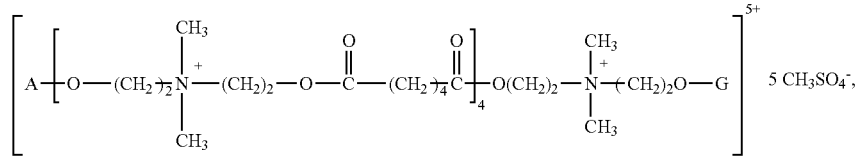
(6)
where A and G are the same as defined in reference to the compound (5).
Yet other examples of derivatized oligoesters having structures according to the formulae I or II include oligoesters (7)-(11):
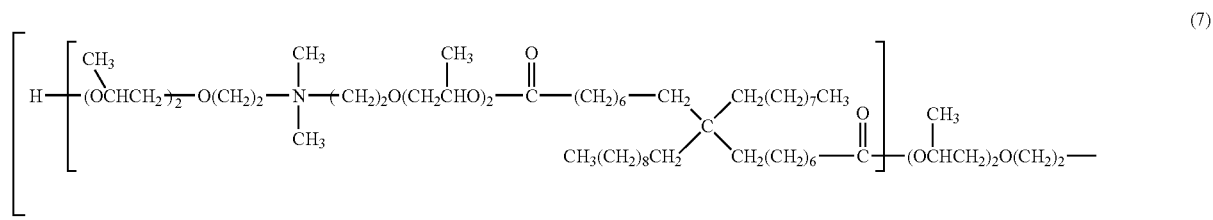
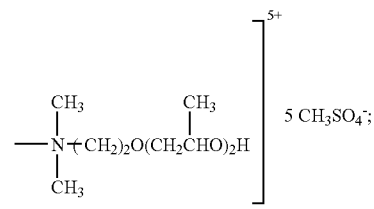
(7)

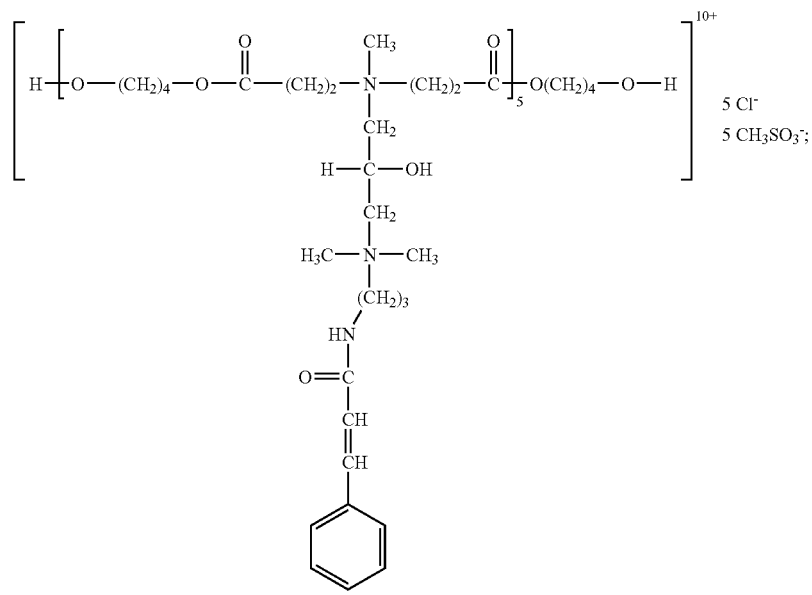
(8)
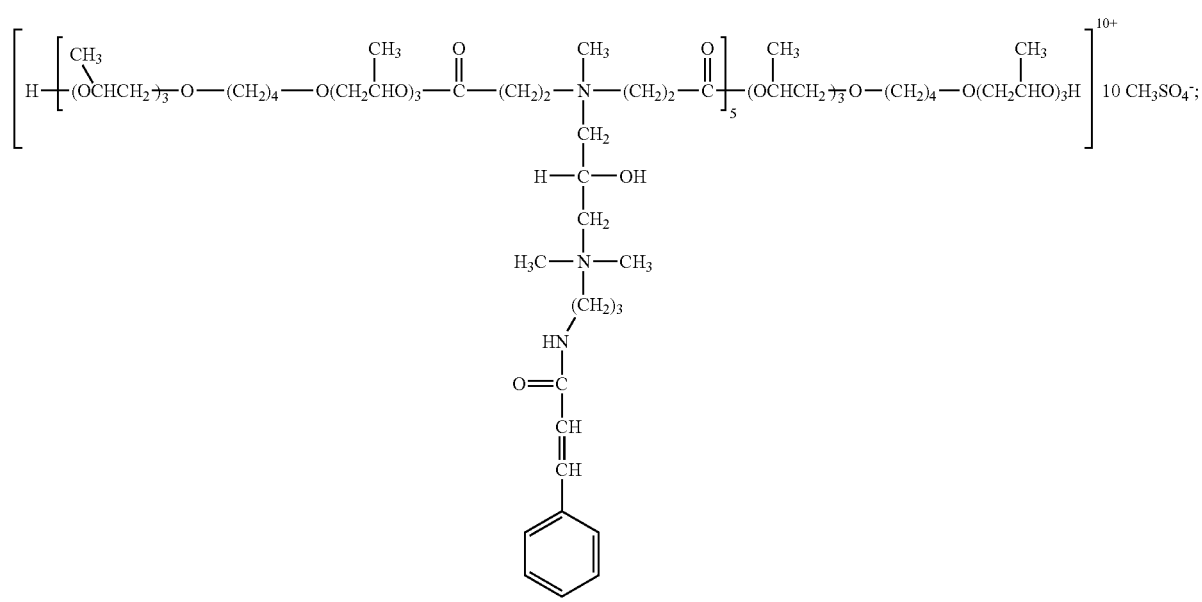
(9)

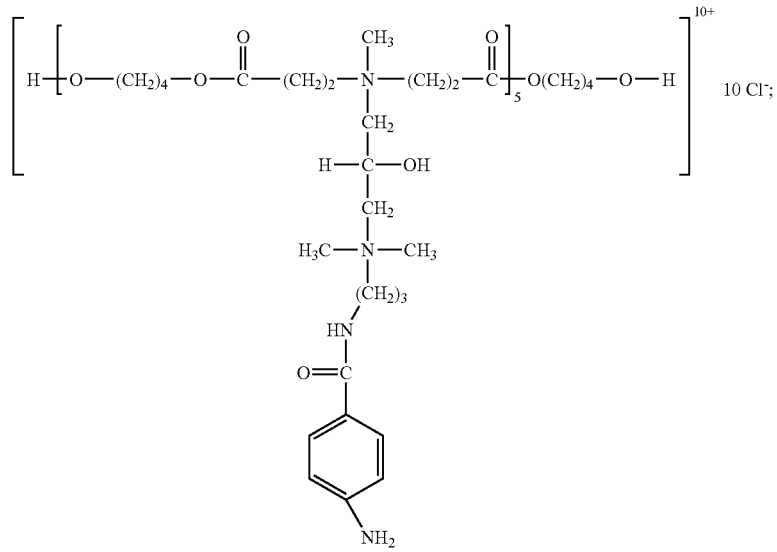
(10)
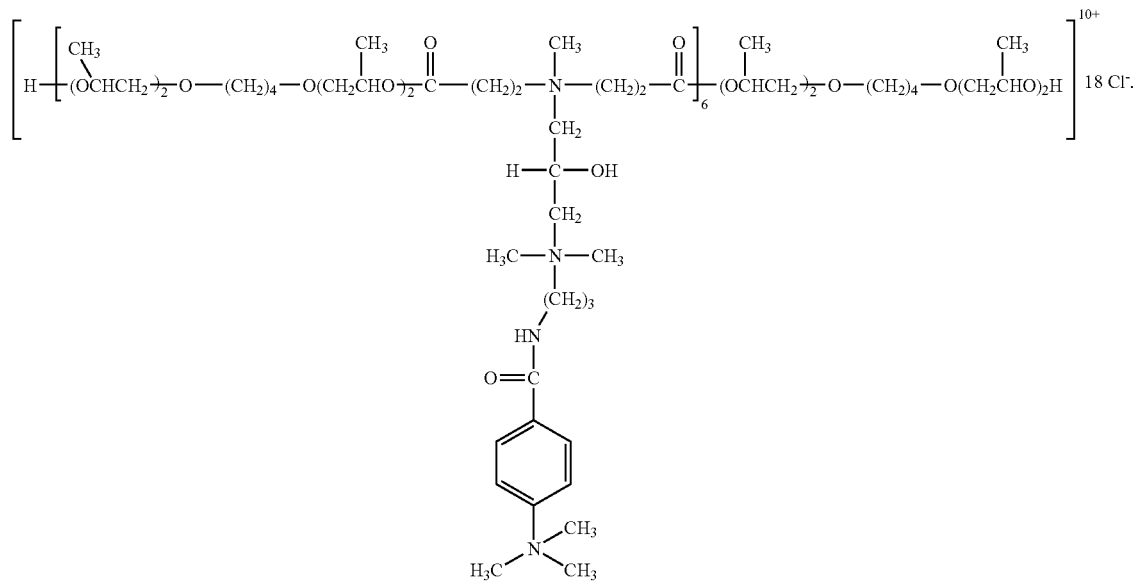
(11)
Yet other non-limiting examples of oligoesters according to the formulas (I) or (II) include compounds (12)-(18):
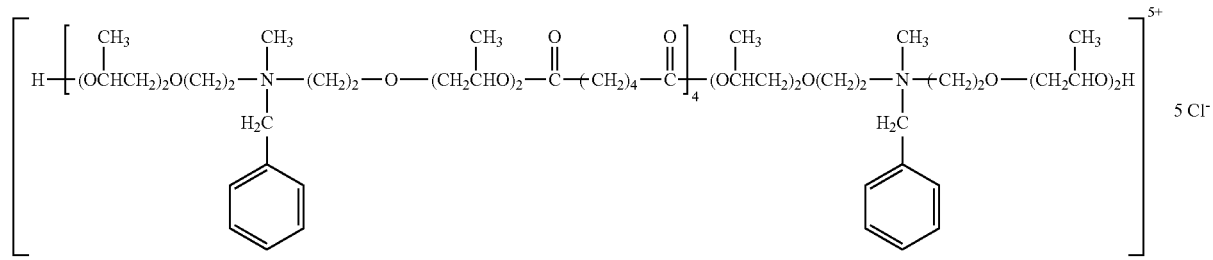
(12)

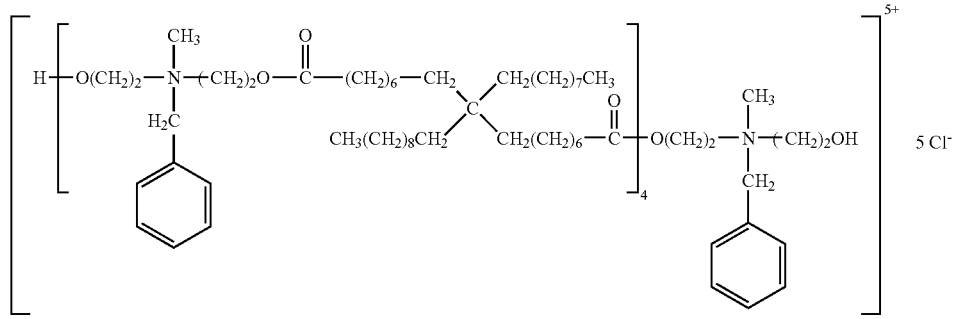
(13)
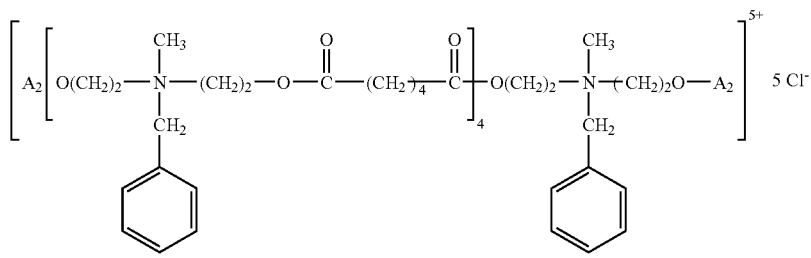
(14)
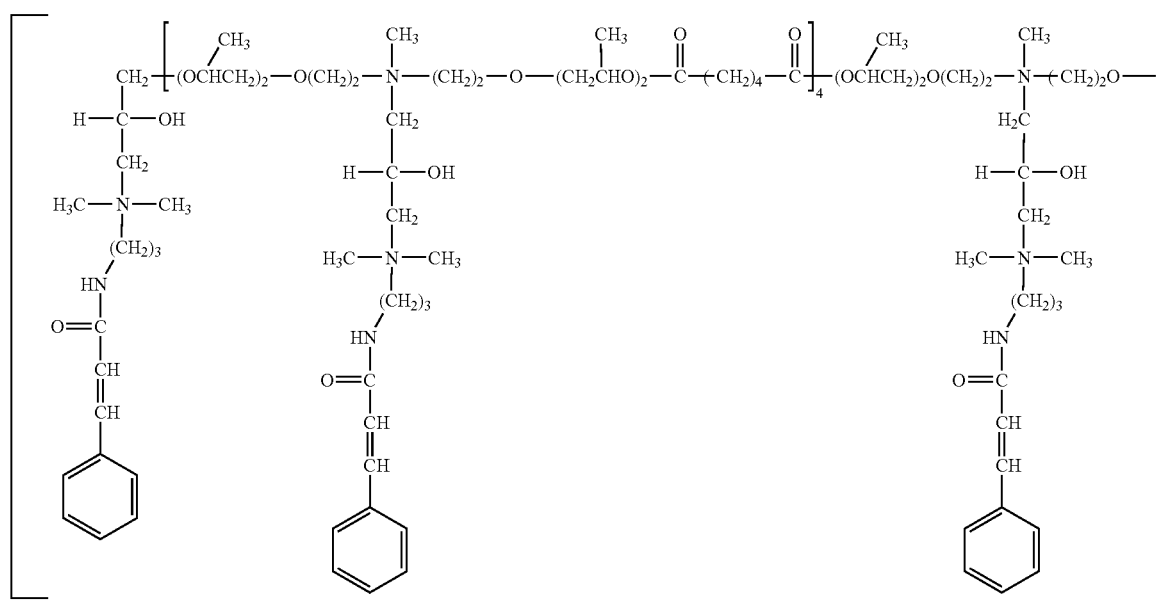
(15)

-continued
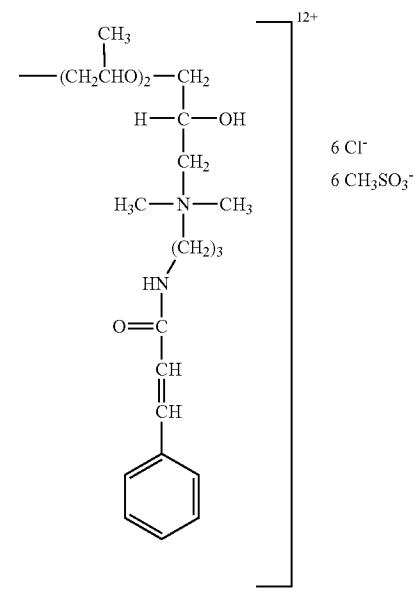
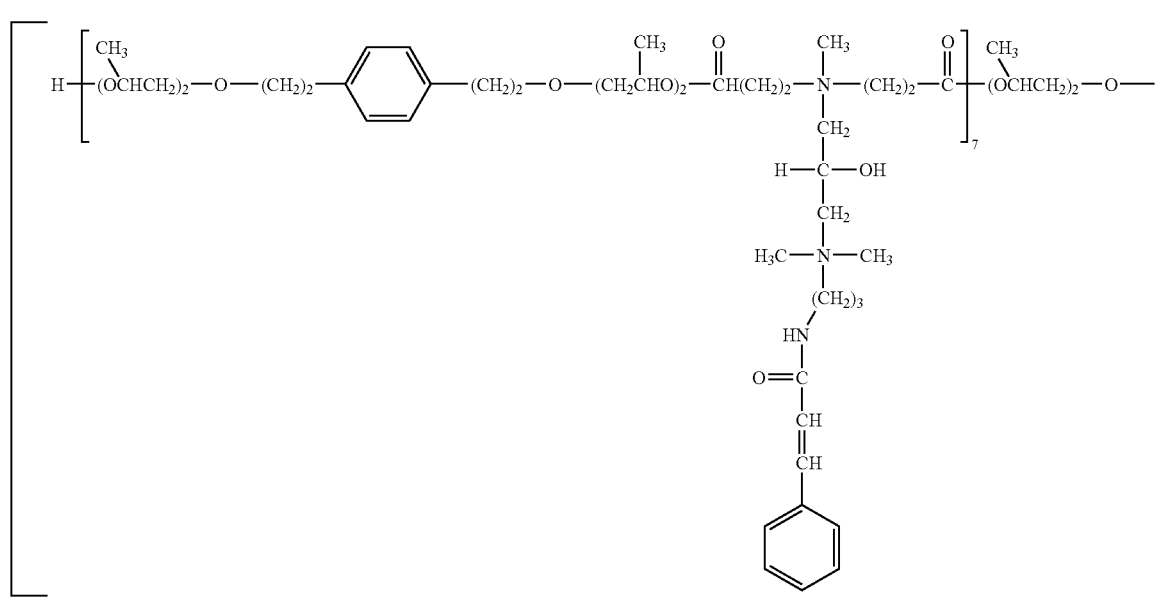
(16)

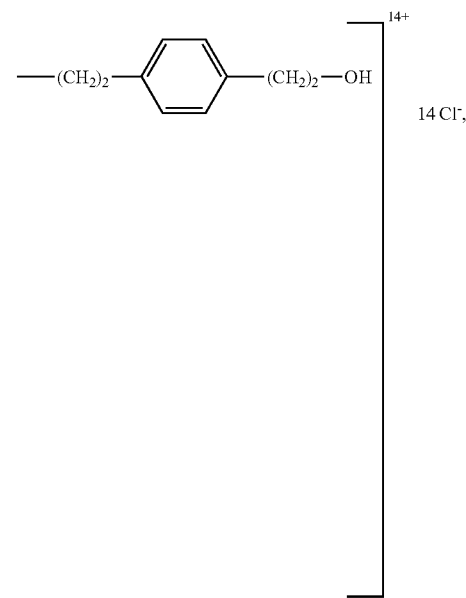
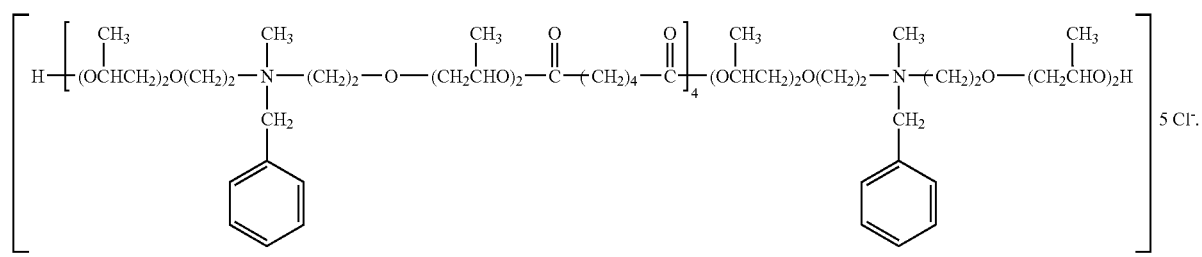
(17)
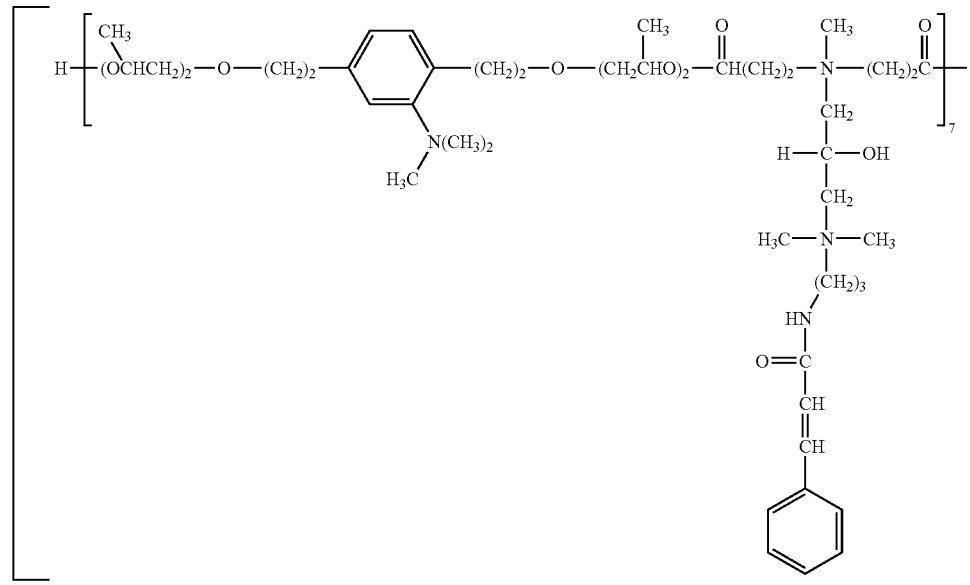
(18)

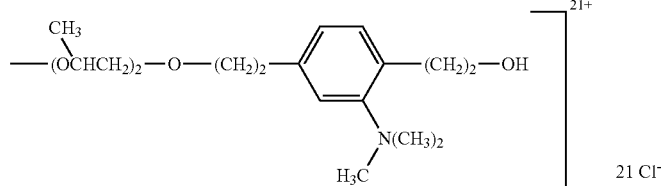

Some additional embodiments of oligoesters having UV-protecting groups attached to the nitrogen atoms in the backbone in accordance with the present invention are provided below. Note that the nomenclature for these embodiments has been altered to refer to superscripted R groups, m,n,x and z. These embodiments are intended to fall within the scope of those previously described in connection with formulas I and II above. To the extent that any of the definitions of any superscripted R groups, or other groups, illustrated in formulas VI-IX are broader than the corresponding groups in connection with formulas I-V, they should be considered together and are merely supplementary to one another.

In one embodiment, the invention provides one or more compounds of the formula (VI):

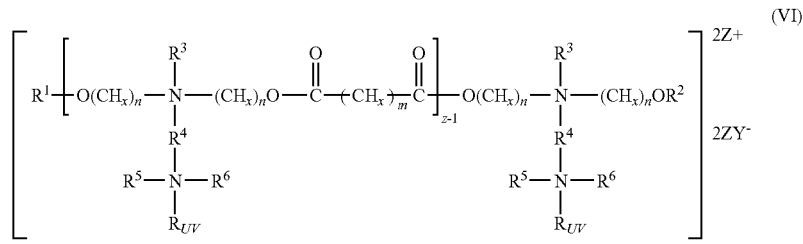

where $R^1$ and $R^2$, which may be same or different, are independently hydrogen, $C_1$-$C_{60}$ alkyl, a group of the structure

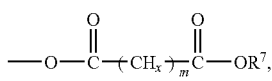

where $R^7$ is hydrogen or $C_1$-$C_{60}$ alkyl,
a group of the structure

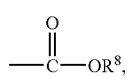

where $R^8$ is hydrogen or or $C_1$-$C_{60}$ alkyl;

$R^3$, $R^5$, and $R^6$ are independently $C_1$-$C_{20}$ alkyl, $C_1$-$C_{20}$ alkoxy, or hydrogen;

$R^4$ is a group of the structure

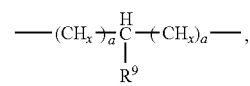

where $R^9$ is hydrogen, $C_1$-$C_{60}$ alkyl, —OH, $C_1$-$C_{20}$ alkoxy, or halide, including chloro and bromo;

$R_{UV}$ is the UV-active moiety described above in reference to moieties (A)-(D);

Y is a salt-forming anion, such as chloride, bromide, iodide, fluoride, sulfate, methyl sulfate, methanebenzylsulfonate, phosphate, nitrite, nitrate, carboxylate, or a mixture thereof, preferably, chloride, methyl sulfate or mixture of chloride and methyl sulfate;

—$(CH_x)_n$—, —$(CH_x)_m$— and —$(CH_x)_a$— are alkyl or alkylene groups, straight chain or branched, saturated or unsaturated, in which preferably, x may vary from 1 to 2 or may be 0 if m or n is 2 or more, preferably, n may vary from 1 to 10, preferably, from 1 to 3, more preferably, n is 2, preferably, m may vary from 1 to 10; preferably, from 2 to 8; more preferably, m is 4;

preferably, a may vary from 0 to 10, preferably, from 1 to 5; more preferably, a is 1;

preferably, z may vary from 2 to 100, more preferably, z is 3-25.

Preferably, the UV-active moiety $R_{UV}$ has the structure

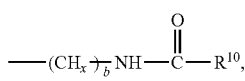

where $-(CH_x)_b-$ is an alkyl or alkylene group, straight chain or branched, saturated or unsaturated, in which b may vary from 1 to 10, preferably, from 1 to 5; more preferably, b is 3; $R^{10}$ is a substituted or unsubstituted, saturated or unsaturated group containing a 6-membered aromatic ring. More preferably, $-C(O)-R^{10}$ or $R^{10}$ is derived from a compound suitable for use as a sun protection ingredient in cosmetic and/or personal care products. Examples of such compounds include para-aminobenzoic acid (PABA), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid.

More preferably, $R^{10}$ has the structure

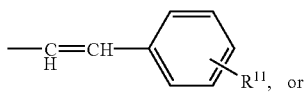

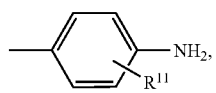

where $R^{11}$ is hydrogen, lower alkyl, halide or methoxy.

Preferably, $R^1$ and $R^2$ are independently hydrogen or the group

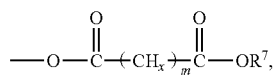

where $R^7$ is preferably hydrogen; more preferably, both $R^1$ and $R^2$ are hydrogen or both $R^1$ and $R^2$ are

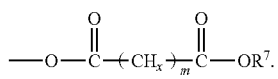

Preferably, $R^3$, $R^5$, and $R^6$ are $C_1$-$C_{20}$ alkyl, $C_1$-$C_{20}$ alkoxy, or hydrogen.

Preferably, $R^4$ is the group

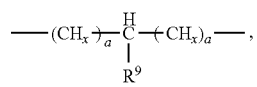

where $R^9$ is —OH, lower alkyl, hydrogen, halide or methoxy, x is 2, and a varies from 1 to 2; more preferably, $R^4$ has the structure

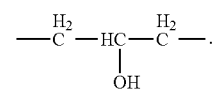

In the preferred compounds of the formula (VI), the moiety $R_{UV}$ is the cinnamido alkyl amino group of the structure

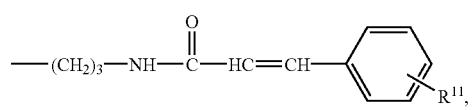

where $R^{11}$ is hydrogen, —NH$_2$, NO$_2$, CH$_3$O—, (CH$_3$)$_2$N—, or (C$_2$H$_5$)$_2$N—. More preferably, $R^{11}$ is hydrogen.

The more preferred compounds of the formula (VI) have the formula (VII):

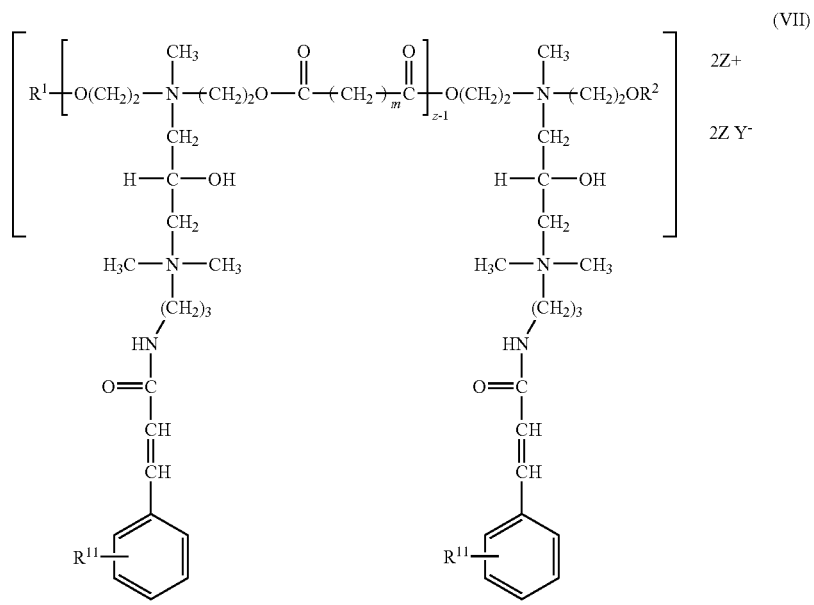

where $R^{11}$ is hydrogen or lower alkyl, m varies from 1 to 20, Y is methyl sulfate, chloride or mixture thereof, and z varies from 3 to 8.

In one preferred variant of the compounds of the formula (VII), $R^1$ and $R^2$ are both hydrogen. In another preferred variant, $R^1$ and $R^2$ are both groups with the structure

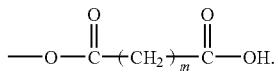

In yet another preferred variant, one of $R^1$ and $R^2$ is hydrogen, and another one of $R^1$ and $R^2$ is

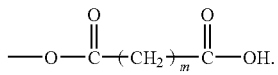

In another embodiment, the invention provides one or more compounds of the formula (VIII):

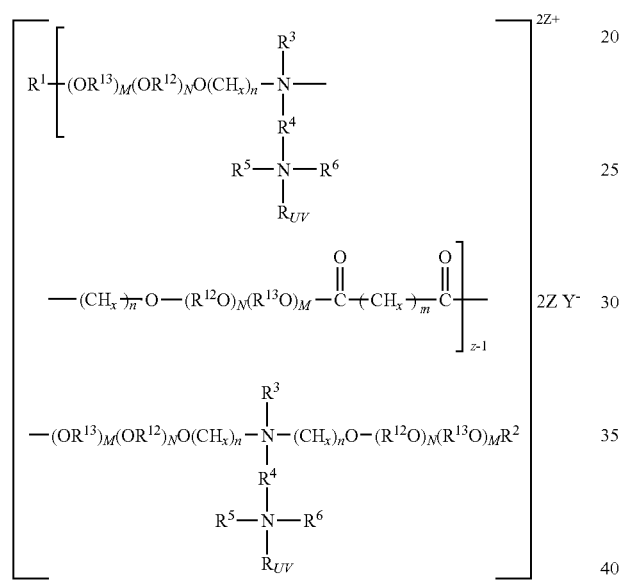

(VIII)

where $R^1, R^2, R^3, R^4, R^5, R^6, R^7, R^8, R^9, R^{10}, R^{11}$, and $R_{UV}$, $—(CH_x)_n—$, $—(CH_x)_m—$, $—(CH_x)_a—$, X, m, n, a, b, z, and Y are the same as described above with reference to formula (I);

$R^{12}$ and $R^{13}$, which may be same or different, are lower alkyl group having 1 to 6 carbon atoms, straight chain or branched, saturated or unsaturated, substituted or unsubstituted, preferably $R^{12}$ and $R^{13}$ are both the group $—CH(CH_3)CH_2—$;

the alkoxylated moieties $R^{12}O$ and $R^{13}O$ are present in any structural order to each other, and may thus be present randomly, in blocks, or in alternating patterns with each other;

more preferably, the alkoxylated moieties $R^{12}O$ and/or $R^{13}O$ each have the structure $[O(CH_2)_2—]$ or $[OCH(CH_3)CH_2—]$, where $[O(CH_2)_2—]$ is an ethoxy group and $[OCH(CH_3)CH_2—]$ is a propoxy group;

N ranges from 0 to 100, preferably, from 0 to 40, more preferably, from 0 to 3;

M ranges from 0 to 100, preferably, from 0 to 40, more preferably, from 0 to 3;

the sum of N and M ranges from 0 to 200, preferably, from 0 to 20, more preferably, from 0 to 10.

In the more preferred compounds of the formula (III), $R_{UV}$ is the cinnamido alkyl amino group of the structure

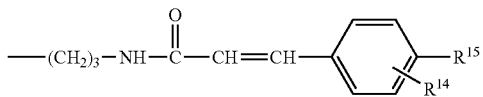

where $R^{14}$ and $R^{15}$, same or different, are independently hydrogen, $—NH_2$, $NO_2$, $CH_3O—$, or $(CH_3)_2N—$. Most preferably, $R^{14}$ and $R^{15}$ are both hydrogen.

Thus, the more preferred compounds of the formula (VIII) have the formula (IX):

(IX)

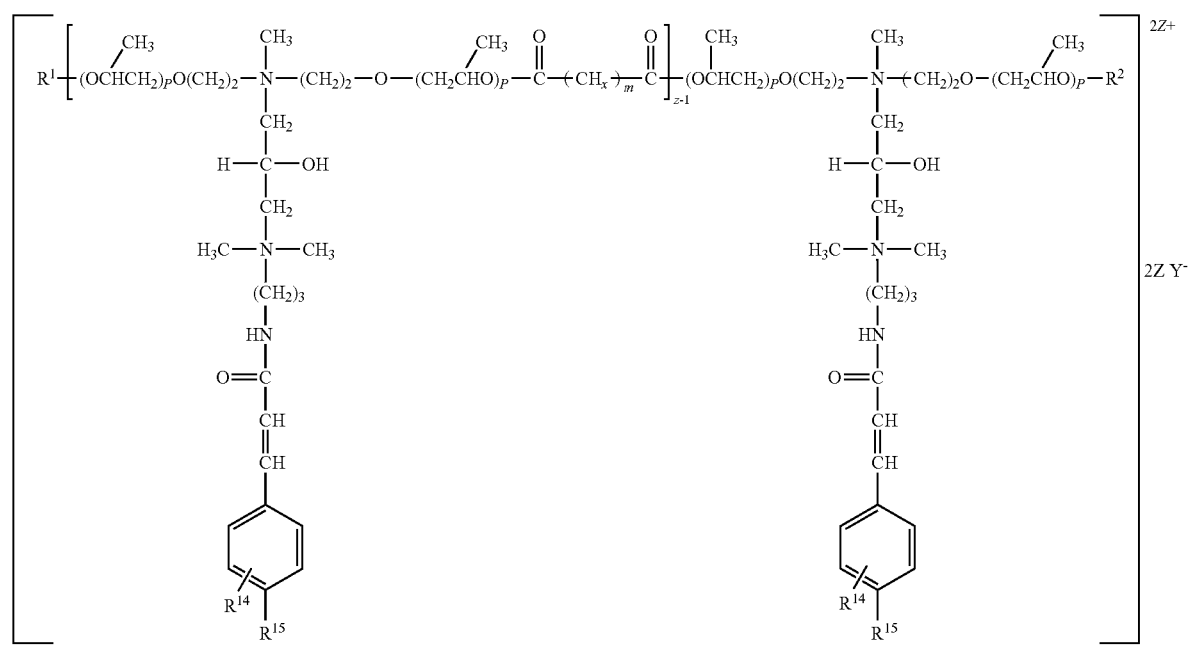

where $R^{14}$ and $R^{15}$ are as defined above, m varies from 1 to 5, Y is methyl sulfate, chloride or mixture thereof, and z varies from 4 to 6. In one preferred variant of the compounds of the formula (IX), $R^1$ and $R^2$ are both hydrogen. In another preferred variant, $R^1$ and $R^2$ are both groups with the structure

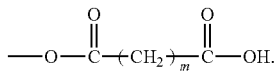

In yet another preferred variant, one of $R^1$ and $R^2$ is hydrogen, and another one of $R^1$ and $R^2$ is

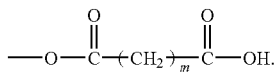

In a particularly preferred embodiment, the group $NR^4R^5R^6R_{uv}$ may be omitted or may be replaced by one or more of the groups identified and $R_{10}$ in connection with formulas I and II. $R^3$ ay be substituted with $R_3$ previously defined. These structures may be end capped with any of the groups described in this document which is capable of reaction with the appropriate terminal functionality at each end of the oligoester.

One of the advantages of the present invention is that the molecules of the formulae I and II, both alkoxylated and non-alkoxylated, may be made from very inexpensive and readily accessible starting materials and can be constructed using well-known reactions such as condensation reactions. This makes it easy to control costs and customize molecules for particular preparations or applications. Preparation may be carried out in accordance with any method known to those skilled in the art. One of the synthetic routes useful for preparation of these compounds will be illustrated using the preferred compound (3) as an example. It will be appreciated that a wide variety of products, including mixtures, might be obtained via this route by utilizing different starting materials and reagents.

To create the backbone of the oligoester (3), step 1A is a condensation reaction between di-ethanol methylamine and adipic acid:

STEP 1A

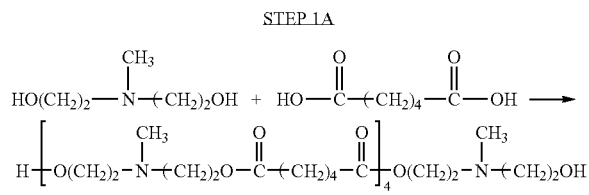

The condensation proceeds via esterification of hydroxy groups of di-ethanol methylamine by carboxylic groups of the adipic acid. Conventional catalysts can be used in this process and no solvents are required. Where solvents are used, they should include generally non-aqueous, non-polar organic solvents such as hexane, toluene, Xylene and the like. Water produced as a byproduct may be removed using, for example a Dean-Stark trap or using nitrogen sparge and condenser, particularly where no solvents are used. Vacuum can also be used to facilitate water removal. Reaction temperatures conventionally range between 150 and 220 degrees centigrade. Since both reactants are di-functional, the reaction leads to the formation of alternating backbone structures, which forms the backbone of the desired final oligomer. The backbone of Step 1A may be derivatized as desired and used in preparing other compounds. The choice of relative proportions of diethanol methylamine and adipic acid determines the terminal groups. Thus, in the presence of a sufficient excess of the adipic acid, the backbone oligomer (4) is carboxy-terminated. If hydroxy termination is desired (as shown above), the excess of di-ethanol methylamine is used instead.

Separately, the synthesis of the side chain or quaternizing group of the compound (3) may begin with a reaction between cinnamic acid and N,N'-dimethylamino-(n-propyl)-amine (Step 1B):

STEP 1B

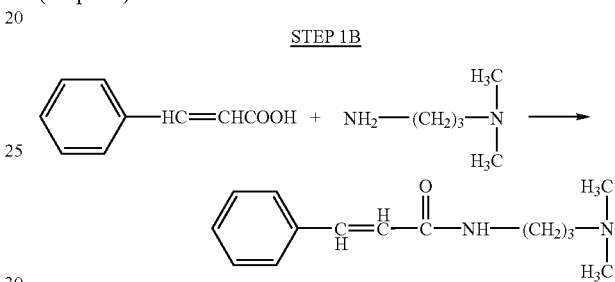

This can also be accomplished using the process described in U.S. Pat. No. 5,633,403, the text of which is hereby incorporated by reference. The product of Step 1B is a carboxylated tertiary amine intermediate, which is then reacted with epichlorohydrine (span abridging molecule which provides a chloride leaving group which can react with the nitrogen on the backbone) in Step 2B to provide a reactive chloroquat intermediate:

STEP 1C

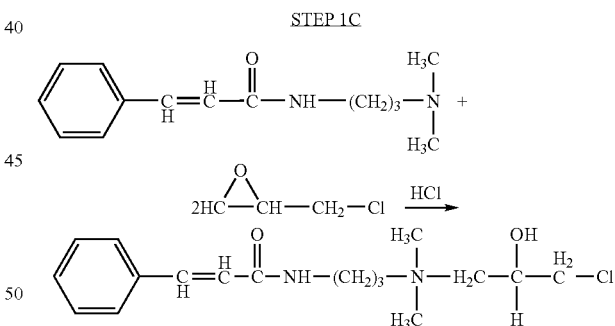

The final synthetic step is the reaction between the products of Steps 1A and 2B that provides the compound (3) in Step 2:

STEP 2

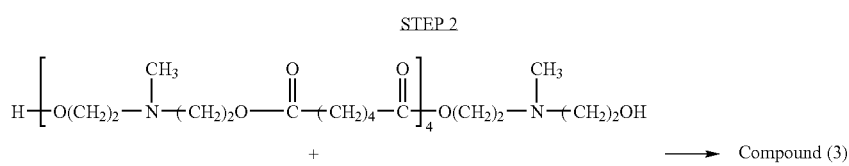

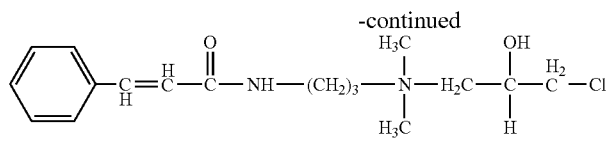

Note that 5 moles of the $R_{10}$ group (used to produce the quat) is needed per mole of oligoester. The preparation of alkoxylated oligoesters of the invention may be carried out in a very similar manner to the preparation of non-alkoxylated compounds. The principal difference in the synthetic route is the presence of preliminary alkoxylation Step 1AA:

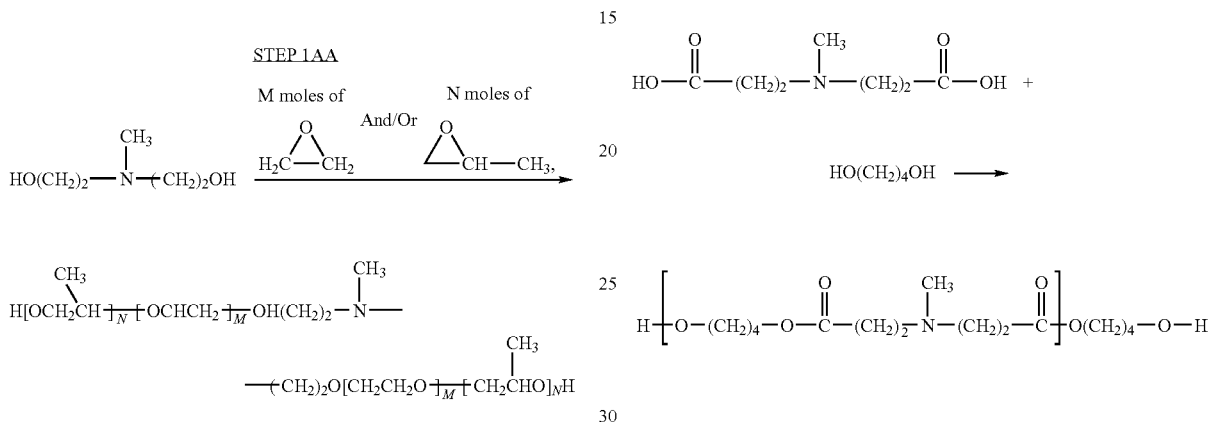

The step 1AA produces alkoxylated methylamine (as shown propoxylated and/or ethoxylated) diethanol, which then may be used in a condensation reaction to provide a backbone oligoester. The use of propylene oxide is preferred.

The following reaction scheme shows the condensation reaction between di-propoxylated diethanol methylamine and adipic acid:

This backbone may then be derivatized as desired, including end-capping, quaternization, and so on.

Another oligoester may be prepared as follows:

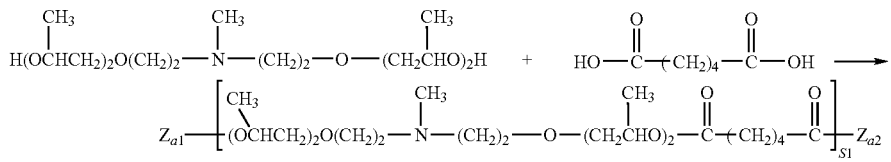

After the desired backbone of the oligoester is formed as shown above, and the desired number of structural units are strung together, it may be derivatized, for example as follows:

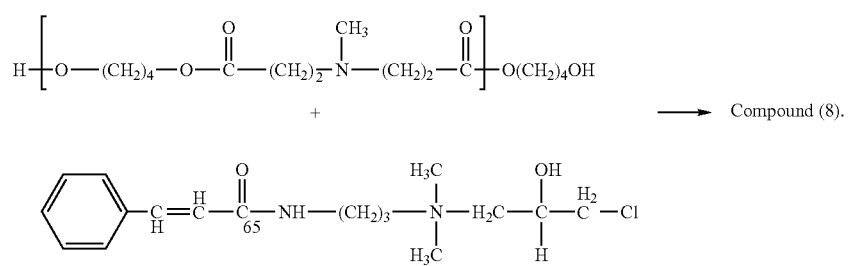

→ Compound (8).

Again multiple moles of $R_{10}$ are needed per each mole of oligoester backbone. The product of the reaction between the backbone oligoester and chloroquat is the compound (8). The reactive chloroquat may be produced as shown in Steps 1A-1C.

Quats of the oligoesters of the present invention represent a special case because of their unique properties as described herein. An important characteristic of quats as raw materials, as well as the final products that incorporate them, is the so-called cationic activity, which measures a concentration of positive charges in a substance, product, etc.

The oligoesters in accordance with the present invention include up to about 100 structural units as previously noted. Again, in addition thereto, there may be an additional diol or diacid to provide a specified functionality at each terminus. More preferably, however, the number of structural units ranges from between about 2 to about 50 and more preferably from about 3 to about 25. In terms of molecular weight, one will appreciate, with the high variability in the structures of the backbones and the pendent groups and end capping, molecular weights can vary widely. However, generally speaking, molecular weights of less than 100,000 units are preferred, preferably less than about 50,000 are preferred and more preferably, less than about 25,000 molecular weight units are preferred. In the context of mixtures, this means that the predominant fraction, the most abundant oligoester, will have the desired number of structural units and/or molecular weight.

Cationic activity is as appropriate for discussion in the context of the oligoester quats of the present invention as for conventional quats. Cationic activity may be measured by several methods readily understood by those skilled in the art. One such method utilizes a standardized solution of an anionic material, such as sodium lauryl sulfate. This material is added to the solution containing the quat until full complexation of the quat's cations (the end point) has been reached. The end point can be measured potentiometrically or by the use of color indicators.

Typical tests involve titrating a sample of the quat, usually dissolved in a solvent, with the standardized solution of sodium lauryl sulfate until the endpoint is reached. As described in the co-pending and co-assigned U.S. patent application Ser. No. 09/438,631, incorporated by reference herein in its entirety, once the endpoint is reached, the cationic activity can be calculated according to the following formula:

$$\% \text{ cationic activity} = \frac{mL \times N \times MW \times 100}{S.wt. \times 1000}$$

Where:
  mL=the number of mL of anionic material
  N=the normality of the solution used
  MW=the equivalent molecular weight of the quat being analyzed
  S. wt.=the sample weight in grams For additional information regarding the methodology for measuring the cationic activity, see W. Schempp and H. T. Trau, *Wochenblatt fur Papierfabrikation* 19, 1981, pages 726-732, or J. P. Fischer and K. Lohr, *Organic Coatings Science Technology*, Volume 8, pages 227-249, Marcel Dekker, Inc. April 1986), both incorporated herein by reference in their entirety.

While cationic activity is an appropriate measure for cationic species, not all of the oligoesters in accordance with the present invention are cationic. Accordingly, it is more generally appropriate to describe the amount of claimed materials using other terminology. It is unusual for oligoesters to be produced or sold in a completely pure form. Whether singular compounds or as parts of mixtures, they generally are present as an additive which includes a solvent which, preferably, acts as a pharmaceutically acceptable or cosmetically acceptable carrier. Because it is possible to drive off all, or substantially all, of the solvent, the upper limit on the proportion of oligoesters is generally less critical. However, when mixed in a solvent, the oligoesters should be present in the resulting additives in an amount of at least about 0.10% by weight of the additive, more preferably at least about 5% by weight of the additive and most preferably at least about 20% by weight of the additive. If solvent is present, the oligoester may be present inasmuch as about 99.0%. More typically, it is present in amounts of up to about 95% and even more typically in amounts of about 75% or less. An effective amount of the solvent carrier in this context is an amount sufficient to solubilize the oligoesters, understanding that they can be in the form of solid solutions which can be flakable which may provide for more convenient handling. Solvents for flakable quats would often include fatty alcohols as a cosolvent. This generally means that the amount of solvent in a oligoester containing additive product ranges from between about 1% to about 99.9%, or preferably between about 5% to about 95% by weight. More typically, however, 80% or less of the formulation is solvent. Most preferably, the amount of solvent is, however, minimized.

When such additives are used to formulate pharmaceutical and cosmetic products, the amount will vary depending upon a number of factors none the least of which is the overall composition of the end product and the role that the oligoester will play. If the oligoester is merely being used for conditioning, one amount may be necessary. If the oligoester is also being used to provide UV protection, some other amount may be indicated. Moreover, depending upon the concentration of the oligoester in the additive to be used, the overall amount of additive may need to be adjusted. The same volume of additive which contains 20% solvent and one which contains 80% solvent obviously affords significantly different quantities of oligoester. Therefore, the amount of additive used in each case may be dramatically different although the intended amount of oligoesters used may be the same. Furthermore, there is generally no upper limit on the amount of oligoester used. Usually cost is the only limiting factor. Of course, at some point the amount of oligoester used may produce a diminishing return. The lower limit is often more critical. Generally, at least about 0.05% by weight of the finished formulation (pharmaceutical, shampoo, conditioner, sunscreen, cosmetic, etc.) will be an oligoester additive or mixture as defined herein. More preferably at least about 0.5% by weight of oligoesters in the present invention will be used and more preferably at least about 1% of the oligoesters, by weight can be used. Generally, not more than about 50% of the formulation by weight and more preferably not more than 25% by weight of the formulation of an oligoester material will be used.

It is desirable to provide raw quats (quat raw materials) in a concentrated form with high cationic activity, as a solid or semi-solid solution or dispersion. Without wishing to be bound by any specific theory, it is believed that a desired amount of a given quat or mixture of quats to be placed in a formulation may be measured by the cationic activity of the quat raw material. The quat raw materials with high cationic activity permit better transportation efficiency since they occupy smaller space while providing the same desired quat amounts. It is also desirable to produce raw quats that, in addition to having high cationic activity, provide for ease in commercial handling and storage. For example, the raw quat that melt at lower temperatures minimize quat decomposition and improve energy efficiency. For this purpose, it is preferred for the raw quats to be flakeable or pastillatable.

Thus, the invention also provides compositions containing oligoesters and mixtures of oligoesters, including oligoester quats, mixtures of oligoester quats and mixtures of one or more oligoesters and one or more oligoester quats of the present invention, as well as mixtures of oligoesters with other conventional active materials and additives. It is possible to mix oligoesters and oligoester quats and conventional esters and or quats, in the form of concentrated, often solid, solutions or suspensions in a suitable carrier. This is more likely, however for mixtures of oligoester quats and non-oligoester quats, with or without solvents or carriers. The preferred carrier or solvent is one that is either pharmaceutically or cosmetically acceptable and used or recognized to have such uses. Preferred solvents include isopropyl alcohol, SDA-40, propylene glycol, butylene glycol, various fatty alcohols, and mixtures thereof. In such instances, the combination of the carrier and the oligoester may be referred to as an additive and the oligoester may be present in an amount of from about 0.1% to about 99% of the additive by weight.

Preferably, in the quat raw material form, the oligoester (1) is provided as a liquid solution in butylene glycol with cationic activity of approximately 70%. The preparation of the oligoester (1) is shown in Examples 15 and 16. The preferred average molecular weight of the oligoester (1) is about 5700. The oligoester (1) is compatible with anionic surfactants and stable in formulations at pH of from about 4.5 to about 8.

Preferably, in the quat raw material form, the oligoester (2) is provided as a flakeable or pastillatable solid in stearyl alcohol with cationic activity of approximately 40%. The preparation of corresponding backbone oligoester is shown in Example 11. The preferred average molecular weight of the oligoester (2) is about 3500. The oligoester (2) is believed to be not compatible with anionic surfactants and stable in formulations at pH of from about 3.5 to about 4.

Preferably, in the quat raw material form, the oligoester (4) is provided as a liquid solution in butylene glycol with cationic activity of approximately 60%. The preparation of the oligoester (4) is shown in Examples 3 and 4. The preferred average molecular weight of the oligoester (4) is about 4000. The oligoester (4) is compatible with anionic surfactants and stable in formulations at pH of from about 4.5 to about 8.

Preferably, in the quat raw material form, the oligoester (5) is provided as a solution in butylene glycol with cationic activity of approximately 70%. The preparation of the corresponding backbone oligoester is shown in Example 14. The preferred average molecular weight of the oligoester (5) is about 5700-6000. The oligoester (5) is compatible with anionic surfactants and stable in formulations at pH of from about 4.5 to about 8.

Preferably, in the quat raw material form, the oligoester (6) is provided as a flakeable or pastillatable solid in stearyl alcohol with cationic activity of approximately 40%. The preparation of the oligoester (5) is shown in Example 8. The preferred average molecular weight of the oligoester (6) is about 4700. The oligoester (6) is believed to be not compatible with anionic surfactants and stable in formulations at pH of from about 3.5 to about 4.

Preferably, in the quat raw material form, the oligoester (7) is provided as a liquid solution in butylene glycol with cationic activity of approximately 60%. The preferred average molecular weight of the oligoester (7) is about 4250. The oligoester (7) is stable in formulations at pH of from about 4.5 to about 8, and not believed to be compatible with anionic surfactants. The oligoester (7) may also be provided as a flakeable or pastillatable solid in stearyl alcohol with cationic activity of approximately 35%. The preparation of the oligoester (7) is shown in Examples 10 and 13.

Preferably, in the quat raw material form, the oligoester (17) is provided as a liquid solution in dipropylene glycol with cationic activity of approximately 75%. The preparation of the oligoester (17) is shown in Example 17.

Preferably, the oligoester quats of the present invention and mixtures including the oligoester quats of the present invention are flakeable or pastillatable solids with high quat cationic activity. The quat cationic activity is the cationic activity that is attributed to quaternary nitrogen compounds. The preferred total quat cationic activity of the quat raw materials of the invention is greater than 10%, preferably, greater than 20%, more preferably, greater than 35%, yet more preferably, greater than 50%. That is to say, as an additive.

As noted above, a common feature of the preferred oligoesters in accordance with the formulas I or II is the oligoester backbone. As has just been described, the backbone can be derivatized and functionalized in many unique ways so as to provide raw materials with interesting and useful properties, particularly in the pharmaceutical, cosmetic and personal care area. The properties of the backbone can be modified by adjusting, inter alia, its length, the number of and types of repeating structural units, the substitutions of the diol or diacid, the placement and type of amine nitrogen(s) in the backbone, and the inclusion of, for example, alkoxy groups. As previously noted, the alkoxy groups act to stabilize these compositions, and in particular, oligoester quats in accordance with the present invention so as to render them stable at pHs between approximately 4 and 9.

Other changes in properties and utility may come about through the use of, amongst other things, different end caps or end groups and different external substituents and/or by forming quats using specific materials. Particularly preferred in accordance with the present invention are formulations which are stable at pHs between about 4 and about 9, compounds which are useful in conditioning hair or skin, compounds which are useful in providing UV protection and making skin softer. Some of the oligoesters of the invention are anionic surfactant compatible (e.g. will not cloud a clear shampoo system). Other oligoesters in accordance with the present invention have a relatively high refractive index, about that of phenyl dimethicone or even higher. For example, the use of quats of benzyl chloride provides a refractive index high enough to add significant shine to hair. Thus, the oligoester (17) is believed to have the refrective index of 1.49.

Oligoesters in accordance with the present invention capable of providing more than one of these advantages are particularly preferred. Thus, for example, a particular oligoester can be a quat with a UV absorptive material and can, simultaneously, be formulated with end caps which will impart extraordinary conditioning. By using oligoesters with alkoxy groups in their backbone, these same formulations can be rendered stable at neutral pH. Thus, a particular oligoester additive in accordance with the present invention can be formulated to be included in the shampoo and to provide viscosity enhancement, conditioning properties and protection from ultraviolet radiation.

In accordance with another aspect, the invention also provides compositions in the form of various, pharmaceutical preparations, cosmetics and/or personal care products which include one or more of the oligoesters of the present invention. Such compositions may be sunscreen compositions for hair and/or skin, such as lotions, gels, sprays, creams and the like, hand cleaners, bath compositions, suntan oils, antiperspirant compositions, perfumes and colognes, cold creams, pre-shaves, deodorants, pharmaceutical preparations (ointments, creams, lotions, gels, treated powders, nose sprays, additives to bandages or transdermal drug applicators such as patches), skin moisturizers, facial cleansers, cleansing creams, skin gels, shampoos, hair conditioners (both conditioners which are rinsed and those which remain on the hair), rinses, cream rinses, detergents, make-up products, permanent waving products, lipsticks, mascara, blush, foundation, rouge, mousse, sprays, styling gels, nail care products including polish and nail conditioners and dyes and hair coloring products. The preferred final product compositions of the invention are compositions for treating human hair, such as shampoos or conditioners.

The nature of final products in accordance with the invention dictates a number of parameters including, amongst others, the type of oligoester to be used, whether a single type of oligoester is used or whether it is mixed with other oligoesters of the present invention, the amount of oligoesters in accordance with the present invention which will be used, and the type and amount of additional ingredients. For example, in a topical pharmaceutical preparation, it may be desirable to omit coloring agents. However, in a hair dye, a nail polish or a blush, for example, pigments, dyes or colors, or materials which will develop color at some point in time during or after application may be specifically contemplated. The type and amount of pigment in a hair dye may be very different than the type and amount of pigment in a blush.

Pharmaceutical, cosmetic and personal care products in accordance with the present invention generally include a pharmaceutically or cosmetically-acceptable solvent; an oligoester including at least two structural units, each structural unit having a diol fragment and a diacid fragment attached to one another by an ester linkage, at least one of said fragments containing a tertiary or quaternary nitrogen atom, said structural units defining a backbone extending through said ester linkages and said tertiary or quaternary nitrogen atoms, said oligoester being present in the amount of from about 0.01% to 99.0% by weight based on the combine weight of said oligoester and said solvent; and at least one active or additional ingredient, provided in an amount which is effective for its intended use. Those of ordinary skill in the art can readily substitute the oligoesters of the present invention into existing formulations in an amount that approximates the use of functionally analogous compounds in existing formulations of the same type and function. For example, in a conditioning shampoo, oligoester formulations of the present invention may be substituted for some or all of the conditioning agents previously included. However, the active or additional ingredient in this instance is the surfactants used for shampooing hair. Therefore, an amount of surfactants must be provided to meet that "intended use" in this case. If, in a given formulation, insufficient conditioning is obtained by a one to one substitution of the oligoesters of the invention for conventional conditioners, then it is a relatively easy and conventional matter to determine the amount of oligoester necessary to provide sufficient additional conditioning using conventional techniques. Similarly, if one of the objects or "intended uses" of the formulation is to act as a sunscreen product for skin or hair, and a oligoester quat produced using a derivative of a UV-active compound as one of the groups bound to the quaternary nitrogens of the backbone is used as a UV absorbing agent, then the amount to be used will be that amount which imparts the desired skin protection factor or "SPF". If UV protection were to provided by a mixture of such oligoester quats with or without conventional UV absorbing quats, then the amount of each component will be such that in total, they provide the formulation with the desired SPF. How much of each used to provide the desired level of SPF will be dictated not only by the resulting SPF but also by the relative cost of each, their relative availability, ease of formulation, other advantageous properties they may impart (i.e. one of the oligoester quats is also a particularly good conditioner and conditioning is desirable), and the like. In this instance, the active or additive might be a conventional UV absorbing material or a cream, lotion or gel base and the effective amount would either be that which is required to provide some SPF factor or to form a cream, gel or lotion useful as a personal care product that successfully and stably supports the oligoesters of the invention. In the case of a pharmaceutical product which includes the oligoesters of the present invention, the amount of the active or additional ingredient refers to the amount of the pharmaceutically active ingredient which should be provided in an amount to be therapeutically or medically useful.

An effective amount of a pharmaceutical for its intended use can very widely, however, generally between about 0.1 and about 75% by weight of the formulation can be an active agent which is a pharmaceutical. At least one active or additional ingredient, provided in an amount which is effective for its intended use, in the context of cosmetics and personal care products generally refers to the amount of surfactants, conditioners, carriers, pigments and the like which are described herein.

Pharmaceutical, cosmetic or personal care compounds or products in accordance with the present invention, which include one or more of the oligoesters of the present invention, will generally include between about 0.05% and about 50% by weight of said oligoesters or oligoester mixtures. More preferably, the amount of oligoesters will range from between about 0.5% to about 50% and even more preferably from between about 1% to about 25% by weight of the finished product. However, it will be appreciated that different amounts of the oligoesters may be preferred given a particular product type and the use of an alkoxylated backbone, a quat or one of the other variations or derivatives of the backbone oligoesters described herein.

Final products including the oligoesters or mixtures thereof in accordance with the present invention may be in the form of liquids, ointments, lotions, sprays, gels, creams, emulsions, foams, pastes and solids; may be clear or opaque; and may be formulated as aqueous and non-aqueous preparations, including but not limited to topical preparations. Preferably, such final products are dispersions or solutions in water, or in a mixture of water with a suitable secondary solvent. Suitable solvents include various lower alkanols and glycols. Lower alkanols having from one to four carbon atoms are suitable for use with the present invention, and lower alkanols having from two to three carbon atoms are preferred. Glycols having from three to eight carbon atoms are suitable for use with the present invention, while glycols having from three to six carbon atoms are preferred. Examples of suitable lower alkanols and glycols include methanol, ethanol, isopropanol, butanol, hexylene glycol, 1,3-butylene glycol, 1,2- and 1,3-propane diol, 2-methyl 1,3-propane diol, propylene glycol, diethylene glycol, and the like.

The total amount of solvent, including water and mixtures of water and solvents, may be up to about 98% by weight of the composition, preferably, from about 20% to about 90%, more preferably, from about 50% to about 90% by weight of the composition. Again, however, different amounts of solvent may be preferred depending on the nature of the product.

If a mixture of water and a secondary solvent is used, the secondary solvent may be present in the amount of up to 90%, preferably, between about 25% and about 80% by weight of water in the composition.

In addition to oligoesters, the formulations of the invention may include various active and additional ingredients, both conventional and otherwise. Of course, a decision to include an ingredient and the choice of specific active and additional ingredients depends on the specific application and product formulation. Also, the line of demarcation between an "active" ingredient and an "additional ingredient" is artificial and dependent on the specific application and product type. A substance that is an "active" ingredient in one application or product may be an "additional" ingredient in another, and vice versa.

Thus, the compositions of the invention may include one or more active ingredients, which provide some benefit to the object of the application of the composition, for example, hair or skin. Such active ingredients may include one or more substances such as cleaning agents, hair conditioning agents, skin conditioning agents, hair styling agents, antidandruff agents, hair growth promoters, perfumes, sunscreen compounds, pigments, moisturizers, film formers, humectants, alpha-hydroxy acids, hair colors, make-up agents, detergents, thickening agents, emulsifiers, antiseptic agents, deodorant actives and surfactants. They may include agents which enhance permeation into or through the skin, or topical pharmaceuticals such as, without limitation, corticosteriods, analgesics, anti-inflammatory agents, antibiotics, anesthetics, etc. These may all be used in conventional and/or approved amounts.

The choice of the active ingredient(s) depends on the nature of the desired pharmaceutical, cosmetic or personal care product. Active ingredients generally, but other additives possibly, can be included in various forms. They may be included in a liquid or solid form. Solids can be crystalline or amorphous, granular, powder, particulate and the like. However, it is also possible for such additives to be microencapsulated or in the form of micro particles.

One of the active or additional ingredients which may be used in products along with the oligoester compositions of matter and/or mixtures of the present invention are surfactants including one or more nonionic surfactants, anionic surfactants, cationic surfactants, amphoteric surfactants, zwitterionic surfactants, and mixtures thereof. Surfactants in cleansers or shampoos could be an active agent. In other formulations, it can be an emulsifier and is, therefore, an additional agent. For some of surfactants that may be used in combination with the compositions of the invention, see McCutcheon's, *Detergents and Emulsifiers*, (1986), as well as U.S. Pat. Nos. 5,151,210, 5,151,209, 5,120,532, 5,011,681, 4,788,006, 4,741,855, 4,704,272, 4,557,853, 4,421,769, 3,755,560; all incorporated herein by reference in their entirety.

Cationic surfactants suitable for use in various personal care products, especially hair care products such as conditioners and shampoos include quaternary ammonium cationic surfactants of the formula

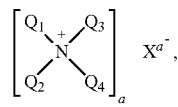

where X and a are as previously described, $Q_1$ is $C_{12}$-$C_{22}$ alkyl, $C_{12}$-$C_{22}$ alkyl amido $C_1$-$C_6$ alkylene, $C_{12}$-$C_{22}$ alkylhydroxy; $Q_2$ is $C_{12}$-$C_{22}$ alkyl, $C_{12}$-$C_{22}$ alkyl amido $C_1$-$C_6$ alkylene, $C_{12}$-$C_{22}$ alkylhydroxy, benzyl, or $C_1$-$C_6$ alkyl; $Q_3$ and $Q_4$ are independently $C_1$-$C_6$ alkyl or benzyl.

Examples of suitable quaternary ammonium surfactants include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the $C_{12}$-$C_{22}$ alkyl is derived from a tallow fatty acid or from a coconut fatty acid. Examples of quaternary ammonium salts derived from these tallow and cococut sources include ditallow dimethyl ammonium chloride, ditallow dimehtyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconut alkyl)dimethyl ammonium chloride, di(coconut alkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium surfactants are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Fatty Amines

The compositions of the invention may also include salts of primary, secondary and tertiary $C_{12}$-$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

Amidoamines.

The compositions of the invention may also include aminoamides, such as disclosed in U.S. patent application Ser. No. 09/409,203, assigned to Croda Inc., and incorporated by reference herein. Suitable additional cationic surfactants are disclosed in McCutcheon, Detergents & Emulsifiers, (M.C. Publishing Co. 1979); U.S. Pat. Nos. 3,155,591, 3,929,678, 3,959,461, 4,387,090, which are incorporated by reference herein. The amounts and the nature of cationic surfactants present in the compositions of the invention, if at all, depend on the nature of the composition. In the final product, the total amount of cationic surfactants, may vary from 0.1% to about 40%, more preferably, from about 0.1% to about 15%, yet more preferably, from about 0.5% to about 2% by the weight of the product composition. However, different amounts of cationic surfactants may be preferred depending on the nature of the product.

The compositions of the invention may also include various non-ionic surfactants. Among the suitable nonionic surfactants are condensation products of $C_8$-$C_{30}$ alcohols with sugar or starch polymers. These compounds can be represented by the formula $(S)_n$—O—R, wherein S is a sugar moiety such as glucose, fructose, mannose, and galactose; n is an integer of from about 1 to about 1000, and R is $C_8$-$C_{30}$ alkyl. Examples of suitable $C_8$-$C_{30}$ alcohols from which the R group may be derived include decyl alcohol, cetyl alcohol, stearyl alcohol, lauryl alcohol, myristyl alcohol, oleyl alcohol, and the like. Specific examples of these surfactants include decyl polyglucoside and lauryl polyglucoside.

Other suitable nonionic surfactants include the condensation products of alkylene oxides with fatty acids (i.e., alkylene oxide esters of fatty acids). These materials have the general formula $RCO(X)_n$ OH, wherein R is a $C_{10}$-$C_{30}$ alkyl, X is —OCH$_2$CH$_2$— (derived from ethylene oxide) or —OCH$_2$CHCH$_3$— (derived from propylene oxide), and n is an integer from about 1 to about 200.

Yet other suitable nonionic surfactants are the condensation products of alkylene oxides with fatty acids (i.e., alkylene oxide diesters of fatty acids) having the formula $RCO(X)_n$OOCR, wherein R is a $C_{10}$-$C_{30}$ alkyl, X is —OCH$_2$CH$_2$— (derived from ethylene oxide) or —OCH$_2$CHCH$_3$— (derived from propylene oxide), and n is an integer from about 1 to about 200.

Yet other nonionic surfactants are the condensation products of alkylene oxides with fatty alcohols (i.e., alkylene oxide ethers of fatty alcohols) having the general formula $R(X)_n$OR', wherein R is $C_{10}$-$C_{30}$ alkyl, n is an integer from about 1 to about 200, and R' is H or a $C_{10}$-$C_{30}$ alkyl.

Still other nonionic surfactants are the compounds having the formula $RCO(X)_n$OR' wherein R and R' are $C_{10}$-$C_{30}$ alkyl, X is —OCH$_2$CH$_2$— (derived from ethylene oxide) or —OCH$_2$CHCH$_3$— (derived from propylene oxide), and n is an integer from about 1 to about 200.

Examples of alkylene oxide-derived nonionic surfactants include ceteth-1, ceteth-2, ceteth-6, ceteth-10, ceteth-12, ceteareth-2, ceteareth6, ceteareth-10, ceteareth-12, steareth-1, steareth-2, steareth-6, steareth-10, steareth-12, PEG-2 stearate, PEG4 stearate, PEG6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amides disclosed, for example, in U.S. Pat. Nos. 2,965,576, 2,703,798, and 1,985,424, which are incorporated herein by reference.

If non-ionic surfactants are used, their amounts will vary based on the formulation, the remaining ingredients and the types, if any, of any surfactants which are being used. In general, the amount of non-ionic surfactants which are useful in accordance with the present invention may vary from 0.1% to about 40%, more preferably from about 0.1% to about 15%, and yet more preferably from about 0.5% to about 2% by weight of the final formulation. However, as previously noted, different amounts of non-ionic surfactants may be preferred, depending on the nature of the product.

The compositions of the invention may also include various anionic surfactants. Several examples of suitable anionic surfactants are disclosed in U.S. Pat. No. 3,929,678, which is incorporated herein by reference. Further examples of suitable anionic surfactants include alkoyl isethionates, and alkyl ether sulfates.

The alkoyl isethionates typically have the formula RCO—OCH$_2$CH$_2$—SO$_3$M, wherein R is $C_{10}$-$C_{30}$ alkyl, and M is a water-soluble cation, such as ammonium, sodium, potassium, or triethanolamine. The examples of suitable isethionates include ammonium cocoyl isethionate, sodium cocoyl isethionate, sodium lauroyl isethionate, sodium stearoyl isethionate, and mixtures thereof. Preferred for used herein are ammonium cocoyl isethionate, sodium cocoyl isethionate, and mixtures thereof.

The alkyl ether sulfates typically have the formulas ROSO$_3$M and RO(C$_2$H$_4$O)$_x$SO$_3$M, where R is $C_{10}$-$C_{30}$ alkyl, x varies from about 1 to about 10, and M is a water-soluble cation such as ammonium, sodium, potassium and triethanolamine.

Yet another suitable class of anionic surfactants are alkali metal salts of $C_8$-$C_{30}$ carboxylic acids and alkylsulfonates of the formula $R_1$—SO$_3$M (where $R_1$ is $C_8$-$C_{30}$ alkyl; preferably, $C_{12}$-$C_{22}$ alkyl, and M is a cation), including succinamates, and $C_{12}$-$C_{24}$ olefin sulfonates and carboxylates.

If ionic surfactants are used, their amounts will vary based on the formulation, the remaining ingredients and the types, if any, of any surfactants which are being used. In general, the amount of ionic surfactants which are useful in accordance with the present invention may vary from 0.1% to about 40%, more preferably from about 0.1% to about 15%, and yet more preferably from about 0.5% to about 2% by weight of the final formulation. However, as previously noted, different amounts of ionic surfactants may be preferred, depending on the nature of the product.

The compositions of the invention may also include zwitterionic and amphoteric surfactants. Suitable amphoteric and zwitterionic surfactants are, for example, derivatives of mono- or di-$C_8$-$C_{24}$ secondary and tertiary amines, such as alkyl imino acetates, carboxylates, sulfonates, sulfates, phosphates, and phosphonates, including iminodialkanoates and aminoalkanoates of the formulas $RN(CH_2)_m$ CO$_2$ M$_2$ and $RNH(CH_2)_m$ CO$_2$M, where m varies from 1 to 4, R is $C_8$-$C_{30}$ alkyl; preferably, $C_{12}$-$C_{22}$ alkyl, and M is H, alkali metal, alkaline earth metal ammonium, or alkanolammonium.

Other suitable amphoteric and zwitterionic surfactants are imidazolinium and ammonium derivates. Suitable examples of such amphoteric surfactants include sodium 3-dodecyl-aminopropionate, sodium 3-dodecylaminopropane sulfonate, N-alkyltaurines; N-higher alkyl aspartic acids, and coamidopropyl PG-dimonium chloride phosphate. For further examples of suitable amphoteric and zwitterionic surfactants, please see U.S. Pat. Nos. 2,658,072, 2,438,091, and 2,528,378, which are incorporated herein by reference Yet other suitable amphoteric and zwitterionic surfactants are betaines. Examples of suitable betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines, oleyl betaine, and cocamidopropyl betaine.

The compositions of the invention may include quaternary ammonium compositions of matter of the formula

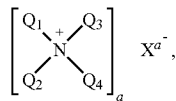

where X and a are as previously described, $Q_1$ is $C_{12}$-$C_{22}$ alkyl, $C_{12}$-$C_{22}$ alkyl amido $C_1$-$C_6$ alkylene, $C_{12}$-$C_{22}$ alkylhydroxy; $Q_2$ is $C_{12}$-$C_{22}$ alkyl, $C_{12}$-$C_{22}$ alkyl amido $C_1$-$C_6$ alkylene, $C_{12}$-$C_{22}$ alkylhydroxy, benzyl, or $C_1$-$C_6$ alkyl; $Q_3$ and $Q_4$ are independently $C_1$-$C_6$ alkyl or benzyl. These quats may be used alone or in combination with oligoester quats of the present invention. Thus, a formulation in accordance with the present invention could include an oligoester, an oligoester quat and a conventional quat as well.

Examples of suitable quaternary ammonium compounds include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the $C_{12}$-$C_{22}$ alkyl is derived from a tallow fatty acid or from a coconut fatty acid. Examples of quaternary ammonium salts derived from these tallow and cococut sources include ditallow dimethyl ammonium chloride, ditallow dimethyl ammonium methyl sulfate, di(hydrogenated tallow)dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl) dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium compositions are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

When present, quaternary ammonium compositions (other than those made from oligoesters) of the present invention can be provided in any amount desirable and the amount will depend upon the factors previously discussed, including the purpose of the end formulation and its overall composition. That said, however, these quaternary ammonium compositions may be present in an amount of between about 0 and about 50%, preferably in an amount of between about 0.1 and about 25% and more preferably in an amount of between about 1 and about 10% by weight of the final composition. These amounts may be reduced if quaternary ammonium compounds as described herein are used in combination with oligoester quats of the invention, although in certain circumstances, the presence of one will have no affect on the amount of the other used.

The compositions of the invention may also include salts of primary, secondary and tertiary $C_{12}$-$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

The compositions of the invention may also include aminoamides, such as disclosed in U.S. patent application Ser. No. 09/409,203, assigned to Croda, Inc., and incorporated by reference herein. The amount of fatty amines and/or amido amines will generally vary under the same conditions as the quaternary ammonium compounds as described above.

If amphoteric surfactants are used, their amounts will vary based on the formulation, the remaining ingredients and the types, if any, of any surfactants which are being used. In general, the amount of amphoteric surfactants which are useful in accordance with the present invention may vary from 0.1% to about 40%, more preferably from about 0.1% to about 15%, and yet more preferably from about 0.5% to about 2% by weight of the final formulation. However, as previously noted, different amounts of amphoteric surfactants may be preferred, depending on the nature of the product.

A wide variety of sunscreen compounds are suitable for use with the compositions of the present invention to provide UV protection. Depending on the nature of the composition, the sunscreen compounds may be added in the amount of up to about 40% by weight of the composition, preferably, from about 1% to about 30%. However, the preferred amount may vary depending on the nature of the composition. Thus, for the final product compositions in the form of a shampoo or conditioner, the suitable sunscreen agent may be included in the amount of up to about 40% by weight of the composition, preferably, from about 0.5% to about 10%, more preferably, from about 0.5% to about 5% by weight of the composition. This is exclusive of the amount of UV-protecting groups found in the oligoesters used.

Sunscreens may be in the form of shampoos, conditioners including so-called "leave-in" conditioners, hairsprays, as well as products specifically intended as sunscreens for hair and/or skin including lotions, gels, sprays and the like.

Suitable sunscreen compounds include, for example, p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxy-naphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; amino benzoates, salicylates, ferrulic acid derivatives, phenylbenzimidazole sulfonic acids, benzophenone sulfonic acids, thioctic acids derivatives, oil-soluble cinnamates, and benzophenones. For other suitable sunscreen compounds, please see Segarin, et al., Cosmetics Science and Technology, Chapter VIII, pages 189 et seq., incorporated herein by reference.

Specific suitable sunscreen compounds include 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4->bis (hydroxypropyl)!-aminobenzoate, 2-ethylhexyl-2-cyano-3, 3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylaminobenzoate, 2-phenylbenzimidazole-5-sulfonic acid, 2-(p-dimethyl-aminophenyl)-5-sulfonicbenzoxazoic acid, para-aminobenzoic acid, benzophenone-1, benzophenone-1, benzophenone-2, benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl methoxycinnamate, octyl salicylate, zinc oxide, titanium dioxide, and red petrolatum.

In one embodiment of the invention, the oligoesters of the present invention, and even more preferably, the oligoester quats which themselves include one or more $R_{uv}$ groups, are mixed or blended with other UV active compounds or formulations which include other UV active compounds. Non-limiting examples of these other UV active compounds include all of those noted above and, preferably para-aminobenzoic acid (PABA), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid. These may be used in the amounts previously described for other sunscreen additives discussed above.

The compositions of the invention may also include one or emollient compounds such as fats, waxes, lipids, silicones, hydrocarbons, fatty alcohols and a wide variety of solvent materials. The amount of the emollient depends on the application. For the final product compositions, emollients are included in the amount of up to 50% by weight of the composition, preferably, from about 0.1% to about 20%, and more preferably, from about 0.5% to about 10% by weight of the composition.

Examples of suitable emollients include $C_{8-30}$ alkyl esters of $C_{8-30}$ carboxylic acids; $C_{1-6}$ diol monoesters and diesters of $C_{8-30}$ carboxylic acids; monoglycerides, diglycerides, and triglycerides of $C_{8-30}$ carboxylic acids, cholesterol esters of $C_{8-30}$ carboxylic acids, cholesterol, and hydrocarbons. Examples of these materials include diisopropyl adipate, isopropyl myristate, isopropyl palmitate, ethylhexyl palmitate, isodecyl neopentanoate, $C_{12-15}$ alcohols benzoates, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters, mineral oil, petrolatum, and straight and branched $C_{16}$-$C_{30}$ hydrocarbons.

Also useful are straight and branched chain fatty $C_8$-$C_{30}$ alcohols, for example, stearyl alcohol, isostearyl alcohol, ethenyl alcohol, cetyl alcohol, isocetyl alcohol, and mixtures thereof. Examples of other suitable emollients are disclosed in U.S. Pat. No. 4,919,934; which is incorporated herein by reference in its entirety.

Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof.

Examples of suitable alkoxylated diesters and trimesters are disclosed in U.S. Pat. Nos. 5,382,377, 5,455,025 and 5,597,555, assigned to Croda Inc., and incorporated herein by reference.

Suitable lipids include $C_8$-$C_{20}$ alcohol monosorbitan esters, $C_8$-$C_{20}$ alcohol sorbitan diesters, $C_8$-$C_{20}$ alcohol sorbitan triesters, $C_8$-$C_{20}$ alcohol sucrose monoesters, $C_8$-$C_{20}$ alcohol sucrose diesters, $C_8$-$C_{20}$ alcohol sucrose triesters, and $C_8$-$C_{20}$ fatty alcohol esters of $C_2$-$C_{62}$-hydroxy acids. Examples of specific suitable lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan esquistearte, sorbitan stearate, sorbitan triiostearte, sorbitan trioleate, orbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearte, sorbitan dilaurate, sorbitan stearate, sorbitan laurate, sucrose laurate, sucrose dilaurate, sodium isostearyl lactylate, lauryl pidolate, sorbitan stearate, stearyl alcohol, cetyl alcohol, behenyl alcohol, PPG-14 butyl ether, PPG-15 stearyl ether, and mixtures thereof.

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, polyethylene glycols, polypropyleneglyocis, and mixtures thereof.

The compositions of the invention may also include antidandruff agents. The examples of suitable antidandruff agents include zinc pyrithione, sulphur, and selenium sulfide.

The compositions of the invention may also include hair oxidizing/reducing agents. The examples of suitable hair oxidizing/reducing agents include hydrogen peroxide, perborate, thioglycolates and persulfate salts.

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition.

The specific examples of the suitable thickening silicon compounds include polydimethylsiloxane, phenylsilicone, polydiethylsiloxane, and polymethylphenylsiloxane. Some of the suitable silicon compounds are described in European Patten Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

The compositions of the invention may also include hydrolyzed animal protein hair conditioning agents. Croda Incorporated sells an example of a commercially available material under the trade name Crotein Q-RTM. Other examples include urea, glycerol, and propoxylated glycerols, including those described in U.S. Pat. No. 4,976,953, which is incorporated by reference herein.

The compositions of the invention may also include a hair setting agent to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic. Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyl-triethylammonium bromide; amine derivatives of methacrylic acid or amine derivatives of methacrylamide derived from methacrylic acid or methacrylamide and a dialkylalkanolamine having $C_1$-$C_6$ alkyl groups such as dimethylaminoethyl (meth)acrylate, diethylaminoethyl (meth)acrylate, dimethylaminopropyl (meth)acrylate, or dimethylaminopropyl (meth)acrylamide.

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

Examples of nonionic monomers are acrylic or methacrylic acid esters of $C_1$-$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, methoxy ethyl (meth)acrylate, butoxyethyl (meth)acrylate; allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

The compositions of the invention may also include a wide range of miscellaneous ingredients. Some suitable miscellaneous ingredients commonly used in the cosmetic and personal care industry are described in *The CTFA Cosmetic Ingredient Handbook*, ($2^{nd}$ Ed., 1992), which is incorporated by reference herein. These ingredients will be used in amounts which are conventional.

Thus, the compositions of the invention may also include one or more absorbents, anti-acne agents, anti-perspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occlusive), skin soothing agents, skin healing agents, softeners, solubilizing agents, lubricants, penetrants, plasticizers, salts, essential oils, and vitamins. The amount of each if used can very widely depending on the product. However, they are generally used in conventional amounts. So, for example, if shampoos generally use between about 0.1 and 5% by weight of a fragrance, that is the amount that will generally be used in shampoos formulated with one or more of the oligoesters of the present invention. Generally however, the amount of each of these used will be less than 50% by weight and more preferably less than or equal to 25% by weight.

The examples of suitable pH adjusters include sodium hydroxide, triethanoleamine, and aminomethylpropanol, and mixtures thereof. If pH adjusters are present in a final product composition, the amount may vary from about 0.01% to about 5%, preferably, from about 0.1% to about 2% by weight of the composition.

The examples of suitable film formers include glycerin/diethylene glycol myrystate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

The examples of suitable vitamins include tocopherol, tocopherol acetate, retinoic acid, retinol, and retinoids.

The examples of suitable anti-acne medicaments include resorcinol, sulfur, salicylic acid, erythromycin, zinc, and benzoyl peroxide.

The examples of suitable skin bleaching or lightening agents include hydroquinone, and kojic acid. The examples of suitable aesthetic components such as fragrances, pigments, colorings, and the like, include panthenol and derivatives (e.g., ethyl panthenol), aloe vera, pantothenic acid and its derivatives, clove oil, menthol, camphor, eucalyptus oil, eugenol, menthyl lactate, witch hazel distillate, allantoin, bisabolol, and dipotassium glycyrrhizinate.

EXAMPLE 1

Preparation of
PPG-4-N-Methyl-N,N-Diethanolamine 1356.09 g (11.38 moles) of N-Methyl-N,N-Diethanolamine were placed in a dry stirred pressure vessel fitted with a Nitrogen inlet. A catalytic amount (15 g) of 40% aqueous solution of KOH was added. The vessel was purged with Nitrogen and heated to 110° C. Vacuum was applied for 1 hour. Mixture was further heated to 125-130° C. After 2643.91 g (45.52 moles) of Propylene Oxide were added, the reaction mixture was stirred for an additional 3 hours to proceed the reaction to the completion. The progress of the reaction was monitored by the uptake of the reagent and the measurement of the pressure in the vessel. The reaction mixture was cooled to 100-105° C. and vacuum was applied for approximately 1 hour. To neutralize KOH catalyst, 14.1 g of 50% Hypophosphorous Acid was added. Upon cooling down, PPG-4-N-Methyl-N,N-Diethanolamine was obtained and appeared as a viscous yellow liquid with a Base Value of 160.5 mg KOH/g.

EXAMPLE 2

Preparation of
PPG-4-N-Methyl-N,N-Diethanolamine Adipate
Oligomer

Into a four-necked flask, fitted with a mechanical stirrer, a thermometer and a Nitrogen inlet, 1714.70 g (4.906 moles) of PPG-4-N-Methyl-N,N-Diethanolamine from Example 1 and 585.3 g (4.00 moles) of Adipic Acid were charged and 4.6 g of Hypophosphorous Acid catalyst was added. Mixture was gradually heated to 220-225° C. and held while stirring under Nitrogen for 6-8 hours to form the hydroxyl terminated oligomer. The process of the reaction was monitored by measuring the drop in Acid Value. The reaction was stopped once the Acid Value was <7. The resulting product, PPG-4-N-Methyl-N,N-Diethanolamine Adipate (hydroxyl terminated oligomer), appeared as a yellow viscous liquid and had a Hydroxyl Value of 41 and a Base Value of 117.

Based on the hydroxyl value of product from Example 2, the molecular weight was calculated to be 2736.58.

(56100/41)×2=2736.58

This product was also tested by GPC and was found to have a weight average molecular weight $M_w$ of 2703. See FIG. 1.

EXAMPLE 3

Preparation of Poly(N-Hydroxypolyoxypropylethyl)
N-Adipyl-Poly-Oxypropyl)-N-Methyl-N-(2-Hydroxy-3-Cinnamidopropyl Dimethyl Ammonium
Chloride) Methane Sulfonate. Also Known as
Polyquaternium 59 and 1,3-butanediol or Butylene
Glycol or Crodasorb UV-HPP Into a four-necked flask, fitted with a mechanical stirrer, condenser, thermometer and a Nitrogen inlet was added 665.53 g (1.40 moles) of PPG-4-N-Methyl-N,N-Diethanolamine Adipate oligomer, from Example 2, and 240.43 g (2.67 moles) of 1,3-Butanediol. With the reaction mixture at 30-35° C., 131.89 g (1.37 moles) of Methanesulfonic Acid (MSA) was slowly added to neutralize the amine. The reaction was monitored by measuring the Acid Value and Base Value of the reaction mixture over time. When Methanesulfonic salt of PPG-4-N-Methyl-N,N-Diethanolamine Adipate oligomer was formed, 120.51 g (1.30 moles) of Epichlorohydrin was charged. The reaction temperature was increased to 85-90° C. and kept under Nitrogen blanket while it stirred for the next 6 hours. Reaction was monitored by the drop in Acid Value. When the acid value stabilized, 541.63 g (1.6105 moles) of Cinnamidopropyldimethylamine was charged (Cinnamidopropyldimethylamine was prepared as disclosed in example 1 in U.S. Pat. No. 5,633,403). The reaction mixture was stirred for 6 hours at 85-90° C. and was monitored by a drop in Base Value. When the base value drop stabilized, the product was diluted with water to 64-68% actives to improve fluidity. The resulting product, [Poly(N-Hydroxypolyoxypropylethyl) N-Adipyl-Poly-Oxypropyl)-N-Methyl-N-(2, Hydroxy-3-Cinnamidopropyl Dimethyl Ammonium Chloride) Methane Sulfonate] was obtained as a viscous yellow liquid.

EXAMPLE 4

Preparation of Poly(N-Hydroxypolyoxypropylethyl) N-Adipyl-Poly-Oxypropyl)-N-Methyl-N-(2-Hydroxy-3-Cinnamidopropyl Dimethyl Ammonium Chloride) Chloride Into a four-necked flask, fitted with a mechanical stirrer, condenser, thermometer and a Nitrogen inlet, were added 324.2 g (0.68 moles) of PPG-4-N-Methyl-N,N-Diethanolamine Adipate oligomer, from Example 2, and heated under Nitrogen to 40° C. 67.7 g (0.689 moles) of 37% active Hydrochloric Acid were added slowly. After all the Hydrochloric Acid was added, mixture was allowed to react for 1 hour at 50-55° C. Reaction was monitored by measuring the rise in Acid Value of the reaction mixture over time. When Hydrochloric salt of PPG-4-N-Methyl-N,N-Diethanolamine Adipate oligomer was formed, as determined by Base and Acid values, 62.5 g (0.675 moles) of Epichlorohydrin were charged. After all the Epichlorohydrin was added, the reaction temperature was increased to 75-80° C. The contents of the vessel were then allowed to react at 75-80° for 4 hours. Reaction was monitored by Acid and Base Values. When the Acid and Base Values stabilized, 275.4 g (0.82 moles) of Cinnamidopropyldimethylamine (prepared as disclosed in U.S. Pat. No. 5,633,403) was added. Reaction temperature was increased to 85-90° C. and reaction mixture was held 6 hours and monitored by a drop in Base Value. When the Base Value stabilized, the product was diluted with 270.2 g (15 moles) of Deionized Water to 65% actives. The resulting product, Poly(N-Hydroxypolyoxypropylethyl) N-Adipyl-Poly-Oxypropyl)-N-Methyl-N-(2,Hydroxy-3-Cinnamidopropyl Dimethyl Ammonium Chloride) Chloride, appeared as a clear yellow viscous liquid at room temperature.

EXAMPLE 5

Preparation of High Molecular Weight Oligoesters

Higher MW Olygoesters of the material of Example 2 was prepared.

To a clean, dry stirred pressure vessel fitted with nitrogen sparge was charged 1143.33 grams (0.549 moles) of the PPG-4-N-Methyl-N,N-Diethanolamine Adipate Oligomer from example 2, 256.67 grams (0.448 moles) of Unidyme 14™ (from Arizona Chemical Co.) and 2.1 grams of 50% Hypophosphorous Acid. The contents were heated to 220-225° C. under Nitrogen sparge. Upon reaching 220-225° C., a vacuum of 30 mm Hg was applied for 16-20 hours to form the hydroxyl-terminated oligomer. During application of vacuum, the progress of the reaction was monitored by the decrease in Acid Value. The reaction was considered finished when the Acid Value was less than 7 mg KOH. The resulting product was a viscous amber liquid with a Hydroxyl Value of 5 mg KOH.

Based on the Hydroxyl value, the average molecular weight for this product was calculated to be 22440:

(56100/5)×2 =22440

EXAMPLE 6

Preparation of N-Methyl-N,N-Diethanolamine Adipate Oligomer (non-alkoxylated)

Into a four-necked flask, fitted with a mechanical stirrer, condenser, thermometer and a Nitrogen inlet, were added 840.75 g (7.06 moles) of N-Methyl-N,N-Diethanolamine, and 859.25 g (5.88 moles) of Adipic Acid were charged and a catalytic amount (0.2% of batch charge) of 50% Hypophosphorous Acid. The reaction mixture was gradually heated to 180° C. The reaction was monitored by Acid Value and Hydroxyl Value of reaction mixture over time and was stopped once the Acid Value was <6.0. The resulting product, N-Methyl-N,N-Diethanolamine Adipate oligomer had a Hydroxyl Value of 48.7, a Base Value of 252 and an Acid Value of 5.5 and appeared as a yellow viscous liquid.

EXAMPLE 7

Preparation of Di-Poly(12-Hydroxystearate) Ester (End Capped) of N-Methyl-N,N-Diethanolamine Adipate Oligomer A mixture of 885.58 g (0.384 moles) of N-Methyl-N,N-Diethanolamine Adipate oligomer, was made as described in Example 6 and 1114.42 g (0.768 moles) Poly(12-Hydroxysterate), prepared as described in U.S. Pat. No. 3,778,287, were charged into a four-necked flask, fitted with a mechanical stirrer, condenser, thermometer and a Nitrogen inlet. A catalytic amount of Hypophosphorous Acid, 3 g of a 50% solution, was added and the reaction mixture was heated to 180-200° C. and held for 20 hours. Reaction progress was tracked by Acid Value. Once the Acid Value stabilized, the product was cooled and the resulting Di-Poly(12-Hydroxysterate) ester of N-Methyl-N,N-Diethanolamine Adipate oligomer was obtained, as the major product, in the form of amber viscous liquid with Acid Value 5.1.

EXAMPLE 8

Production of Mixed Quat System of Quaternized Dimethylsulfate Quat of Cetyl Dimethylamine (Monoalkylamine) and Di-Poly(12-Hydroxystearate) Ester of N-Methyl-N,N-Diethanolamine Adipate Oligomer (End Capped Oligoester)

Into a four-necked flask, fitted with a mechanical stirrer, thermometer and a Nitrogen inlet, were added 182.37 g (0.354 moles) of Di-Poly(12-Hydroxystearate) of N-Methyl- N,N-Diethanolamine Adipate oligomer from Example 7, 121.58 g (0.446 moles) of Cetyl Dimethylamine, and 600 g (2.2 moles) of Stearyl Alcohol. Reaction mixture was heated under Nitrogen to 75° C. and 96.05 g (0.76 moles) of Dimethyl Sulfate was added dropwise. The reaction was held at 75-80° C. for 1 hour after the DMS addition and was monitored by Acid Value, Base Value. Once the Base Value stabilized, the final product had a 40% total quat actives and appeared as an off-white flakeable waxy solid with a Base Value 2.4 mg KOH.

EXAMPLE 9

Dimer Acid Oligomer of PPG-4-N-Methyl-N,N-Diethanolamine (Alkoxylated with H Moles of Propylene Oxide)

Into a four-necked flask, fitted with a mechanical stirrer, thermometer, and a Nitrogen inlet, 512.42 g (1.46 moles) of PPG-4-N-Methyl-N,N,-Diethanolamine from Example 1 were charged and 687.58 g (1.1968 moles) of Dimer Fatty Acids (Unidyme (R)14 from Arizona Chemicals) and 1.8 g of 50% Hypophosphorous Acid ($C_{36}$ diacid produced from two oleic fatty acid molecules). The mixture was gradually heated to 220-225° C. and held while stirring under Nitrogen for 10 hours to form the hydroxyl terminated oligomer. The progress of the reaction was monitored by measuring Acid Value and Hydroxyl Value of reaction mixture over time. Once Acid Value stalled at around 4-2 mg, the reaction mixture was cooled down. The resulting Polyester Polyamine, produced as the major product, appeared as a yellow viscous liquid and had an Acid Value of 3.7 mg KOH/g and a Hydroxyl Value of 31.7.

EXAMPLE 10

Production of Mixed Dimethylsulfate Quats of Cetyl Dimethylamine and Dimer Acid Oligomer of PPG-4-N-Methyl-N,N-Diethanolamine Into a four-necked flask, fitted with a mechanical stirrer, condenser, thermometer, and Nitrogen inlet were charged 251.5 g (0.3 moles) of PPG-4-N-Methyl-N,N-Diethanolamine and Dimer Acid oligomer, from Example 2, 142 g (0.487 moles) of Cetyl Dimethylamine and 720 g (2.67 moles) of Stearyl Alcohol. The reaction mixture was heated to 75-80° C. and 96.3 g (0.763 moles) of Dimethyl Sulfate were slowly added. The reaction was then held at 75-80° C. for 1 hour and monitored by Base Value. Once the Base Value stabilized, the final product had a 40% total quat actives and appeared as an off-white flakeable waxy solid with a Base Value 1.5-2 mg KOH.

EXAMPLE 11

N-Methyl-N,N-Diethanolamine Dimer Acid Oligomer (non-alkoxylated)

Into a four-necked flask, fitted with a mechanical stirrer, condenser, thermometer, and a Nitrogen inlet were added 350 g (2.937 moles) of N-Methyl-N,N-Diethanolamine and 1350 g (2.467 moles) of C18 Unsaturated Dimer Fatty Acids. A catalytic amount (0.2%) of Hypophosphorous Acid was added and the mixture was gradually heated to 180° C. and held while stirring under Nitrogen for 10 hours to form hydroxyl terminated oligomer. The progress of the reaction was monitored by measuring Acid Value and Hydroxyl Value of reaction mixture over time. Once Acid Value stalled at around 4-2 mg, the reaction mixture was cooled down. The resulting Polyester Polyamine, produced as the major product, appeared as a yellow viscous liquid and had an Acid Value of 3 mg KOH/g and a Hydroxyl Value of 36.6.

EXAMPLE 12

Preparation of Mixed Dimethylsulfate Quats of Cetyl Dimethylamine and N-Methyl-N,N-Diethanolamine Dimer Acid Oligomer Into a four-necked flask, fitted with mechanical stirrer, condenser, thermometer, and Nitrogen inlet, were added 457.9 g (0.799 moles) of N-Methyl-N,N-Diethanolamine Dimer Acid oligomer from Example 11, 305.3 g (1.12 moles) of Cetyl Dimethylamine, and 1500 g (5.56 moles) of Stearyl Alcohol. The reaction mixture was heated under Nitrogen to 65-70° C. and 136.8 g (1.877 moles) of Dimethyl Sulfate were slowly added. When all the Dimethyl Sulfate was added, the reaction was held at 75-80° C. for 40 minutes and monitored by drop in Base Value. Once the Base Value stabilized, the final product had a 40% total quat actives and appeared as an off-white flakeable waxy solid with a Base Value of 2 mg KOH.

EXAMPLE 13

Dimethyl Sulfate Quat of PPG-4-N-Methyl-N,N-Diethanolamine Dimer Acid Oligomer

Into a four-necked flask, fitted with a mechanical stirrer, condenser, thermometer, an Nitrogen inlet were added 589.63 (0.7357 moles) of Dimer Acid Oligomer of PPG-4-N-Methyl-N,N-Diethanolamine from Example 9 and 400 g (4.44 moles) of 1,3 Butanediol. The mixture was heated under Nitrogen to 65-70° C. and 85.37 g (0.68 moles) of Dimethyl Sulfate were slowly added. The reaction mixture was stirred for 1 hour at 70-75° C. and was monitored by Base Value. Once the Base Value stabilized, the reaction was stopped. The final product had a 62% quat actives and appeared as a viscous yellow liquid with an Acid Value 4.5 mg KOH and Base Value 1.8 mg KOH.

EXAMPLE 14

Di-Poly(12-Hydroxystearate) Ester PPG-4-N-Methyl-N,N-Diethanolamine Adipate Oligomer (End Capped and Alkoxylated)

Into a four-neck flask, fitted with a mechanical stirrer, condenser, thermometer, and Nitrogen inlet were added 423.33 g (0.309 moles) of PPG-4-N-Methyl-N,N-Diethanolamine Adipate oligomer, from Example 2, and 876.67 (0.6188 moles) of Poly-12-Hydroxy Stearate, preparation of which is described in U.S. Pat. No. 3,778,287. A catalytic amount (0.15 w/% of the batch charge) of 50% Hypophosphorous Acid was added and the reaction was heated to 200° C. and held for 20 hours under Nitrogen sparge. In the course of the reaction, water was distilled out. Reaction progress was tracked by drop in Acid value (AV). Once the AV stabilized, the reaction was stopped and the reaction mass cooled. The resulting Di [poly(12-Hydroxy Stearate)] ester of PPG-4-N-Methyl-N,N-Diethanolamine Adipate oligomer was an amber viscous liquid with an Acid Value of 5.4 and a Base Value of 51.9.

EXAMPLE 15

Di-Polyricinoleate Ester PPG-4-N-Methyl-N,N-Diethanolamine Adipate Oligomer (End Capped and Alkoxylated)

A mixture of 299.14 g (0.142 moles) of PPG-4-N-Methyl-N,N-Diethanolamine Adipate oligomer which had Hydroxyl Value 53.4 mg KOH and was made using a similar process as described in Example 2, and 4.86 g (0.285 moles) of Polyricinoleate which had Acid Value 39.85 mg KOH and was prepared as described by U.S. Pat. No. 3,778,287 from Dec. 11, 1973 were charged into a four-necked flask, fitted with a mechanical stirrer, a condenser, a thermometer and a Nitrogen inlet. 0.15 w/% of the batch charge of 50% Hypophosphorous Acid catalyst was added into the reaction, mixture was heated to 200-220° C. and held for 16 hours under Nitrogen sparge. Reaction was monitored by Acid Value and Hydroxyl Value. Resulting Di-Polyricinoleate Poly PPG-4-N-Methyl-N,N-Diethanolamine Adipate Precursor in the form of viscous amber liquid was produced as a major product.

EXAMPLE 16

Di-Polyricinoleate Ester PPG-4-N-Methyl-N,N-Diethanolamine Adipate Oligomer Dimethyl Sulfate QUAT Into a four-necked flask, fitted with mechanical stirrer, a condenser, a thermometer a Nitrogen inlet and dropping funnel 637.58 g (0.55 moles) of Di-Polyricinoleate Poly PPG-4-N-Methyl-N,N-Diethanolamine Adipate Precursor from Example 15 was charged and 300 g (3.33 moles) of 1,3 Butanediol was added. Mixture was heated under Nitrogen to 65-70° C. and was thoroughly mixed for 15 minutes. 62.42 g (0.495 moles) of Dimethyl Sulfate was added. The reaction temperature was controlled by the speed of DMS addition and maintained below 75° C. When all Dimethyl Sulfate was added, allowed to react for 1 hour at 65-70° C. Reaction was monitored by Acid Value and Base Value. The resultant product had 70% quat actives, Base Value 2.9 mg KOH and appeared as a viscous yellow liquid.

EXAMPLE 17

PPG-4-N-Methyl-N,N-Diethanolamine Adipate Oligomer Benzyl Chloride Quat

Into a four-necked flask, fitted with mechanical stirrer, a condenser, a thermometer a Nitrogen inlet and drop funnel 298.13 g (0.621 moles equivalents) of PPG-4-N-Methyl-N,N-Diethanolamine Adipate oligomer from example 2 and 125 g of dipropylene glycol were charged. The mixture was heated to 65 and 76.87 g (0.607 moles) of benzyl chloride were slowly added. The reaction mixture temperature was then slowly increased to 90° C. Reaction progress was monitored by Base Value drop. The final product appeared as a viscous yellow liquid with a Base Value of 6.5 and a quat actives of 75.8%.

EXAMPLE 18

High SPF Sunscreen Lotion

This high SPF sunscreen lotion will provide long-lasting UV protection and will have excellent water-proof properties. It utilizes Octyl Salicylate, a UVB absorber, available from BF Goodrich.

| INGREDIENT/ INCL-CTFA NAME | WEIGHT (%) | FUNCTION | TRADE NAME (SUPPLIER) |
|---|---|---|---|
| PART A | | | |
| Deionized Water | 66.10 | Diluent | |
| Hydroxypropyl Metholcellulose | 0.25 | Thickener | Carbopol ® Ultrez ™ 10 Polymer (BF Goodrich) |
| Hydroxypropyl Methylcellulose | 0.10 | Spreading Aid | Methocel ® E4M (Dow Chemicals) |
| Propylene Glycol | 1.00 | Humectant | |
| Polymethoxy Bicyclic Oxazolidine | 0.40 | Preservative | Nuosept ™ C (Hüls) |
| Disodium EDTA | 0.05 | Chelating Agent | |
| PEG-20 Almond Glycerides | 0.40 | Particle Size Reducer | Crovol ™ A-40 (Croda) |
| PART B | | | |
| Octyl Methoxycinnamate | 7.50 | UV Absorber | Neo Heliopan ™, Type AV (Haarmann & Reimer) |
| Octyl Salicylate | 5.00 | UV Absorber | Octyl Salicylate (BF Goodrich) |
| Oxybenzone | 6.00 | UV Absorber | Neo Heliopan ™, Type BB Haarmann & Reimer |
| C12-15 Alcohols Benzoate | 5.00 | Emollient | Finsolv ® TR-2 Polymer (BF Goodrich) |
| PART C | | | |
| The compound of Example 2 | 1.5 | | |
| Acrylates Copolymer | 7.50 | Film Former | Avalure ™ AC 118 Polymer (BF Goodrich) |
| Fragrance | 0.15 | Fragrance | Fragrance #99189 "Twister" (Drom) |

Preparation Procedure:

1. PART A: Disperse Carbopol® Ultrez™ 10 polymer and Methocel® E4M in warm deionized water (40-50° C.). Reduce mixing speed after polymers are dispersed.

2. When uniform, add other PART A ingredients and mix until uniform.

3. PART B: Combine first four ingredients in PART B in a separate vessel. Heat and mix until oxybenzone has dissolved.

4. Cool PART B to 45° C. Disperse Pemulen® TR-2 in PART B and mix until well dispersed.

5. With vigorous agitation, add PART B to PART A. Mix for 20 minutes or until a smooth, non-grainy dispersion is apparent.

6. Add AMP-95® to batch, mix until a smooth product is obtained.

7. Add Avalure™ AC 118 and fragrance to batch. Mix until uniform.

EXAMPLE 19

Shampoo

| INGREDIENT/ INCL-CTFA NAME | WEIGHT (%) | FUNCTION | TRADE NAME (SUPPLIER) |
|---|---|---|---|
| PART A | | | |
| Deionized Water | 49.59 | Diluent | |
| Acrylates/C10-30 Alkyl Acrylate Crosspolymer | 0.80 | Thickener | Carbopol ® ETC ™ 2020 (BF Goodrich) |
| The compound of Example 2 | 0.2 | | |
| PART B | | | |
| Deionized Water | 10.00 | | |
| Guar Hydroxypropyl-trimonium Chloride | 0.30 | Skin Conditioner | Hi-Care ® 1000 (Rhone-Poulenc) |
| Disodium EDTA | 0.05 | Chelator | |
| PART C | | | |
| Methyl Gluceth-20 Benzoate | 2.50 | Emollient | Finsolv ® EMG-20 (Finetex) |
| Tocopheryl Acetate | 0.20 | Vitamin | Vitamin E Acetate (BASF) |
| Cetyl Alcohol | 1.00 | Opacifier | |
| Dimethicone | 0.50 | Emollient | Dow Corning ® 200 Fluid, 5000 CS (Dow Corning) |
| Sodium Laureth Sulfate (2 mole, 53%) | 15.00 | Primary Surfactant | Standapol ® ES-250 (Henkel) |
| Cocoamphoacetate (32%) | 8.50 | Mild Surfactant | Miranol ® Ultra (Rhone-Poulenc) |
| Ammonium Cocoyl Isethionate (30%) | 10.00 | Mild Surfactant | Jordapon ® ACI-30G (PPG) |
| PART D | | | |
| Phenoxyethanol, Methyl-paraben, Butylparaben, Ethylparaben and Propylparaben | 0.50 | Preservative | Phenonip ® (Nipa) |
| Fragrance | 0.50 | Fragrance | Bell Fragrance #J-7870, "Sporty" |
| D&C Violet #2 (1.0%) | 0.06 | Colorant | |
| The compound of Example 2 | 0.85 | Neutralizer | |

Preparation Procedure:

1. PART A: Disperse Carbopol® ETC™ 2020 in warm deionized water.

2. Reduce mixing speed, mix for 20 minutes.

3. Partially neutralize with NaOH (18%).

4. Mix 30 minutes or until uniform.

5. PART B: Disperse Hi-Care® 1000 in a side vessel. (NOTE: polymer will not swell yet).

6. Add disodium EDTA. When polymer swells, add PART B to PART A. (NOTE: PART B will become very thick if it is not added after swelling begins.) Mix until uniform.

7. PART C: Add 8% of Standapol® and all of Jordapon® to main batch. Mix slowly to avoid air entrapment.

8. In a side vessel, melt the following ingredients: Finsolv® EMG, Vitamin E, Cetyl Alcohol and Dimethicone at 75° C.

9. Add 7% Standapol® to melted oil phase, hold heat at 651 C. until uniform. Add Miranol® Ultra to side oil phase, maintaining temperature.

10. Add side oil/surfactant phase to main batch.

11. Mix until uniform. Do not overmix.

12. Add the following ingredients in order with mixing: Phenonip®, fragrance and color. Adjust pH with the compound of Example 2 to 6.1-6.5.

| | % W/W |
|---|---|
| Phase A | |
| Quat from Example 3 | 2.0 |
| Behentrimonuim Chloride | 1.0 |
| Cetearyl Alcohol | 4.0 |
| Crodamol OS (Octyl Stearate) | 15.0 |
| Benzophenone 3 | 5.0 |
| Octyl Methoxycinnamate | 7.5 |
| Phase B | |
| Water | 64.50 |
| Phase C | |
| Germaben II (preservative) | 1.0 |

EXAMPLE 20

Sunscreen Lotion

Procedure: Combine Phase A and heat to 75 C. In a separate vessel, combine Phase B and heat to 75 C. Add Phase A to Phase B while stirring and continue stirring while allowing to cool to 40 C. Add Phase C and continue cooling to 25 C.

| | % W/W |
|---|---|
| Phase A | |
| Quat from Example 3 | 2.0 |
| Quat from Example 12 | 3.0 |
| Cetearyl Alcohol | 4.0 |
| Crodamol OS (Octyl Stearate) | 15.0 |
| Benzophenone 3 | 5.0 |
| Octyl Methoxycinnamate | 7.5 |
| Phase B | |
| Water | 62.5 |
| Phase C | |
| Germaben II (preservative) | 1.0 |

EXAMPLE 21

Cationic Sunscreen Lotion

Procedure: Combine Phase A and heat to 75 C. In a separate vessel, combine phase B and heat to 75 C. Add Phase A to Phase B while stirring and continue stirring while allowing to cool to 40 C. Add Phase C and continue cooling to 25 C.

| | | % W/W |
|---|---|---|
| Phase A | | |
| Quat from example 12 | | 3.0 |
| Cetearyl Alcohol | | 4.0 |
| Crodamol OS (Octyl Stearate) | | 5.0 |
| Cromollient DP3A (Di-PPG-3 Myristyl Adipate) | | 5.0 |
| Petrolatum | | 3.5 |
| Dimethicone | | 3.0 |
| Crodamol SS (Cetyl Esters) | | 5.0 |
| Phase B | | |
| Water | | 69.65 |
| Carbopol 941 (Carbomer) | (thickener) | 0.15 |
| Polyester Polyamine from example 2 | (neutralizing agent) | 0.70 |
| Phase C | | |
| Germaben II (preservative) | | 1.0 |

EXAMPLE 22

Moisturising Lotion

Procedure: Dust the Carbopol 941 from Phase B into the water with mixing. Heat to 75-80° C. and add the polyester polyamine. Combine ingredients from Phase A and heat with mixing to 75-80° C. Add Phase B to Phase A while mixing and allow to cool to 40° C. Add Phase C with mixing and allow to cool to desired fill temperature.

| | % W/W |
|---|---|
| Phase A | |
| Quat from example 8 | 2.5 |
| Cromollient SCE (Di-PPG-2 Myreth-10 Adipate) | 2.0 |
| Quat from example 3 | 1.5 |
| Phase B | |
| Water | 93.0 |
| Phase C | |
| Germaben II (preservative | 1.0 |

EXAMPLE 23

Hair Conditioner

Procedure: Combine Phase A and heat to 75 C. In a separate vessel, combine Phase B and heat to 75 C. Add Phase A to Phase B while stirring and continue stirring while allowing to cool to 40 C. Add Phase C and continue cooling to 25 C.

| | % W/W |
|---|---|
| Phase A | |
| Cromollient SCE (Di-PPG-2 Myreth-10 Adipate) | 4.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 52.0 |
| Phase B | |
| Quat from example 16 | 2.0 |

EXAMPLE 24

Conditioning Shampoo

Procedure: Combine Phase A and heat to 60 C. Add Phase B and continue stirring while allowing to cool to 25 C.

| | % W/W |
|---|---|
| Phase A | |
| Cromollient SCE (Di-PPG-2 Myreth-10 Adipate) | 4.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 50.0 |
| Phase B | |
| Quat from example 16 | 2.0 |
| Quat from example 3 | 2.0 |

EXAMPLE 25

Conditioning Shampoo with UV Protection

Procedure: Combine Phase A and heat to 60 C. Add Phase B and continue stirring while allowing to cool to 25 C.

EXAMPLE 26

Shampoo for Improved Hair Shine and UV Protection

|  | % W/W |
|---|---|
| Phase A | |
| Cromollient SCE (Di-PPG-2 Myreth-10 Adipate) | 4.0 |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Germaben II (Preservative) | 1.0 |
| Water | 49.0 |
| Phase B | |
| Quat from example 17 (improves hair shine) | 2.0 |
| Quat from example 3 (provides UV protection) | 2.0 |
| Benzophenone 4 (provides UV protection) | 1.0 |

Procedure: Combine Phase A and heat to 60 C. Add Phase B and continue stirring while allowing to cool to 25 C.

| Ingredients | % W/W |
|---|---|
| Part A | |
| Procetyl AWS (PPG-5-Ceteth-20) | 49.0 |
| Crodacol C-95 (Cetyl Alcohol) | 16.0 |
| Quat from example 8 | 5.0 |
| Quat from example 17 | 2.0 |
| Dimethicone | 3.0 |
| Part B | |
| Aluminum Chlorhydrate | 25.0 |

EXAMPLE 27

Antiperspirant Stick

Procedure: Combine Part A ingredients and heat to 60-65° C. Cool to 50-55° C. and while mixing, Part B while being careful to avoid aeration. Cool to desired fill temperature.

EXAMPLE 28

Clear Deodorant Stick

| Ingredients | % W/W |
|---|---|
| Part A | |
| Sodium Stearate C-1 | 7.7 |
| Incromide CA (Cocamide DEA) | 7.0 |
| Quat from example 17 | 0.5 |
| Quat from example 16 | 2.0 |
| Propylene Glycol | 57.0 |
| Triclosan | 0.3 |
| Probutyl DB-10 (PPG-10 Butane Diol) | 7.5 |
| Part B | |
| Deionized Water | 18.0 |

Procedure: Combine all Part A ingredients ad increase temperature to 70-80° C. using high agitation. Continue stirring for 5-10 minutes once temperature is reached then slowly start adding Part B over a 5-10 minute period. Pour into molds.

EXAMPLE 29

UV Protecting Conditioning Spray Containing Crodasorb UV-HPP

A UV-Protecting Conditioning Spray has the following content:

| Ingredients | % w/w |
|---|---|
| Deionized Water | 90.9 |
| CRODASORB UV-HPP (Polyquaternium-59 (and) Butylene Glycol available from Croda, Inc. (the same quat as produced in Example 3) | 1.6 |
| INCROMECTANT LAMEA (Acetamide MEA (and) Lactamide MEA) | 4.0 |
| INCROMATE ISML (Isostearamidopropyl Morpholine Lactate | 1.0 |
| GLYCEROX 767 (PEG-6 Caprylic/Capric Glycerides) | 1.0 |
| CROTEIN HKP/SF (Hydrolyzed Keratin) | 1.0 |
| Sodium Hydroxymethylglycinate (1) | 0.5 |

Procedure: Add all ingredients one after another with mixing. Adjust to pH-5.5 with 10% aqueous solution of citric acid.

EXAMPLE 30

UV-Protecting Shampoo with Crodasorb UV-HPP

UV-protecting shampoo has the following content:

UV-protecting shampoo has the following content:

| Ingredients | (%) w/w | |
|---|---|---|
| | Shampoo with viscosity of 8000 cps | Shampoo with viscosity of 9000 cps |
| Deionized Water | 47.5 | 44.5 |
| Ammonium Lauryl Sulfate | 24.0 | — |
| Ammonium Laureth Sulfate | 12.0 | — |
| Sodium Lauryl Sulfate | — | 25.0 |
| Sodium Laureth Sulfate | — | 13.0 |
| INCROSUL OTS (Disodium Oleth-3 Sulfosuccinate) | 5.0 | 5.0 |
| CROSULTAINE C-50 (Cocamidopropyl Hydroxysultaine) | 5.0 | 5.0 |
| CRODASORB UV-HPP (Polyquaternium-59 (and) Butylene Glycol) | 2.5 | 2.5 |
| CROTHIX LIQUID (PEG-150 Pentaerythrityl Tetrastearate (and) PEG-6 Caprylic/Capric Glycerides (and) Water) | 2.0 | 3.0 |
| TRITISOL (Hydrolyzed Wheat Protein | 1.0 | 1.0 |
| Propylene Glycol (and) Diazolidinyl Urea (and) Methylparaben (and) Propylparaben | 1.0 | 1.0 |

Procedure: Add ingredients one after another with mixing. Adjust pH to 5.5 with 10% solution of citric acid.

EXAMPLE 31

Preparation of PEG2, PPG-4 Stearylamine

To a clean, dry stirred tank vessel equipped with Nitrogen sparge was charged 1530.69 g (4.172 mole equivalents) of PEG-2 Stearylamine and 5.56 g of 45% Potassium Hydroxide Solution. The vessel was purged with nitrogen and a vacuum 30 mm Hg was applied for one hour after heating to 110° C. After one hour under vacuum, the batch heated to 130° C. and 969.31 g (16.689 mole equivalents) of Propylene Oxide was bubbled into the vessel at a constant rate to maintain an internal pressure of 40-45 psig. After all Propylene Oxide was added, the batch was left to react to constant pressure, and then vacuum was applied for one hour. The finished product was a hazy amber liquid with a Base Value of 92.9 and a Hydroxyl Value of 288.5.

EXAMPLE 32

Preparation of PEG-2, PPG-4 Stearylamine Adipate Oligomer

To a clean, dry stirred tank vessel equipped with Nitrogen sparge was charged 1670.07 g (2.766 mole equivalents) of PEG-2 PPG-4 Stearylamine from example 4, 329.93 g (2.258 mole equivalents) of Adipic Acid and 3 g of 50% Hypophosphorous Acid. The batch was heated to 220-225° C. and a vacuum of 30 mm Hg was applied for 10-12 hours to form the Hydroxyl terminated oligomer. During this time, the progress of the reaction was monitored via the drop in Acid Value. The reaction was considered complete when an Acid Value of less than 7 mg KOH was obtained. The product was a viscous amber liquid with a Hydroxyl Value of 32.4 and a Base Value of 78.6.

EXAMPLE 33

Preparation of PEG-2, PPG-4 Stearalammonium Methosulfate Adipate Oligomer

To a clean, dry 4-neck round bottom flask equipped with stirrer, Nitrogen sparge, temperature probe, reflux condenser and drop funnel was charged 310.98 g (0.434 mole equivalents) of PEG-2 PPG-4 Stearylamine Adipate Oligomer from example 5 and 192.49 g of 1,3-Butanediol. Using the drop funnel, 46.53 g (0.369 mole equivalents) of Dimethyl Sulfate was added over a 15-20 minute period while maintaining a temperature between 70-80° C. After addition of the Dimethyl Sulfate was complete, the batch was allowed to react for an additional hour at 70-80° C. after which the Base Value of the product was checked. The reaction was considered finished once the Base Value was below 6 mg KOH. The finished product was a clear liquid with a Cationic Activity of 67.7%.

EXAMPLE 34

Preparation of PPG-4 N-Methyl-N,N-Diethanolamine Oligoester of Mixed Dimer Acid/Adipic Acid To a clean, dry 4-neck round bottom flask equipped with stirrer, Nitrogen sparge, temperature probe and distillation apparatus is charged 247.25 g (0.704 mole equivalents) of the PPG-4 N-Methyl-N,N-Diethanolamine from example 1, 51.40 g (0.352 mole equivalents) of Adipic Acid, and 201.35 g (0.352 mole equivalents) of C36 Dimer acid (Unidyme 14™ from Arizona Chemical Co.). The reaction is heated to 220-225° C. under Nitrogen and monitored by the drop in Acid Value. The reaction is considered complete when the Acid Value is less than 7.

EXAMPLE 35

Preparation of Methosulfate Quat of PPG-4 N-Methyl-N,N-Diethanolamine Oligoester of Mixed Dimer Acid and Adipic Acid To a clean, dry 4-neck round bottom flask equipped with stirrer, Nitrogen sparge, temperature probe, reflux condenser and drop funnel is charged 259.82 g (0.375) of the PPG-4 N-Methyl-N,N-Diethanolamine Dimer Acid/Adipate Oligomer from example 7 and 199.98 g of 1,3-Butanediol. Using the drop funnel, 40.21 g (0.319 mole equivalents) of Dimethyl Sulfate is added over a 15-20 minute period while maintaining a temperature between 70-80° C. After addition of the Dimethyl Sulfate is complete, the batch is allowed to react for an additional hour at 70-80° C. after which the Base Value of the product is checked. The reaction is considered finished once the Base Value is below 6 mg KOH.

EXAMPLE 36

Preparation of PEG-2, PPG-4 Stearalmine Oxide Adipate Oligomer

To a clean, dry 4-neck round bottom flask equipped with stirrer, Nitrogen sparge, temperature probe, reflux condenser and drop funnel is charged 310.98 g (0.434 mole equivalents) of PEG-2, PPG-4 Stearylamine Adipate Oligomer from example 5 and 192.49 g of 1,3-Butanediol. Using the drop funnel, 25 g (0.369 mole equivalents) of 50% Hydrogen Peroxide is added over a 15-20 minute period while maintaining a temperature between 70-80° C. After addition of the Hydrogen Peroxide, the batch is allowed to react for an additional hour at 70-80° C. After which the reaction is considered complete. The resulting product contains amine oxide functional groups along the oligomer backbone.

EXAMPLE 37

Preparation of Mixed Dimethyl Sulfate Quat and Amine Oxide of PEG-2, PPG-4 Stearalmine Adipate Oligomer To a clean, dry 4-neck round bottom flask equipped with stirrer, Nitrogen sparge, temperature probe, reflux condenser and drop funnel is charged 310.98 g (0.434 mole equivalents) of PEG-2, PPG-4 Stearylamine Adipate oligomer from example 5 and 192.49 g of 1,3-Butanediol. Using the drop funnel, 25.2 g (0.20 mole equivalents) of Dimethyl Sulfate over a 15-20 minute period while maintaining a temperature of 70-80° C. Allow to react for an additional hour then 8.1 g (0.119 moles equivalents) of 50% Hydrogen Peroxide is added over a 15-20 minute period while maintaining a temperature between 70-80° C. After addition of the Hydrogen Peroxide, the batch is allowed to react for an additional hour at 70-80° C. after which the reaction is considered complete. The resulting product contains a mixture of quat and amine oxide functional groups along the oligomer backbone.

EXAMPLE 38

Preparation of 3-Dimethylaminopropyl Gluconamide

3-Dimethylaminopropyl Gluconamide was prepared as described in Example 4 of U.S. Pat. No. 4,038,294.

EXAMPLE 39

Preparation of the Quat of PPG-4 N-Methyl-N,N-Diethanolamine Oligoester of Mixed Dimer Acid and Adipic Acid Containing a 3-Dimethylaminopropyl Gluconamide Pendant Group To a clean, dry 4-neck round bottom flask equipped with stirrer, Nitrogen sparge, temperature probe, reflux condenser and drop funnel is charged 259.82 g (0.375 mole equivalents) of the PPG-4 N-Methyl-N,N-Diethanolamine Dimer Acid/Adipate Oligomer from example 7 and 0.199.98 g of 1,3-Butanediol. Using the drop funnel, 29.6 g (0.30 mole equivalents) of 37% HCl is added followed by 27.75 g (0.30 mole equivalents) of epichlorohydrin and (0.30 mole equivalents) of 3-Dimethylaminopropyl Gluconamide from example 11. The reaction is stirred at 70-80° C. until the base value stabilizes. The resulting product is an oligoester oligoquat with pendant 3-Dimethylaminopropyl Gluconamide side chains.

EXAMPLE 40

Preparation of the Quat of PPG-4 N-Methyl-N,N-Diethanolamine Oligoester of Mixed Dimer Acid and Adipic Acid Containing a Methoxy Silane Pendant Group To a clean, dry 4-neck round bottom flask equipped with stirrer, Nitrogen sparge, temperature probe, reflux condenser and drop funnel is charged 259.82 g (0.375 mole equivalents) of the PPG-4 N-Methyl-N,N-Diethanolamine Dimer Acid/Adipate Oligomer from example 7 and 0.199.98 g of 1,3-Butanediol. Using the drop funnel, 29.6 g (0.30 mole equivalents) of 37% HCl is added followed by 70.9 g (0.30 mole equivalents) of 3-Glycidoxy-propylmethoxy silane (product Z-6040 from Dow Corning). The reaction is stirred at 70-80° C. until the acid value stabilizes. The resulting product is an oligoester oligoquat with pendant trimethoxysilane side chains.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound of Formula (VIII)

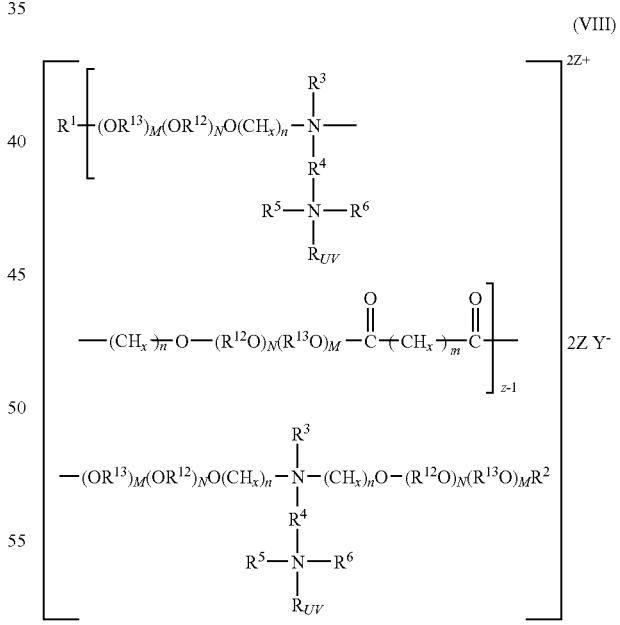

wherein $R^1$ and $R^2$ are independently

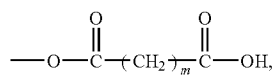

hydrogen, or a saturated or unsaturated, straight chain or branched, substituted or unsubstituted alkyl, alkylene, or alkoxy group having 1 to 60 carbon atoms;

- $R^3$, $R^5$, $R^6$, and $R^{11}$ are independently hydrogen or a saturated or unsaturated, straight chain or branched, substituted or unsubstituted alkyl, alkylene, or alkoxy group having 1 to 60 carbon atoms;
- $R^4$ is a saturated or unsaturated, straight chain or branched, substituted or unsubstituted alkyl, alkylene, or alkoxy group having 1 to 60 carbon atoms;
- $R^{12}$ and $R^{13}$ are independently straight chain or branched, saturated or unsaturated, substituted or unsubstituted, lower alkyl groups having 1 to 6 carbon atoms;
- $R_{UV}$ has the structure $—(CH_x)_b—NH—C(O)—R^{10}$;
- $(CH_x)_n$, $(CH_x)_m$, and $(CH_x)_b$ are independently straight chain or branched, saturated or unsaturated, alkyl or alkylene groups;
- $R^{10}$ is a substituted or unsubstituted, saturated or unsaturated group, wherein said group contains a substituted or unsubstituted 6-membered aromatic ring;
- Y is a salt-forming anion;
- Z is a salt-forming cation;
- Z is 2-100;
- x is 0, 1, or 2;
- b is 1 to 10;
- n is 1 to 6;
- m is 1 to 300; and
- N and M are independently 0 to 100.

2. The compound of claim 1, wherein $R^{12}$ and $R^{13}$ are $—CH(CH_3)CH_2—$.

3. The compound of claim 1, wherein $R^{12}O$ or $R^{13}O$ are independently ethoxy or propoxy.

4. The compound of claim 1, wherein N is 0 to 40.

5. The compound of claim 4, wherein N is 0 to 3.

6. The compound of claim 1, wherein M is 0 to 40.

7. The compound of claim 6, wherein M is 0 to 3.

8. The compound of claim 1, wherein $R^{10}$ is derived from para-aminobenzoic acid (PABA), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid.

9. The compound of claim 1, wherein $R^{10}$ is

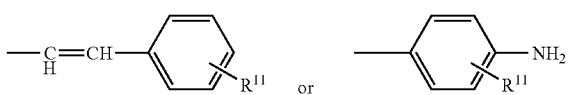

and where $R^{11}$ is hydrogen, lower alkyl, halide or methoxy.

10. The compound of claim 1, wherein $R_{UV}$ is

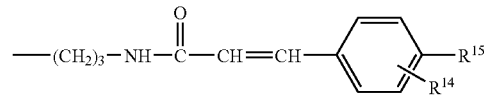

and $R^{14}$ and $R^{15}$ are independently H, $—NH_2$, $NO_2$, $CH_3O—$, or $(CH_3)_2N—$.

11. The compound of claim 10, wherein $R^{14}$ and $R^{15}$ are H.

12. The compound of claim 1, said compound having the Formula (IX)

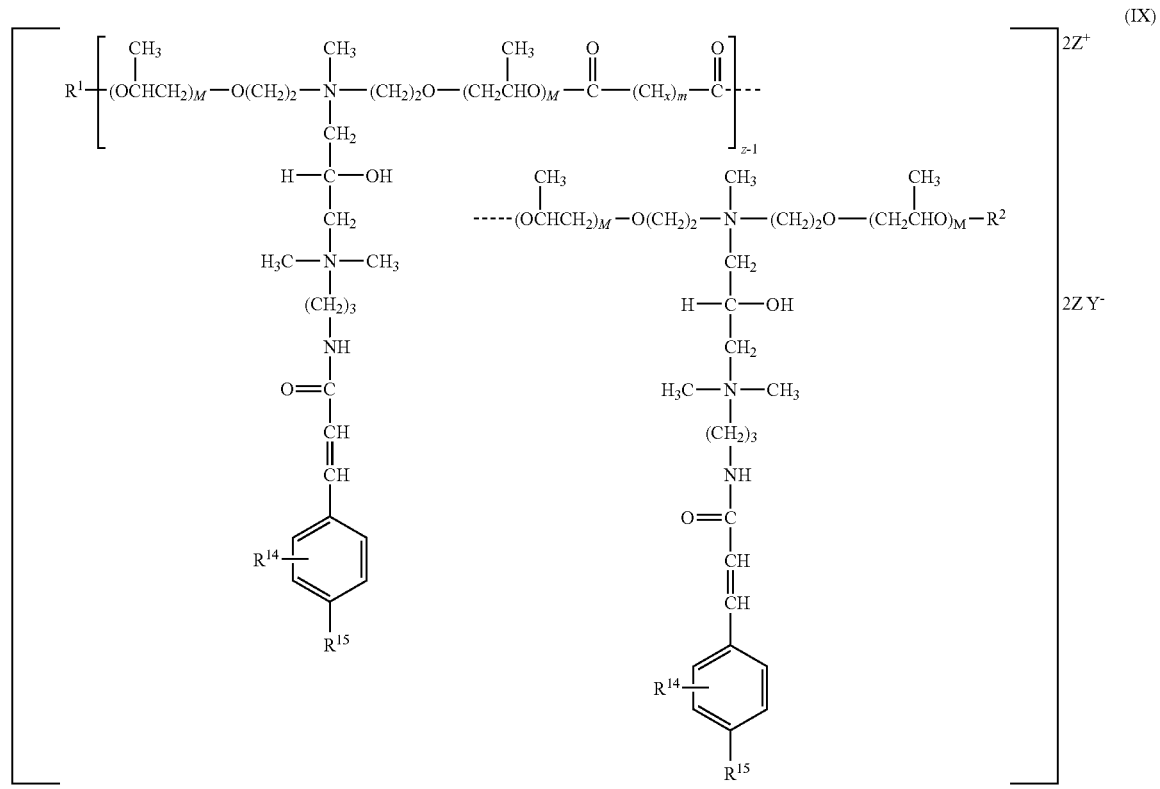

where $R^{14}$ and $R^{15}$ are independently hydrogen, —$NH_2$, $NO_2$, $CH_3O$—, or $(CH_3)_2N$—;
  m is 1 to 5; and
  z is 4 to 6.

13. The compound of claim 12, wherein $R^1$ and $R^2$ are H.

14. The compound of claim 12, wherein $R^1$ and $R^2$ are independently $$-O-\overset{O}{\underset{\|}{C}}-(CH_2)_{\overline{m}}-\overset{O}{\underset{\|}{C}}-OH;$$

and m is 1-5.

15. The compound of claim 12, wherein one of $R^1$ or $R^2$ is hydrogen and the other of $R^1$ or $R^2$ is $$-O-\overset{O}{\underset{\|}{C}}-(CH_2)_{\overline{m}}-\overset{O}{\underset{\|}{C}}-OH;$$

and m is 1-5.

16. The compound of claim 1, further comprising at least one end cap.

17. The compound of claim 1, further comprising two end caps.

18. A compound of Formula (VIII)

$$\left[ R^1 + (OR^{13})_M(OR^{12})_NO(CH_x)_n - \underset{\underset{R^4}{|}}{\overset{R^3}{\underset{|}{N}}} - \\ \underset{\underset{R_{UV}}{|}}{\overset{R^5-N-R^6}{}} \\ -(CH_x)_{\overline{n}}-O-(R^{12}O)_N(R^{13}O)_M-\overset{O}{\underset{\|}{C}}-(CH_x)_{\overline{m}}-\overset{O}{\underset{\|}{C}} \right]_{z-1}^{2Z+} 2Z\ Y^-$$

$$-(OR^{13})_M(OR^{12})_NO(CH_x)_n-\underset{\underset{R^4}{|}}{\overset{R^3}{\underset{|}{N}}}-(CH_x)_nO-(R^{12}O)_N(R^{13}O)_MR^2 \\ \underset{\underset{R_{UV}}{|}}{\overset{R^5-N-R^6}{}}$$

wherein $R^1$ and $R^2$ are independently $$-O-\overset{O}{\underset{\|}{C}}-(CH_2)_{\overline{m}}-\overset{O}{\underset{\|}{C}}-OH,$$

hydrogen, or a saturated or unsaturated, straight chain or branched, substituted or unsubstituted alkyl, alkylene, or alkoxy group having 1 to 60 carbon atoms;

$R^3$, $R^5$, $R^6$, and $R^{11}$ are independently hydrogen or a saturated or unsaturated, straight chain or branched, substituted or unsubstituted alkyl, alkylene, or alkoxy group having 1 to 60 carbon atoms;

$R^4$ is a saturated or unsaturated, straight chain or branched, substituted or unsubstituted alkyl, alkylene, or alkoxy group having 1 to 60 carbon atoms;

$R^{12}$ and $R^{13}$ are independently straight chain or branched, saturated or unsaturated, substituted or unsubstituted, lower alkyl groups having 1 to 6 carbon atoms;

$R_{UV}$ has the structure —$(CH_x)_b$—NH—C(O)—$R^{10}$;

$(CH_x)_n$, $(CH_x)_m$, and $(CH_x)_b$ are independently straight chain or branched, saturated or unsaturated alkyl or alkylene groups;

$R^{10}$ is a substituted or unsubstituted, saturated or unsaturated group, wherein said group contains a substituted or unsubstituted 6-membered aromatic ring;

Y is a salt-forming anion;
Z is a salt-forming cation;
Z is 2-100;
x is 0, 1, or 2;
b is 1 to 10;
n is 1 to 6;
m is 1 to 300; and
N and M are independently 0 to 100,
with the proviso that there is at least one alkoxy group.

19. The compound of claim 18, wherein $R^{12}$ and $R^{13}$ are —$CH(CH_3)CH_2$—.

20. The compound of claim 18, wherein $R^{12}O$ or $R^{13}O$ are independently ethoxy or propoxy.

21. The compound of claim 18, wherein $R^{10}$ is derived from para-aminobenzoic acid (PABA), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, avobenzone, and 2,6-dicarboxynaphtalenic acid.

22. The compound of claim 18, wherein $R^{10}$ is $$-\underset{H}{\overset{}{C}}=CH-\!\!\!\bigcirc\!\!\!-R^{11} \quad \text{or} \quad -\!\!\!\bigcirc\!\!\!\underset{R^{11}}{\overset{}{-}}NH_2$$

and where $R^{11}$ is hydrogen, lower alkyl, halide or methoxy.

23. The compound of claim 18, wherein $R_{UV}$ is $$-(CH_2)_3-NH-\overset{O}{\underset{\|}{C}}-CH=CH-\!\!\!\bigcirc\!\!\!\underset{R^{14}}{\overset{R^{15}}{}}$$

and $R^{14}$ and $R^{15}$ are independently H, —$NH_2$, $NO_2$, $CH_3O$—, or $(CH_3)_2N$—.

24. The compound of claim 23, wherein $R^{14}$ and $R^{15}$ are H.

25. A compound Poly(N-Hydroxypolyoxypropylethyl) N-Adipyl-Poly-Oxypropyl)-N-Methyl-N-(2-Hydroxy-3-Cinnamidopropyl Dimethyl Ammonium Chloride) Methane Sulfonate.

26. A compound having the structure:
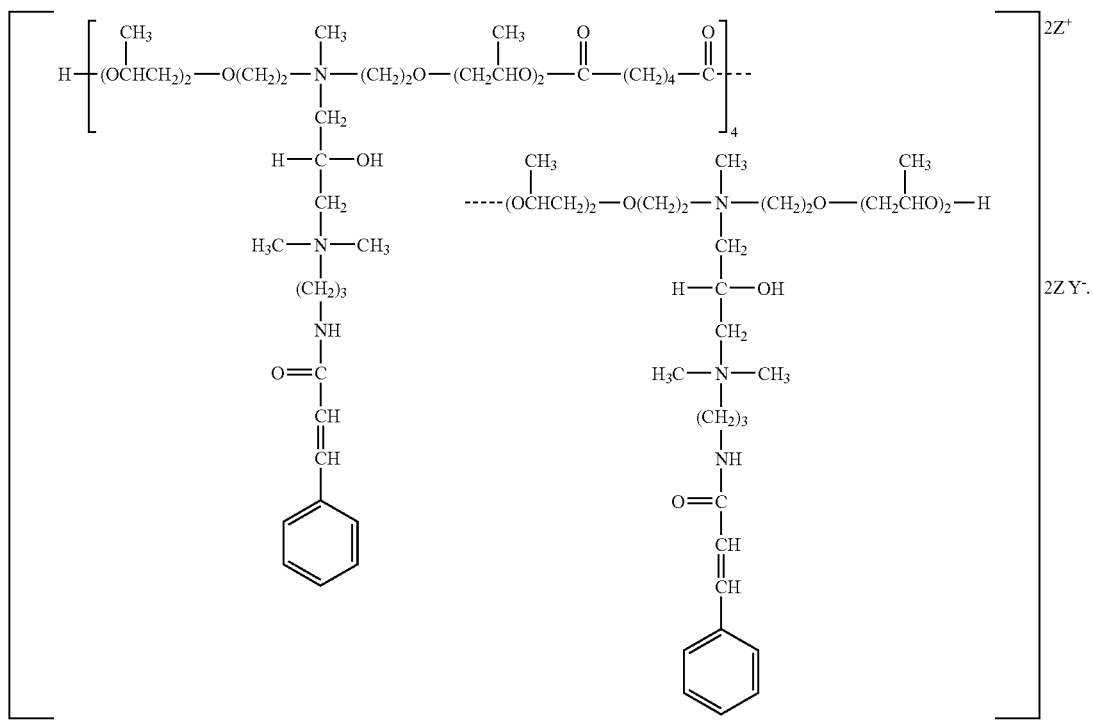
wherein
Y is a salt-forming anion; and
Z is a salt-forming cation.
27. A compound having the structure:
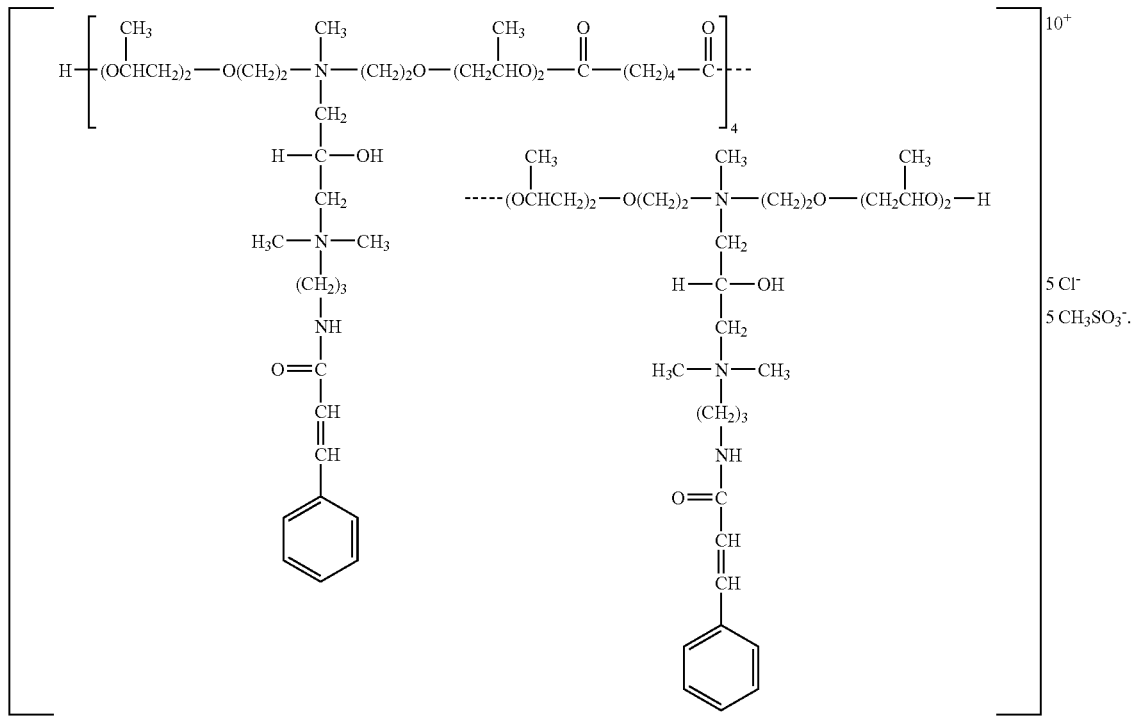

28. A pharmaceutical, cosmetic, or personal care product comprising:
- a pharmaceutically or cosmetically-acceptable solvent; and
- said oligoester of claim 1 present in an amount of from about 0.01% to about 99.0% by weight based on the combined weight of said oligoester and said solvent; and
- at least one active or additional ingredient, provided in an amount which is effective for its intended use,
- wherein said pharmaceutical, cosmetic, or personal care product is provided in the form of a lotion, gel, spray, cream and the like, hand cleaner, bath composition, suntan oil, antiperspirant composition, perfume, cologne, cold cream, pre-shave, deodorant, treated powder, nose spray, bandage, transdermal drug applicator, skin moisturizer, facial cleanser, cleansing cream, skin gel, shampoo, hair conditioner rinse, cream rinse, detergent, make-up product, permanent waving product, lipstick, mascara, blush, foundation, rouge, mousse, spray, styling gel, nail polish, nail conditioner, dye or hair coloring product.

29. The pharmaceutical, cosmetic, or personal care product of claim 28, wherein said oligoester is present in an amount of from about 5% to about 95% by weight based on the combined weight of said oligoester and said solvent.

30. The pharmaceutical, cosmetic, or personal care product of claim 28, wherein said product is provided in the form of skin moisturizer, facial cleanser, shampoo, hair conditioner, cream rinse, styling gel, dye or hair coloring product.

31. The pharmaceutical, cosmetic, or personal care product of claim 28, wherein said oligoester includes between about 2 and about 100 structural units.

32. The pharmaceutical, cosmetic, or personal care product of claim 28, wherein said oligoester has a molecular weight of about 100,000 or less.

33. The pharmaceutical, cosmetic, or personal care product of claim 28, wherein said oligoester includes at least one alkoxy group bound to, and forming part of at least one of said diol fragments.

34. The pharmaceutical, cosmetic, or personal care product of claim 28, wherein said at least one active or additional ingredients, provided in an amount which is effective for its intended use include pharmaceutically active ingredients, UV-absorbers, fragrances, pigments, dyes, hair or skin conditioners, cleaning agents, hair styling agents, antidandruff agents, hair growth promoters, perfumes, sunscreen compounds, pigments, moisturizers, film formers, humectants, alpha-hydroxy acids, hair colors, make-up agents, detergents, thickening agents, emulsifiers, antiseptic agents, deodorant actives, surfactants, agents which enhance permeation into or through the skin, emollients, emulsifiers, humectants, softeners, lubricants, penetrants, plasticizers, dispersants, thickening agents, preservatives, buffers, chelating agents, foaming agents, coupling agents, proteins, salts, and oils all provided in conventional and/or approved amounts.

35. An additive for pharmaceutical, cosmetic, or personal care products comprising:
- a pharmaceutically or cosmetically acceptable solvent; and
- an oligoester of claim 1, said oligoester being present in an amount of from about 0.01% to about 99.0% by weight of said additive.

* * * * *

UNITED STATES PATENT AND TRADEMARK OFFICE
CERTIFICATE OF CORRECTION

PATENT NO.      : 7,611,725 B2                              Page 1 of 1
APPLICATION NO. : 10/356208
DATED           : November 3, 2009
INVENTOR(S)     : Pereira et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 850 days.

Signed and Sealed this

Twelfth Day of October, 2010

David J. Kappos
*Director of the United States Patent and Trademark Office*